(12) United States Patent
Lang et al.

(10) Patent No.: US 9,511,027 B1
(45) Date of Patent: Dec. 6, 2016

(54) CALCIUM SUPPLEMENT HAVING ENHANCED ABSORPTION

(75) Inventors: Kevin W. Lang, Lloyd Neck, NY (US); Gregory B. Murphy, Sands Point, NY (US); Gregory E. Urbanski, Sahuarita, AZ (US)

(73) Assignee: Delavau L.L.C., Philadelphia, PA (US)

( * ) Notice: Subject to any disclaimer, the term of this patent is extended or adjusted under 35 U.S.C. 154(b) by 25 days.

(21) Appl. No.: 13/452,759

(22) Filed: Apr. 20, 2012

Related U.S. Application Data

(63) Continuation of application No. 11/855,807, filed on Sep. 14, 2007.

(60) Provisional application No. 60/825,853, filed on Sep. 15, 2006, provisional application No. 60/892,183, filed on Feb. 28, 2007.

(51) Int. Cl.
*A61K 9/20* (2006.01)

(52) U.S. Cl.
CPC .................. *A61K 9/2054* (2013.01)

(58) Field of Classification Search
None
See application file for complete search history.

(56) References Cited

U.S. PATENT DOCUMENTS

| | | |
|---|---|---|
| 3,627,583 A | 12/1971 | Troy et al. |
| 3,639,168 A | 2/1972 | Monti et al. |
| 3,639,169 A | 2/1972 | Broeg et al. |
| 3,646,689 A | 3/1972 | Kuchenthal et al. |
| 3,843,778 A | 10/1974 | Diamond et al. |
| 3,933,670 A | 1/1976 | Brill et al. |
| 3,969,546 A | 7/1976 | Saeman |
| 4,051,222 A | 9/1977 | Gnyra |
| 4,054,631 A | 10/1977 | Mori et al. |
| 4,071,304 A | 1/1978 | Chauvin et al. |
| 4,140,760 A | 2/1979 | Withington |
| 4,166,644 A | 9/1979 | Kay et al. |
| 4,170,658 A | 10/1979 | Skinner et al. |
| 4,183,738 A | 1/1980 | Carmon |
| 4,230,693 A | 10/1980 | Izzo et al. |
| 4,257,817 A | 3/1981 | Mathur et al. |
| 4,339,428 A | 7/1982 | Tencza |
| 4,409,016 A | 10/1983 | Mutsers et al. |
| 4,446,135 A | 5/1984 | Fountaine |
| 4,486,412 A | 12/1984 | Shah et al. |
| 4,533,543 A | 8/1985 | Morris et al. |
| 4,540,584 A | 9/1985 | Someya |
| 4,582,615 A | 4/1986 | Ramachandran et al. |
| 4,609,473 A | 9/1986 | Ramachandran et al. |
| 4,609,543 A | 9/1986 | Morris et al. |
| 4,650,669 A | 3/1987 | Alexander et al. |
| 4,656,028 A | 4/1987 | Cuca |
| 4,664,915 A | 5/1987 | Simonian |
| 4,678,661 A | 7/1987 | Gergely et al. |
| 4,711,748 A | 12/1987 | Irwin et al. |
| 4,744,987 A | 5/1988 | Mehra et al. |
| 4,746,445 A | 5/1988 | Weinstein |
| 4,769,359 A | 9/1988 | Audley et al. |
| 4,772,467 A | 9/1988 | Pak |
| 4,812,303 A | 3/1989 | Iorio |
| 4,828,820 A | 5/1989 | Glass et al. |
| 4,851,137 A | 7/1989 | Weinstein |
| 4,861,590 A | 8/1989 | Grodberg |
| 4,866,023 A | 9/1989 | Ritter et al. |
| 4,867,977 A | 9/1989 | Gailly et al. |
| 4,883,788 A | 11/1989 | Day et al. |
| 4,889,725 A | 12/1989 | Veltman |
| 4,946,679 A | 8/1990 | Thys-Jacobs |
| 4,954,134 A | 9/1990 | Harrison et al. |
| 5,002,777 A | 3/1991 | Cuca |
| 5,173,305 A | 12/1992 | Grimberg |
| 5,196,149 A | 3/1993 | Scarpelli |
| 5,228,895 A | 7/1993 | Kelly et al. |
| 5,302,396 A | 4/1994 | Phadke et al. |
| 5,348,745 A | 9/1994 | Daher |
| 5,362,688 A | 11/1994 | Porta et al. |
| 5,366,513 A | 11/1994 | Goldmann et al. |
| 5,429,825 A | 7/1995 | Reo et al. |
| 5,443,850 A | 8/1995 | Thys-Jacobs |
| 5,455,050 A | 10/1995 | Beyerle et al. |
| 5,536,432 A | 7/1996 | Cicciari et al. |
| 5,571,334 A | 11/1996 | Dunn et al. |
| 5,603,979 A | 2/1997 | Lasdon et al. |
| 5,607,695 A | 3/1997 | Ek et al. |
| 5,629,013 A | 5/1997 | Upson et al. |
| 5,635,208 A | 6/1997 | Parekh et al. |
| 5,637,313 A | 6/1997 | Chau et al. |
| 5,665,692 A | 9/1997 | Kaminsky |

(Continued)

FOREIGN PATENT DOCUMENTS

| | | |
|---|---|---|
| CA | 2019324 C | 8/1996 |
| CA | 2326989 A1 | 10/1999 |
| CA | 2192086 C | 1/2000 |
| CA | 2501587 C | 6/2008 |
| CA | 2534056 C | 6/2012 |
| EP | 0386868 B1 | 9/1990 |
| EP | 0396972 B2 | 11/1990 |
| EP | 0439373 A1 | 7/1991 |
| EP | 0476696 B1 | 3/1993 |
| EP | 0814771 B1 | 1/1998 |
| EP | 1128815 B1 | 10/2006 |
| JP | 05339171 | 12/1993 |
| WO | 00/28973 A1 | 5/2000 |
| WO | 01/45677 A1 | 6/2001 |
| WO | 02/100422 | 12/2002 |

OTHER PUBLICATIONS

"CalEssence Enhanced Purity", Specialty Minerals, pp. 1-2; 2000.*
Docket for Civil Action No. 2:12-05378-ES-CLW, *Delavau, LLC* v. *J.M. Huber Corporation and J.M. Huber Micropowders Inc.*, filed Aug. 27, 2012, in the United States District Court for the District of New Jersey, obtained Nov. 20, 2013 (22 pages).

(Continued)

*Primary Examiner* — Susan Tran
(74) *Attorney, Agent, or Firm* — Lewis Rice LLC

(57) ABSTRACT

Dietary calcium supplements comprising highly bioavailable forms of calcium carbonate and methods of using these calcium carbonate forms to improve calcium balance, strengthen bones, and prevent, treat, and/or ameliorate bone loss associated with osteoporosis are provided.

13 Claims, 27 Drawing Sheets

(56) References Cited

U.S. PATENT DOCUMENTS

| | | | |
|---|---|---|---|
| 5,743,934 A | 4/1998 | Wommack et al. |
| 5,747,067 A | 5/1998 | Auguello et al. |
| 5,779,464 A | 7/1998 | Fan et al. |
| 5,807,580 A | 9/1998 | Luber |
| 5,858,413 A | 1/1999 | Jettka et al. |
| 5,874,065 A | 2/1999 | Pardini |
| 5,914,135 A | 6/1999 | Dubek et al. |
| 5,919,491 A | 7/1999 | Adusumilli et al. |
| 5,922,704 A | 7/1999 | Bland |
| 5,929,021 A | 7/1999 | Dhanuka et al. |
| 5,942,255 A | 8/1999 | Klesges |
| 5,997,599 A | 12/1999 | Wommack et al. |
| 6,030,645 A | 2/2000 | Tritsch et al. |
| 6,036,933 A | 3/2000 | Ramsay |
| 6,040,333 A | 3/2000 | Jackson |
| 6,056,905 A | 5/2000 | Akkermans et al. |
| 6,066,342 A | 5/2000 | Gurol et al. |
| 6,077,820 A | 6/2000 | Dhanuka et al. |
| 6,103,274 A | 8/2000 | Jettka et al. |
| 6,133,223 A | 10/2000 | Sampaio et al. |
| 6,217,851 B1 | 4/2001 | Kleinberg et al. |
| 6,217,909 B1 | 4/2001 | Sherwood et al. |
| 6,228,849 B1 | 5/2001 | Thys-Jacobs |
| 6,248,335 B1 | 6/2001 | Duan et al. |
| 6,251,439 B1 | 6/2001 | Baron |
| 6,254,893 B1 | 7/2001 | MacKeen |
| 6,274,544 B1 | 8/2001 | Akkermans et al. |
| 6,287,599 B1 | 9/2001 | Burnside et al. |
| 6,287,607 B2 | 9/2001 | Pak et al. |
| 6,312,659 B1 | 11/2001 | Wise |
| 6,325,836 B1 | 12/2001 | Wommack et al. |
| 6,368,638 B1 | 4/2002 | Tiongson |
| 6,372,253 B1 | 4/2002 | Daggey et al. |
| 6,384,087 B1 | 5/2002 | Zemel et al. |
| 6,395,301 B1 | 5/2002 | Cantin |
| 6,413,291 B1 | 7/2002 | Wommack et al. |
| 6,429,184 B1 | 8/2002 | Akkerman et al. |
| 6,447,809 B1 | 9/2002 | Krumhar et al. |
| 6,479,474 B2 | 11/2002 | DeLuca et al. |
| 6,488,966 B2 | 12/2002 | Baron |
| 6,492,024 B1 | 12/2002 | Walter |
| 6,499,984 B1 | 12/2002 | Ghebre-Sellassie et al. |
| 6,558,711 B1 | 5/2003 | Baron |
| 6,569,472 B1 | 5/2003 | Zyck et al. |
| 6,592,837 B2 | 7/2003 | Denholm et al. |
| 6,635,278 B1 | 10/2003 | Dahl et al. |
| 6,680,288 B1 | 1/2004 | Groot et al. |
| 6,682,762 B2 | 1/2004 | Register |
| 6,686,044 B2 | 2/2004 | Nakai et al. |
| 6,716,454 B2 | 4/2004 | Meignant et al. |
| 6,790,462 B2 | 9/2004 | Hendricks |
| 6,808,700 B2 | 10/2004 | Kiji et al. |
| 6,818,228 B1 | 11/2004 | Walsdorf et al. |
| 6,863,902 B2 | 3/2005 | Thosar et al. |
| 6,936,087 B2 | 8/2005 | Wommack et al. |
| 7,018,972 B2 | 3/2006 | Akkerman et al. |
| 7,029,504 B2 | 4/2006 | Rabie et al. |
| 7,029,703 B2 | 4/2006 | Krumhar et al. |
| 7,053,038 B2 | 5/2006 | Groot et al. |
| 7,166,313 B2 | 1/2007 | Diddle et al. |
| 7,169,417 B2 | 1/2007 | Dibble et al. |
| 7,198,653 B2 | 4/2007 | Lang et al. |
| 7,252,850 B2 | 8/2007 | Levin et al. |
| 7,595,075 B2 | 9/2007 | Lang et al. |
| 7,629,005 B2 | 12/2009 | Popp et al. |
| 7,638,143 B2 | 12/2009 | Piene |
| 7,666,457 B1 | 2/2010 | Lang et al. |
| 7,695,528 B2 | 4/2010 | Lang et al. |
| 7,807,125 B2 | 10/2010 | Lang et al. |
| 7,850,988 B2 | 12/2010 | Lang et al. |
| 7,883,552 B2 | 2/2011 | Lang et al. |
| 8,440,236 B2 | 5/2013 | Lang et al. |
| 8,603,544 B2 | 12/2013 | Lang et al. |
| 8,609,140 B2 | 12/2013 | Lang et al. |
| 8,617,619 B2 | 12/2013 | Lang et al. |
| 8,663,706 B2 | 3/2014 | Lang et al. |
| 8,668,936 B2 | 3/2014 | Lang et al. |
| 8,709,499 B2 | 4/2014 | Lang et al. |
| 8,728,538 B2 | 5/2014 | Lang et al. |
| 2002/0044974 A1 | 4/2002 | Malcolm |
| 2004/0058995 A1 | 3/2004 | Shinohara et al. |
| 2004/0234443 A1* | 11/2004 | Chen et al. ............... 423/432 |
| 2004/0241303 A1 | 12/2004 | Levin et al. |
| 2005/0025811 A1* | 2/2005 | Levin et al. ............... 424/429 |
| 2005/0170049 A1 | 8/2005 | Dibble et al. |
| 2005/0244493 A1* | 11/2005 | Withiam et al. .......... 424/464 |
| 2006/0110452 A1* | 5/2006 | Dansereau et al. ....... 424/464 |
| 2006/0141126 A1 | 6/2006 | Levin et al. |
| 2006/0222737 A1 | 10/2006 | Dibble et al. |
| 2007/0026993 A1 | 2/2007 | Kawamoto et al. |
| 2007/0042039 A1 | 2/2007 | Lang et al. |
| 2007/0042082 A1 | 2/2007 | Lang et al. |
| 2007/0045890 A1 | 3/2007 | Lang et al. |
| 2007/0048406 A1 | 3/2007 | Lang et al. |
| 2007/0053977 A1 | 3/2007 | Lang et al. |
| 2007/0178153 A1 | 8/2007 | Levin et al. |
| 2007/0178154 A1 | 8/2007 | Levin et al. |
| 2007/0264329 A1* | 11/2007 | Stotler et al. ............. 424/464 |
| 2007/0264404 A1 | 11/2007 | Lang et al. |
| 2007/0269493 A1 | 11/2007 | Lang |
| 2007/0269558 A1 | 11/2007 | Lang |
| 2009/0022792 A1 | 1/2009 | Dittmar et al. |

OTHER PUBLICATIONS

Complaint for Patent Infringement, Civil Action No. 12-05378-ES-CLW, *Delavau, LLC* v. *J.M. Huber Corporation and J. M. Huber Micropowders Inc.*, filed Aug. 27, 2012 (6 pages).

Exhibit A to Complaint for Patent Infringement, Civil Action No. 12-05378-ES-CLW, *Delavau, LLC* v. *J.M. Huber Corporation and J.M. Huber Micropowders Inc.*, filed Aug. 27, 2012 (8 pages).

First Amended Complaint for Patent Infringement, Civil Action No. 12-05378-ES-CLW, *Delavau, LLC* v. *J.M. Huber Corporation and J.M. Huber Micropowders Inc.*, filed Nov. 19, 2012 (8 pages).

Exhibit A to First Amended Complaint for Patent Infringement, Civil Action No. 12-05378-ES-CLW, *Delavau, LLC* v. *J. M. Huber Corporation and J.M. Huber Micropowders Inc.*, filed Nov. 19, 2012 (8 pages).

Answer, Affirmative Defenses, and Counterclaims of Defendants J.M. Huber Corporation and J.M. Huber Micropowders, Inc. To Plaintiff'S Amended Complaint, Civil Action No. 12-05378-ES-CLW, *Delavau, LLC* v. *J.M. Huber Corporation and J.M. Huber Micropowders Inc.*, filed Dec. 13, 2012 (15 pages).

Answer to Counterclaim of Defendants J.M. Huber Corporation and J.M. Huber Micropowders Inc. By Delavau, LLC., Civil Action No. 12-05378-ES-CLW, *Delavau, LLC* v. *J.M. Huber Corporation and J.M. Huber Micropowders Inc.*, filed Jan. 7, 2013 (6 pages).

Amended Complaint (Second) against J.M. Huber Corporation, J.M. Huber Micropowders Inc., filed by Delavau, LLC. on Mar. 1, 2013, Civil Action No. 2:12-05378-ES-CLW (22 pages).

Answer to Amended Complaint, Counterclaim against Delavau, LLC by J.M. Huber Micropowders Inc., J.M. Huber Corporation, filed Mar. 15, 2013, Civil Action No. 2:12-05378-ES-CLW (29 pages).

Answer to Counterclaim by Delavau, LLC filed Apr. 8, 2013, Civil Action No. 2:12-05378-ES-CLW (9 pages).

Redacted Order and Opinion denying Plaintiffs Motion for Preliminary Injunction issued Aug. 26, 2013 and redacted Sep. 6, 2013, Civil Action No. 2:12-05378-ES-CLW (29 pages).

CalEssense 2000 Brochure (2000; publication month unknown).

HuberCal 2002 Brochure (2002; publication month unknown)).

Calci-Press MD 2002 Brochure, Internet Wayback Machine (Apr. 30, 2002).

Pformulate 2000 Entry for Maltodextrin, Internet Wayback Machine (Feb. 2002).

Calci-Press 2001 Brochure (Apr. 2001).

Leiner Health Products Inc., Active Natural Raw Material Specification, Calcium Carbonate Granulation (Mar. 2002).

Office Action in U.S. Appl. No. 13/755,077 dated May 3, 2013.

(56) References Cited

OTHER PUBLICATIONS

Office Action in U.S. Appl. No. 13/755,077 dated Sep. 18, 2013.
Office Action in U.S. Appl. No. 13/753,935 dated Apr. 23, 2013.
Notice of Allowance in U.S. Appl. No. 13/753,935 dated Sep. 13, 2013.
Office Action in U.S. Appl. No. 13/753,984 dated Apr. 11, 2013.
Office Action in U.S. Appl. No. 13/753,984 dated Jul. 23, 2013.
Notice of Allowance in U.S. Appl. No. 13/753,984 dated Oct. 1, 2013.
Office Action in U.S. Appl. No. 13/451,560 dated Sep. 10, 2013.
2nd Notice of Allowance in U.S. Appl. No. 13/753,935 dated Nov. 12, 2013.
Notice of Allowance in U.S. Appl. No. 13/755,077 dated Nov. 1, 2013.
Office Action in U.S. Appl. No. 13/571,079 dated Jun. 11, 2013.
Carrier Vibrating Equipment, Inc—Fluid Vibrating Bed Systems, No. 16510, (1992).
Convection. (n.d.). The American Heritage Dictionary of the English Language, Fourth Edition, Retrieved Jun. 30, 2009 from Dictionary.com website: <http://dictionary.reference.com/browse/convection.>
Office Action in U.S. Appl. No. 13/447,949 dated Apr. 29, 2014.
Office Acion in U.S. Appl. No. 13/571,637 dated Jul. 12, 2013.
Office Action in U.S. Appl. No. 13/451,547 dated Jan. 15, 2014.
Office Action in U.S. Appl. No. 13/451,548 dated Jan. 14, 2014.
Office Action in U.S. Appl. No. 13/451,550 dated Nov. 29, 2013.
Office Action in U.S. Appl. No. 13/451,555 dated Oct. 10, 2013.
Office Action in U.S. Appl. No. 13/451,558 dated Aug. 13, 2013.
Office Action in U.S. Appl. No. 13/571,079 dated Jan. 13, 2014.
Office Action in U.S. Appl. No. 14/155,893 dated Mar. 13, 2014.
Office Action in U.S. Appl. No. 13/451,550 dated Apr. 14, 2014.
Office Action in U.S. Appl. No. 13/451,554 dated May 27, 2014.
Office Action in U.S. Appl. No. 13/451,561 dated May 30, 2014.
Patent Board Decision in U.S. Appl. No. 11/522,901 (now Pat. No. 8,440,236) dated Feb. 28, 2013.
Database Internet, Data Sheet from 1-3, "Ground Calcium Carbonate," XP002483143, retrieved from Web-Archiv, <<http://web.archive.org/web/20020427071605/http://www.exportjamaica.org/jetco/click.htm>>, Apr. 27, 2002.
Docket for Civil Action 12-05378-ES-CLW, *Delavau, LLC v. J.M. Huber Corporation and J.M. Huber Micropowders Inc.*, filed Aug. 27, 2012, in the United States District court for the District of New Jersey (7 pages).
Docket for Civil Action No. 2:12-05378-ES-CLW, *Delavau, LLC v. J.M. Huber Corporation and J.M. Huber Micropowders Inc.*, filed Aug. 27, 2012, in the United States District Court for the District of New Jersey, obtained Sep. 13, 2013 (17 pages).
Docket for Civil Action No. 2:12-05378-ES-CLW, *Delavau, LLC v. J.M. Huber Corporation and J.M. Huber Micropowders Inc.*, filed Aug. 27, 2012, in the United States District Court for the District of New Jersey, obtained Feb. 28, 2014 (23 pages).
Gennaro, Alfonso R., Remington: The Science and Practice of Pharmacy, vol. 2, 1615-1649 (19th ed.), 1995.
Bliziotes et al., "Absent Intestinal Response to Calciferols in Hereditary Resistance to 1,25-Dihydroxyvitamin D: Documentation and Effective Therapy with High Dose Intravenous Calcium Infusions," The Journal of Clinical Endocrinology & Metabolism, 66(2), pp. 294-300, Feb. 1988.
Bronner, Erratum, The American Journal of Clinical Nutrition, 57(3), p. 451, Mar. 1993.
Bronner et al., "An Analysis of Intestinal Calcium Transport Across the Rat Intestine", American Physiological Society, pp. G561-G569, May 1986.
Bronner, "Net Calcium Absorption in Premature Infants: Results of 103 Metabolic Balance Studies," Am. J. Clin. Nutr., vol. 56, pp. 1037-1044, 1992.
Bronner et al., "Nutritional Aspects of Calcium Absorption," Recent Advance in Nutritional Science, pp. 9-12, 1998.

Bronner, "The Role of Passive Transport in Calcium Absorption," American Society for Nutritional Sciences, p. 1426, 2003.
Bowen, "Particle Size Distribution Measurement from Millimeters to Nanometers and from Rods to Platelets," Journal of Dispersion Science and Technology, 23(5), pp. 631-662 (2002).
Cai et al., "Calcium Bioavailability and Kinetics of Calcium Ascorbae and Calcium Acetate in Rats," Society for Experimental Biology and Medicine, pp. 40-45 (2004).
Declaration under 37 C.F.R. 1.132 of Dr. Kevin Lang dated Mar. 10, 2010.
"Effect of Calcium Supplement Particle Size and Vitamin D Supplement on Calcium Retention in Adolescent Girls," Clinical Trials. gov, http:clinicaltrials.gov/ct2/show/NCT01005381, Oct. 30, 2009.
Eible, "Effect of Calcium Carbonate Particle Size on Calcium Retention in Adolescent Girls," Purdue University Graduate School Thesis, Oct. 2007.
Florence et al., "Factors Affecting the Oral Uptake and Translocation of Polystyrene Nanoparticles: Histological and Analytical Evidence," J. Drug Target, 3(1), pp. 65-70, 1995, abstract only.
Guinotte et al., "The Effects of Particle Size and Origin of Calcium Carbonate on Performance and Ossification Characteristics in Broiler Chicks," Poult. Sci., 70(9), pp. 1908-1920, Sep. 1992, Abstract only.
Heaney et al., "Absorption of Calcium as the Carbonate ad Citrate Salts, with Some Observations on Method," Osteoporos. Int., 9(1), pp. 19-23, 1999, Abstract only.
Ireland et al., "Effect of Dietary Calcium and Age on Jejunal Calcium Absorption in Humans Studied by Intestinal Perfusion," The Journal of Clinical Investigation, vol. 52, pp. 2672-2681, Nov. 1973.
Lengemann et al., "Studies on the Enhancement of Radiocalcium and Radiostrontium Absorption by Lactose in the Rat," The Journal of Nutrition, vol. 68, pp. 443-456 (1959).
Li et al., "Normalization of Mineral Ion Homeostasis by Dietary Means Prevents Hyperparathyroidism, Rickets, and Osteomalacia, But Not Alopecia in Vitamin D Receptor-Ablated Mice," Endocrinology, 139(10), pp. 4391-4396 (1998).
Lichonvnikova, "The Effect of Dietary Calcium Source, Concentration and Paticle Size on Calcium Retention, Effshell Quality and Overall Calcium Requirement in Laying Hens," Br. Poult. Sci., 481(1), pp. 71-75, Feb. 2007, Abstract only.
McCormick, "Passive Diffusion Does Not Play a Major Role in the Absorption of Dietary Calcium in Normal Adults," American Society for Nutritional Sciences, pp. 3428-3430 (2002).
Micro Powders and Braig Inc., "Process Description—Micro Powders & Braig Contiuous Granulation." May 30, 2002.
OMYA-CAL FG-15AZ Specification Production, Nov. 2, 2001, <http:/www.ccicalifornia.com/df/calciumcarb/fg15_specs.pdf>.
OMYA-CAL FG-10 AZ, Product Data Sheet, OMYA Arizona, Inc., Apr. 11, 2003.
OMYA-CAL USP-10 AZ, Product Data Sheet, OMYA Arizona, Inc., Feb. 12, 2004.
Pansu et al., "Developmental Changes in the Mechanisms of Duodenal Calcium Transport in the Rat," American Journal of Physiology, 244(1), G20-G26, Jan. 1983.
Pansu et al., "Duodenal and Ileal Calcium Absorption in the Rat and Effects of Vitamin D," American Journal of Physiology, 244(6), pp. G695-G700, Jun. 1983.
Pansu et al., "Effect of Ca Intake on Saturable and Nonsaturable Components of Duodenal Ca Transport," 240(1), pp. G32-G37, Jan. 1981.
Pansu et al., "Solubility and Intestinal Transit Time Limit Calcium Abosprtion in Rats," The Journal of Nutrition, 123 (8), pp. 1396-1404, (1993).
Rao et al., "Influence of Dietary Calcium Level and Particle Size of Calcium Source on In Vivo Calcium Solubilization by Commerical Leghorns," Poult. Sci., 68(11), pp. 1499-1505 (1989) abstract only.
Rao et al., "In Vivo Limestone Solubilization in Commerical Leghorns: Role of Dietary Calcium Level, Limestone, Particle Size, In Vitro Limestone Solubility Rate, and the Calcium Status of the Hen," Poult. Sci., 69(12), pp. 2170-2176 (1990) Abstract only.

(56) References Cited

OTHER PUBLICATIONS

Shahnazari et al., "Diet Calcium Level but Not Calcium Supplement Particle Size Affects Bone Density and Mechanical Properties in Ovariectomized Rats," The Journal of Nutrition, Nutrient Physiology, Metabolism, and Nutrient-Nutrient Interactions, pp. 1308-1314 (2009).

Sheikh et al., "Role of Vitamin D-dependent and Vitamin D-independent Mechanisms in Absorption of Food Calcium," J. Clin. Invest., vol. 81, pp. 126-132, Jan. 1988.

Slepchenko et al., "Modeling of Transcellular Ca Transport in Rat Duodenum Points to Coexistence of Two Mechanisms of Apical Entry," Am. J. Physiol. Cell Physiol. pp. C270-C281 (2001).

Weaver, Connie, "Prepuberty and Adolescence," Calcium in Human Health, Chapter 17, pp. 281-296 (2006).

Weinstein et al., "Bone Histomorphometry in Vitamin D-Deficient Rats Infused with Calcium and Phosphorus," The American Journal of Physiology, 246(6), pp. E399-E505, Jun. 1984.

Wilz et al., Plasma 1,25-(OH)2-vitamin D Concentrations and Net Intestinal Calcium, Phosphate, and Magnesium Absorption in Humans1-3, American Journal of Clinical Nutrition, 32(10), pp. 2052-2060, Oct. 1979.

Win, "Effects of Particle Size and Surface Coating on Cellular Uptake of Polymeric Nanoparticles for Oral Delivery of Anticancer Drugs," Biomaterials, 26(15), pp. 2713-2722, May 2005, Abstract only.

Zafar et al., "Nondigestable Oligosaccharides Increase Calcium Absorption and Suppress Bone Resorption in Ovariectomized Rats," The Journal of Nutrition, pp. 399-402, (2004).

Pformulate Excipients—Calcium Carbonate, XP003027983, 2000, http://www.pformulate.com/calcarb.htm.

Redacted Brief in Opposition to Motion for Reconsideration by J.M. Huber Corporation, J.M. Huber Micropowders Inc filed Sep. 23, 2013 and redacted Sep. 26, 2013, Civil Action No. 2:12-05378-ES-CLW (16 pages).

Redacted Motion for Reconsideration re Order on Motion for Preliminary Injunction by Delavau LLC filed Sep. 6, 2013 and redacted Dec. 12, 2013, Civil Action No. 2:12-05378-ES-CLW (17 pages).

Badawy et al., "Effect of Process Parameters on Compressibility of Granulation Manufactured in a High-Shear Mixer." Internation Journal of Pharmaceutics 198(2000) 51-61.

Bandelin, Fred J., "Compressed Tablets by Wet Granulation." In Pharmaceutical Dosage Forms: Tablets vol. 1, edited by Herbert A. Lieberman, Leon Lachman, and Joseph B. Schwartz, 131-193. New York: Marcel Dekker, Inc., 1989.

Connolly, Robert J., Frank A. Berstler and David Coffin-Beach, "Tablet Production." In Pharmaceutical Dosage Forms: Tablets vol. 3, edited by Herbert A. Lieberman, Leon Lachman, and Joseph B. Schwartz, 369-416. New York: Marcel Dekker, Inc., 1990.

Danielsen, S. and S. Hovmand, "Drying of Granulated Product in a Vibrated Fluid Bed." In Drying '80 vol. 1: Developments in Drying, edited by Arun S. Mujumdar, 194-199. Hemisphere Publishing Corporation, 1980.

Elsabbagh, Hassan M., Abdel-Halim H. Ghanem and Hamdy M. Abdel-Alim, "The Influence of Binder Type and Concentration on the Physical Characteristics of Calcium Carbonate Granules and Their Corresponding Tablets." Department of Pharmaceutics, Faculty of Pharmacy, Mansoura University, Mansoura, A.R.E, Received Feb. 18, 1980.

Faure et al., "Applicability of a Scale-Up Methodology for Wet Granulation Processes in Collette Gral High Shear Mixer-Granulators." European Journal of Pharmaceutical Sciences 8(1999): 85-93.

Faure, A., P. York and R.C. Rowe, "Process Control and Scale-Up of Pharmaceutical Wet Granulation Processes: A Review." European Journal of Pharmaceutics and Biopharmaceutics 52(2001): 269-277.

Fausett, Hector, Charles Gayser Jr. and Alekha K. Dash, "Evaluation of Quick Disintegrating Calcium Carbonate Tablets." AAPS PharmSciTech, 2000; 1 (3) article 20. http://www.pharmscitech.com.

Foster, J.C., "Granulation & Tabletting Tutorial." Specialt Minerals. Jul. 17, 2001.

Gao et al., "Fluit Bed Granulation of a Poorly Water Soluble, Low Density, Micronized Drug: Comparison with High Shear Granulation." International Journal of Pharmaceutics 237(2002) 1-14.

Gordon et al., "Granulation Technology and Tablet Characterization." In Pharmaceutical Dosage Forms: Tablets vol. 2, edited by Herbert A. Lieberman, Leon Lachman, and Joseph B. Schwartz, 245-348. New York: Marcel Dekker, Inc., 1990.

Gupta, C.K. and D. Sathiyamoorthy, Fluid Bed Technology in Materials Processing, Boca Raton, Florida: CRC Press LLC., 1999. pp. 12-17, 127-131 and 138-143.

Handbook of Pharmaceutical Granulation Technology, edited by Dilip M. Parikh, 496-497. New York: Marcel Dekker, Inc., 1997.

Hoornaert et al., "Agglomeration Behaviour of Powders in a Lodige Mixer Granulator." Powder Technology 96(1998) 116-128.

Hovmand, Svend, "Fluidized Bed Drying." In Handbook of Industrial Drying vol. 1, edited by Arun S. Mujumdar, 195-248. New York: Marcel Dekker, Inc., 1995.

HuberCal® CCG41XX FG Product Specifications. J.M. Huber Corporation. Mar. 22, 2005.

Jarowski, Charles I., "The Pharmaceutical Pilot Plant." In Pharmaceutical Dosage Forms: Tablets vol. 3, edited by Herbert A. Lieberman, Leon Lachman, and Joseph B. Schwartz, 303-367. New York: Marcel Dekker, Inc., 1990.

Johansson, Barbro and Goran Alderborn, "The Effect of Shape and Porosity on the Compression Behaviour and Tablet Forming Ability of Granular Materials Formed from Microcrystalline Cellulose." European Journal of Pharmaceutics and Biopharmaceutics 52(2001): 347-357.

Keey, R. B., Drying of Loose and Particulate Materials. Hemisphere Publishing Corporation, 1992. pp. 20-25, 96-97, and 299-305.

Knight et al., "An Investigation into the Kinetics of Liquid Distribution and Growth in High Shear Mixer Agglomeration." Powder Technology 97 (1998) 246-257.

Kristensen, Henning G., "Particle Agglomeration in High Shear Mixers." Powder Technology 88(1996): 197-202.

Lantz Jr., Russell J. and Joseph B. Schwartz, "Mixing." In Pharmaceutical Dosage Forms: Tablets vol. 2, edited by Herbert A. Lieberman, Leon Lachman, and Joseph B. Schwartz, 1-71. New York: Marcel Dekker, Inc., 1990.

Leuenberger, Hans, "New Trends in the Production of Pharmaceutical Granules: Batch Versus Continuous Processing." European Journal of Pharmaceutics and Biopharmaceutics 52(2001) 289-296.

Leuenberger, Hans, "Scale-Up in the Field of Granulation and Drying." In Pharmaceutical Process Scale-Up, edited by Michael Levin, 151-170. New York: Marcel Dekker, Inc., 2002.

Lewis, A. and G. Simpkin, "Tabletting—An Industrial Viewpoint." In Powder Technology and Pharmaceutical Processes, edited by D. Chulia, M. Deleuil and Y. Pourcelot, 473-492. The Netherlands: Elsevier Science B.V., 1994.

Lieberman, Herbert A. and Albert Rankell, "Drying" In The Theory and Practice of Industrial Pharmacy, edited by Leon Lachman, Herbert A. Lieberman and Joshep L. Kanig, 22-48. Philadelphia: Lea & Febiger, 1970.

Mackaplow, Michael B., Lawrence A. Rosen and James N. Michaels, "Effect of Primary Particle Size on Granule Growth and Endpoint Determination in High-Shear Wet Granulation." Powder Technology 108(2000) 32-45.

Micro Powders and Braig Inc., Apr. 4, 2001.

Mujumdar, Arun S., "Drying in Mineral Processing." In Handbook of Industrial Drying vol. 2, edited by Arun S. Mujumdar, 921-929. New York: Marcel Dekker, Inc., 1995.

Mujumdar, Arun S. and Anilkumar S. Menon, "Drying of Solids: Principles, Classification, and Selection of Dryers." In Handbook of Industrial Drying vol. 1, edited by Arun S. Mujumdar, 1-39. New York: Marcel Dekker, Inc., 1995.

Mujumdar, Arun S. and Bing Huang, "Impingement Drying." In Handbook of Industrial Drying vol. 1, edited by Arun S. Mujumdar, 489-501. New York: Marcel Dekker, Inc., 1995.

(56) References Cited

OTHER PUBLICATIONS

Mujumdar, A.S., "Recent Development in the Drying Technologies for the Production of Particulate Materials." In Handbook of Conveying and Handling of Particulate Solids, edited by A. Levy and H. Kalman, 533-545. Elsevier Science B.V., 2001.

OMYA-CAL FG-15 AZ. OMYA Arizona, Inc., Nov. 2, 2001.

Pakowski, Zdzislaw and Arun S. Mujumdar, "Drying of Pharmaceutical Products." In Handbook of Industrial Drying vol. 2, edited by Arun S. Mujumdar, 743-773. New York: Marcel Dekker, Inc., 1995.

Peck, Garnet E., Neil R. Anderson and Gilbert S. Banker, "Principles of Improved Tablet Production System Design." In Pharmaceutical Dosage Forms: Tablets vol. 3, edited by Herbert A. Lieberman, Leon Lachman, and Joseph B. Schwartz, 1-76. New York: Marcel Dekker, Inc., 1990.

Peck, Garnet, "Principles of Tablet Granulation." Presented at: Effective Techniques for Tablet Manufacturing, Key Biscayne, Florida, Feb. 6-8, 1990.

Peck et al., "Tablet Formulation and Design." In Pharmaceutical Dosage Forms: Tablets vol. 1, edited by Herbert A. Lieberman, Leon Lachman, and Joseph B. Schwartz, 75-130. New York: Marcel Dekker, Inc., 1989.

Pformulate. "Excipients Calcium Carbonate." http://web.archive.org/web/20030404161259/www.pformulate.com/calcarb.htm.

Rudnic, Edward, "Oral Solid Dosage Forms." In Remington: The Science and Practice of Pharmacy, edited by Alfonso R. Gennaro, 1615-1649. Easton, Pennsylvania: Mack Publishing Company, 1995.

Schwartz, Joseph B., "Scale-Up of the Compaction and Tableting Process." In Pharmaceutical Process Scale-Up, edited by Michael Levin, 221-237. New York: Marcel Dekker, Inc., 2002.

Shangraw Ralph F., "Compressed Tablets by Direct Compression." In Pharmaceutical Dosage Forms: Tablets vol. 1, edited by Herbert A. Lieberman, Leon Lachman, and Joseph B. Schwartz, 195-246. New York: Marcel Dekker, Inc., 1989.

Solgar Questionnaire, Jul. 31, 2002.

Strathy, Walter A. and Adolfo L. Gomez, "Practical Aspects of Tableting Scale-Up." In Pharmaceutical Process Scale-Up, edited by Michael Levin, 239-250. New York: Marcel Dekker, Inc., 2002.

Valazza, Michael, Preparing Granulations for Compression. Presented at: Tablet Manufacturing Technology 2000, Apr. 11-13, 2000, Atlantic City, New Jersey.

Van Scoik, Kurt G., Michael A. Zoglio and Jens T. Carstensen, "Drying." In Pharmaceutical Dosage Forms: Tablets vol. 2, edited by Herbert A. Lieberman, Leon Lachman, and Joseph B. Schwartz, 73-105. New York: Marcel Dekker, Inc., 1990.

Weinekotter, Ralf and Hermann Gericke, Mixing of Solids, The Netherlands: Kluwer Academic Publishers, 2000. pp. 102-105.

\* cited by examiner

CALCIUM SUPPLEMENT HAVING ENHANCED ABSORPTION

This application is a Continuation Application under 35 U.S.C §120 of U.S. application Ser. No. 11/855,807, filed Sep. 14, 2007, which claims priority to U.S. Provisional Application No. 60/892,183, filed Feb. 28, 2007 and 60/825,853, filed Sep. 15, 2006, each of which are incorporated by reference herein in their entirety.

FIELD OF INVENTION

The present invention relates generally to compositions and methods for dietary calcium supplementation. More particularly, the present invention relates to forms of calcium carbonate which provide enhanced absorption.

BACKGROUND OF THE INVENTION

Calcium is an essential nutrient and the most abundant mineral in the human body. Calcium plays a vital role in building healthy teeth and bones, blood clotting, muscle contraction, and nerve function. Most notably, calcium reduces the risk of bone loss caused by osteoporosis in both men and women. Despite these advantages, it has been estimated that half of all Americans do not consume sufficient amounts of calcium. More troubling, 80% of women, the group at highest risk for developing osteoporosis, do not consume enough calcium.

This deficiency is due in part to the large daily intake of calcium that is suggested by physicians. The National Academy of Sciences, Institute of Medicine recommends daily intakes (RDI) of 1,200 mg of elemental calcium per day for people over 50 years of age and 1,300 mg a day for people under 19 years of age. For individuals between these age groups, the recommendation is 1,000 mg per day. Not surprisingly, physicians recommend calcium supplements more than any other dietary supplement.

Commercially available calcium supplements employ a wide variety of calcium salts, including, for example, calcium carbonate, calcium citrate, calcium glycerophosphate, calcium oxide, calcium phosphate, calcium pyrophosphate, calcium chloride, calcium lactate, and calcium sulfate. Despite the very different solubilities of these salts, their absorption in the intestine is comparable. For example, while calcium carbonate is insoluble in water and calcium citrate is soluble, isotopic tracer methods have established that their bioavailability is similar. In view of the similar bioavailability of various calcium salts, calcium carbonate has become the most common salt for supplementation because it is comparably inexpensive and delivers more elemental calcium on a weight basis (~40%) than most other calcium salts. However, the absorption of calcium carbonate through the intestine, like all calcium salts, is relatively inefficient. For example, it has been reported that calcium carbonate absorption efficiency is about 34.2%±10.1% in adult men and postmenopausal women. See Heaney, R. P. et al., "Absorption of calcium as the carbonate and citrate salts, with some observations on method." *Osteoporos. Int.* 9:19-23 (1999).

Vitamin D is known to be a beneficial adjunct to calcium supplementation because it both increases absorption efficiency up to a serum 25-OH vitamin D level of 80 nmol/ml and regulates parathyroid hormone levels which in turn regulate bone absorption/resorption of calcium. The amino acid L-lysine has also been reported to enhance calcium absorption efficiency in humans and rats. See Civitelli et al. "Dietary L-lysine and calcium metabolism in humans," Nutrition 8: 400-5 (1992); Wasserman et al. "Interrelated effects of L-lysine and other dietary factors on the gastrointestinal absorption of Calcium 45 in the Rat and Chick." *J. Nutrition* 62, 367-376 (1957). However, the efficacy of L-lysine supplementation has not been established in chronic feeding. Despite the benefits of calcium supplements, particularly those fortified with Vitamin D, it would be desirable to provide a form of calcium for use in calcium supplements and food products having improved absorption characteristics.

It is known in the pharmaceutical industry that an important factor which effects the bioavailability of a drug is particle size. There is generally an inverse relationship between the particle size of nonionized particles and absorption through the gut. See Florence et al., "Factors Affecting the Oral Uptake and Translocation of Polystyrene Nanoparticles: Histological and Analytical Evidence," *J. Drug Target* 3, 65-70 (1995). A recent in vitro study showed cellular uptake was greater for polystyrene particles in the 100-200 nm size range than for similar smaller or larger particles. Win et al. "Effects of Particle Size and Surface Coating on Cellular Uptake of Polymeric Nanoparticles for Oral Delivery of Anticancer Drugs," *Biomaterials* 26, 2713-22 (2005).

However, The effect of particle size on calcium absorption has received only modest attention to date. Rao et at studied the effect of limestone calcium carbonate particle size on in vivo solubilization and retention in hens. See K. S. Rao et al., "In Vivo Limstone Solubilization in Commercial Leghorns: Role of Dietary Calcium Level, Limestone Particle Size, In Vitro Limestone Solubility Rate, and the Calcium Status of the Hen," *Poultry Sci.,* 69:2170-2176 (1990). The authors report that hens consuming calcium carbonate of particle size between 2 and 5 mm (millimeters) solubilize and retain a greater percentage of calcium than hens fed calcium carbonate of particle size between 0.5 and 0.8 millimeters. The authors state that this is consistent with their earlier finding that hens fed large particulate limestone retain a greater percentage of calcium than hens fed small particulate limestone, Rao et al, "Influence of Dietary Calcium Level and Particle Size of Calcium Source on In Vivo Calcium Solubilization by Commercial Leghorns," *Poultry Sci.* 68:1499-1505 (1989). It is suggested that greater utilization of large particles of calcium carbonate as compared to small particles results from an increased residence time in the gizzard which provides for gradual metering through the intestine, as previously posited by Scott et al, "The Calcium Requirements of Laying Hens and Effects of Dietary Oyster Shell Upon Eggshell Quality," *Poultry Sci.* 50:1055-1063 (1971). In contrast, Guinotte and coworkers report that ground calcium carbonate having a particle size less than 0.15 mm improved calcium retention and tibial ossification in growing chicks as compared to medium (0.3 to 1.18 mm) and large (1.18 to 4.75 mm) calcium carbonate particles. See F. Guinotte et al., "The Effects of Particle Size and Origin of Calcium Carbonate on Performance and Ossification Characteristics in Broiler Chicks," Poultry Sci., 70:1908-1920 (1991). Similar studies on particle size and absorption in humans or rodents are lacking.

There is continuing need in the art for calcium forms having high in vivo utilization efficiency. It therefore is an object of the present invention to identify critical parameters of calcium carbonate powders which provide for enhanced bioavailability and to provide such powders. It is another object of the present invention to provide dietary supplements, foods and the like comprising highly absorbable calcium forms. It is also an object of the invention to provides compositions and methods for increasing calcium balance. It is further an object of the invention to provide composition and methods for preventing, treating, and/or ameliorating the effects of osteoporosis with calcium supplements, ideally without resort to pharmaceutical intervention.

SUMMARY OF THE INVENTION

In accordance with the foregoing objectives and others, the present invention provides calcium carbonate powders, and supplements, foods, and the like comprising such powders, which exhibit unexpectedly high absorption efficiency, calcium balance, and bone strength.

In one aspect of the invention, a tablet for dietary calcium supplementation is provided comprising between about 1,600 and about 2,500 mg of enhanced absorption calcium carbonate powder. In a variant of this aspect, the tablet comprises between about 1,798 mg and about 1,888 mg of enhanced absorption calcium carbonate. The tablet according to this aspect of the invention typically has a volume between about 0.75 cm$^3$ and about 1.6 cm$^3$, more typically between about 0.90 cm$^3$ and about 1.1 cm$^3$, and in one embodiment has a volume of about 1 cm$^3$. The tablet may further comprise at least about 400 I.U. of vitamin D and is preferably capable of providing at least about 360 mg of absorbable elemental calcium. The enhanced absorption calcium carbonate according to this and the following aspects of the invention may have a particle size distribution characterized, for example, by a $D_{50}$ value, on a volume basis, between about 9.8 µm and about 13.5 µm, a $D_{90}$ value, on a volume basis, between about 26.1 µm and about 31.7 µm, and at least 30% of total volume of particles having sizes between about 1 µm and about 11 µm.

According to another aspect, a tablet for dietary calcium supplementation is provided comprising: (i) between about 1,798 and about 1,888 mg of calcium carbonate powder having the particle size distribution of FIG. 12; and (ii) at least about 400 I.U. of vitamin D; and wherein the volume of the tablet is between about 0.90 cm$^3$ and about 1.1 cm$^3$.

In another aspect, a tablet for dietary calcium supplementation comprises between about 800 mg and about 1,400 mg of enhanced absorption calcium carbonate powder, and will more typically comprise between about 899 mg and about 944 mg of said calcium carbonate. The tablet according to this aspect may have a volume between about 0.4 cm$^3$ and about 0.8 cm$^3$, or between about 0.4 cm$^3$ and about 0.6 cm$^3$, or may have a volume of about 0.5 cm$^3$. The tablet may further comprise at least about 400 I.U. of vitamin D and preferably is capable of providing at least about 180 mg of absorbable elemental calcium.

In a related aspect, a tablet for dietary calcium supplementation is provided comprising: (i) between about 899 mg and about 944 mg of calcium carbonate having the particle size distribution of FIG. 12; and (ii) at least about 400 I.U. of vitamin D; wherein the volume of said tablet is between about 0.4 cm$^3$ and about 0.6 cm$^3$.

In another aspect of the invention, a tablet for dietary calcium supplementation comprises between about 1,750 and about 3,000 mg of enhanced absorption calcium carbonate powder and more typically will comprise between about 1,948 mg and about 2,046 mg of enhanced absorption calcium carbonate. The tablet may have a volume between about 0.8 cm$^3$ and about 1.75 cm$^3$, more typically, between about 1 cm$^3$ and about 1.2 cm$^3$, or about 1.1 cm$^3$. The tablet may further comprise at least about 400 I.U. of vitamin D and will preferably provide at least about 390 mg of absorbable elemental calcium.

In one aspect related to the preceding aspect, a tablet for dietary calcium supplementation comprises: (i) between about 1,948 mg and about 2,046 mg of calcium carbonate having the particle size distribution of FIG. 12; and (ii) at least about 400 I.U. of vitamin D; wherein the volume of the tablet is between about 1 cm$^3$ and about 1.2 cm$^3$.

In a further aspect of the invention, a tablet for dietary calcium supplementation is provided comprising between about 925 mg and about 1,200 mg of enhanced absorption calcium carbonate or between about 974 mg and about 1,023 mg of enhanced absorption calcium carbonate. The tablet may have a volume between about 0.45 cm$^3$ and about 0.8 cm$^3$, and more typically will have a volume between about 0.5 cm$^3$ and about 0.7 cm$^3$, including for example, a volume between about 0.55 cm$^3$ and about 0.6 cm$^3$. The tablet may further comprise at least about 400 I.U. of vitamin D and is preferably capable of providing at least about 195 mg of absorbable elemental calcium.

Another aspect of the invention is a tablet for dietary calcium supplementation comprising: (i) between about 974 mg and about 1,023 mg of calcium carbonate having the particle size distribution of FIG. 12; and (ii) at least about 400 I.U. of vitamin D; wherein the volume of said tablet is between about 0.5 cm$^3$ and about 0.7 cm$^3$.

In yet another aspect, various methods are provided, including methods for providing the daily Adequate Intake (AI) of 1,200 or 1,300 mg of elemental calcium comprising either (1) administering to an individual in need thereof, a tablet comprising enhanced absorption calcium carbonate once during the course of a day; or (2) administering to an individual in need thereof, two tablets comprising enhanced absorption calcium carbonate either together or at two times during the course of a day.

In still a further aspect of the invention, a tablet for dietary calcium supplementation is provided comprising: (i) between about 1,425 and about 1,575 mg of enhanced absorption calcium carbonate powder; and (2) at least about 500 I.U. of vitamin D, at least about 600 I.U. of vitamin D, at least about 800 I.U. of vitamin D, or at least about 1,000 I.U. of vitamin D.

In another aspect, a product is provided comprising: (a) a container comprising a plurality of tablets for dietary calcium supplementation, the tablets comprising between about 1,425 and about 1,575 mg of enhanced absorption calcium carbonate powder and vitamin D; and (b) instructions on the product labeling, packaging, or insert, for the use of the tablets in a single daily dose to achieve a full day requirement of calcium. This aspect applies equally to any of the tablets describes above.

Another aspect relates to method a for providing the daily Adequate Intake (AI) of 1,000 mg of elemental calcium comprising administering to an individual in need thereof, once during the course of a day for a period of at least about eight weeks, a tablet comprising between about 1,425 and about 1,575 mg of enhanced absorption calcium carbonate powder and at least about 400 I.U. of vitamin D.

Yet another aspect relates to a method comprising: (i) providing a brand of calcium supplements in tablet form, said brand of calcium supplements comprising a first calcium carbonate powder; and (2) reformulating said brand of calcium supplements by replacing all or a portion of said first calcium carbonate powder in said calcium supplements with enhanced absorption calcium carbonate powder having an absorption efficiency of elemental calcium greater than that of said first calcium carbonate powder.

Functional foods and confectionary products comprising enhanced absorption calcium carbonate powder and optionally, vitamin D, are also provided.

Pharmaceutical compositions are also provided, which may comprise, for example: (1) calcium carbonate powder having a particle size distribution characterized by a $D_{50}$ value, on a volume basis, between about 9.8 µm and about 13.5 µm, a $D_{90}$ value, on a volume basis, between about 26.1 µm and about 31.7 µm, and at least 30% of total volume of particles having sizes between about 1 µm and about 11 µm; and (2) at least about 400 I.U. of vitamin D.; and (3) a bisphosphonate drug.

In an additional aspect of the invention, a multi-vitamin is provided comprising:
(1) enhanced absorption calcium carbonate powder;
(2) one or more vitamins selected from the group consisting of:
   between 1 and about 35,000 IU of vitamin A;
   between 1 and about 1,000 mg of vitamin C;
   between 1 and about 4,000 IU of vitamin D;
   between 1 and about 450 IU of vitamin E;
   between 1 and about 250 mcg of vitamin K;
   between 1 and about 15 mg of vitamin B-1 (thiamin);
   between 1 and about 17 mg of vitamin B-2 (riboflavin);
   between 1 and about 200 mg of vitamin B-3 (niacin);
   between 1 and about 100 mg of vitamin B-5 (pantothenic acid);
   between 1 and about 30 mg of vitamin B-6 (pyridoxine);
   between 1 and about 4,000 mcg of vitamin B-9 (folic acid);
   between 1 and about 250 mcg of vitamin B-12 (cobalamin); and
   between 1 and about 1,000 mcg of vitamin H (biotin); and combinations thereof; and
(3) one or more minerals selected from the group consisting of:
   between 1 and about 180 mg of iron;
   between 1 and about 1,100 mg of phosphorous;
   between 1 and about 1,500 mcg of iodine;
   between 1 and about 4,000 mg of magnesium;
   between 1 and about 150 mg of zinc;
   between 1 and about 600 mcg of selenium;
   between 1 and about 20 mg of copper;
   between 1 and about 20 mg of manganese;
   between 1 and about 2,000 mcg of chromium; and
   between 1 and about 750 mcg of molybdenum;
   between 0.001 and about 0.1 mg of tin;
   between 1 and about 100 mcg of vanadium;
   between 0.5 and 50 mcg of nickel;
   and combinations thereof.

In yet another aspect of the invention, a calcium dietary supplement tablet is provided. The supplement tablet may comprise about 1,500 mg of precipitated calcium carbonate powder and may have a volume from about 0.75 to about 1 ml.

These and other aspects of the invention may be more clearly understood by reference to the following detailed description of the invention and the appended claims.

DETAILED DESCRIPTION OF THE INVENTION

In the following description of the invention, it is to be understood that the terms used have their ordinary and accustomed meanings in the art, unless otherwise specified. Reference to particle size herein will be understood to refer to particle diameter, unless otherwise specified. Reference to particle size distributions herein will be understood to refer to the distributions (or histograms) of the particles on a volume basis, unless otherwise specified. It is within the skill in the art to convert the volume distributions to weight or number distributions, if so desired. Reference to recommended daily intakes (DRIs) or adequate intakes (AIs) of calcium or other daily calcium doses specified herein, will be understood to refer to the amount of elemental calcium (as opposed to the amount of calcium carbonate), unless otherwise specified. "Elemental calcium" refers to the element Ca, in any oxidation state. Where a particle size is prefaced by the term "about," it will be understood to include particle sizes which are within the range of error typically associate with the measurement of particle size using the techniques described herein.

By "enhanced absorption calcium carbonate" is meant a calcium carbonate powder having an absorption efficiency of elemental calcium greater than the absorption efficiency of elemental calcium from a conventional calcium carbonate powder. By "conventional calcium carbonate powder" is meant calcium carbonate powder from which about 30% of the elemental calcium is absorbed in adults, and on which the daily adequate intakes (AIs) of 1,000 mg and 1,200 mg, set by the Institute of Medicine of the National Academy of Sciences, are based. Conventional calcium carbonate includes the calcium carbonate powder OMYA-Cal® USP-15-AZ (Omya, Inc.) described herein. In various embodiments, enhanced absorption calcium carbonate will have an absorption efficiency at least 5% greater, at least 7.5% greater, at least 10% greater, at least 12.5% greater, at least 15% greater, or at least 20% greater than conventional calcium carbonate. Put another way, the absorption efficiency of enhanced absorption calcium carbonate in adults will be at least about 35%, at least about 37.5%, at least about 40%, at least about 45%, or at least about 50%.

As used herein, the term "vitamin D" refers to broadly to vitamin D or any metabolite thereof, including without limitation, calciferol ($D_2$), cholecalciferol ($D_3$), calcidiol (25-hydroxy-vitamin D), calcitriol (1,25 dihydroxy vitamin $D_3$), and the like.

Figure 10:
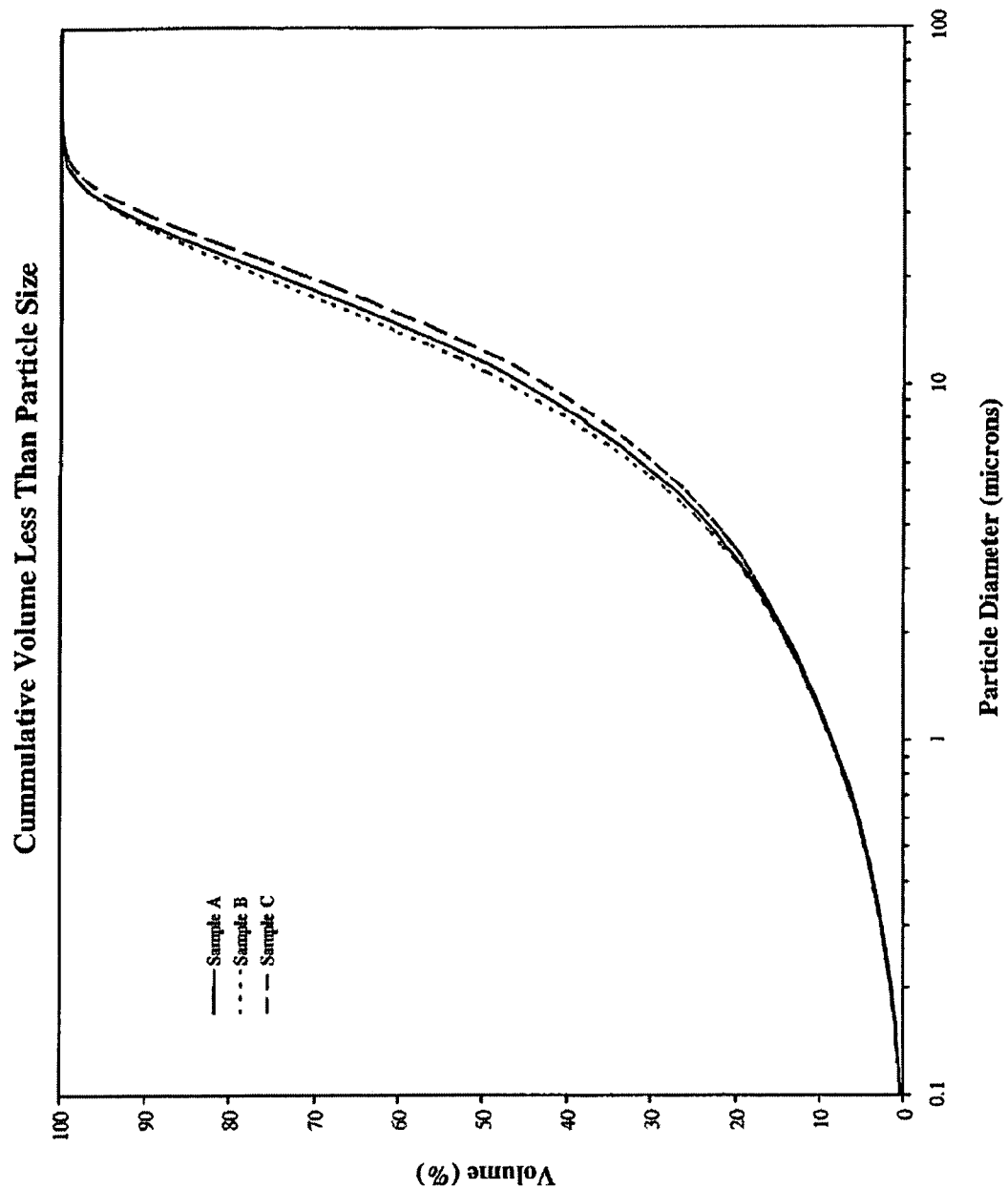
FIG. 10 shows the particle size distribution of three samples (A, B, and C) of OMYA-Cal® USP-10-AZ calcium carbonate powder as measured on a Coulter Particle Size Analyzer, expressed as cumulative volume percent of particle size less than the channel diameter, plotted on a logarithmic scale.
Figure 11:
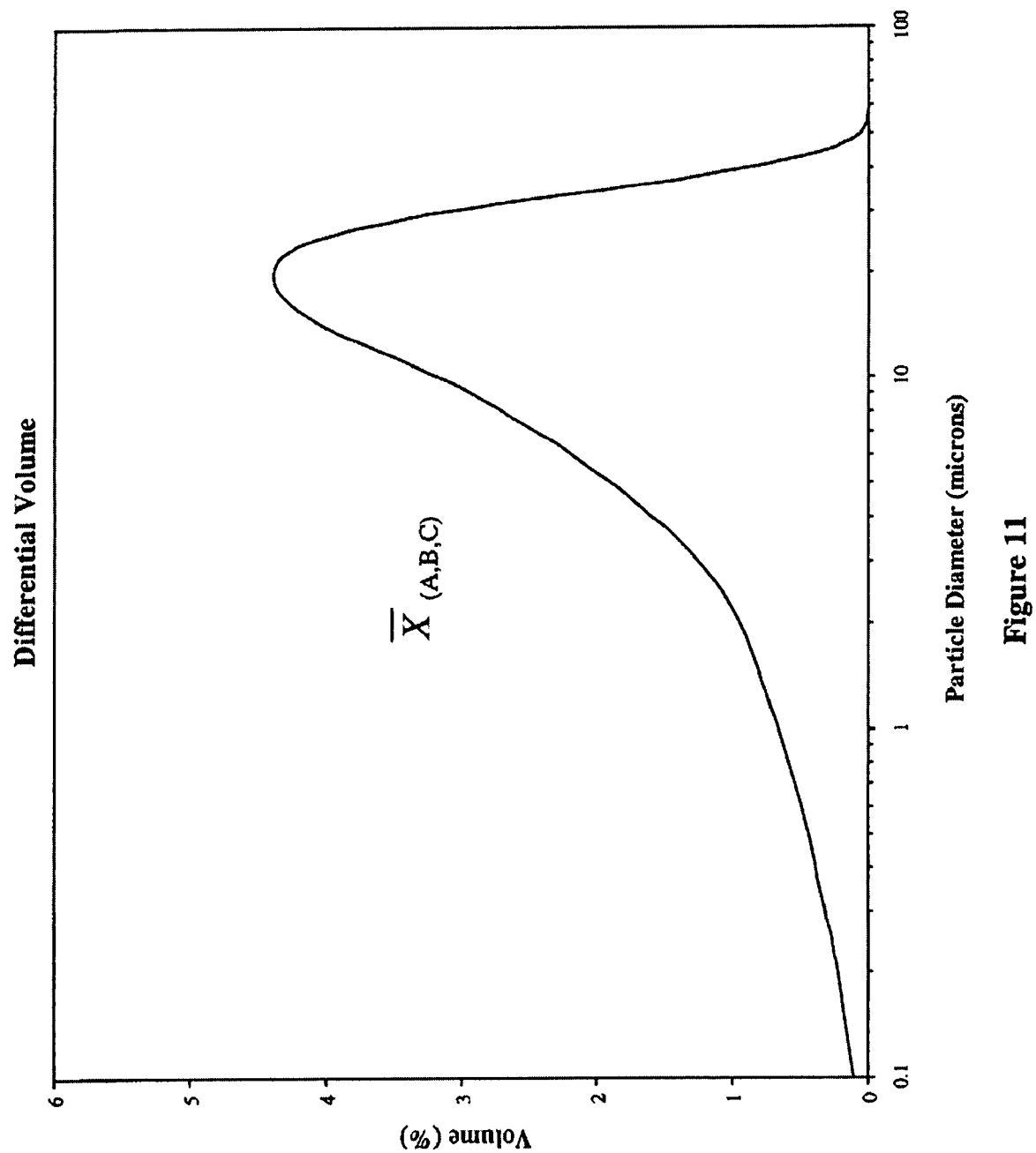
FIG. 11 shows the particle size distribution corresponding to the mean at each channel diameter, designated $\overline{X}_{(A,B,C)}$, of three samples (A, B, and C) of OMYA-Cal® USP-10-AZ calcium carbonate powder as measured on a Coulter Particle Size Analyzer, expressed as cumulative volume percent between each channel diameter, plotted on a logarithmic scale.
Figure 12:
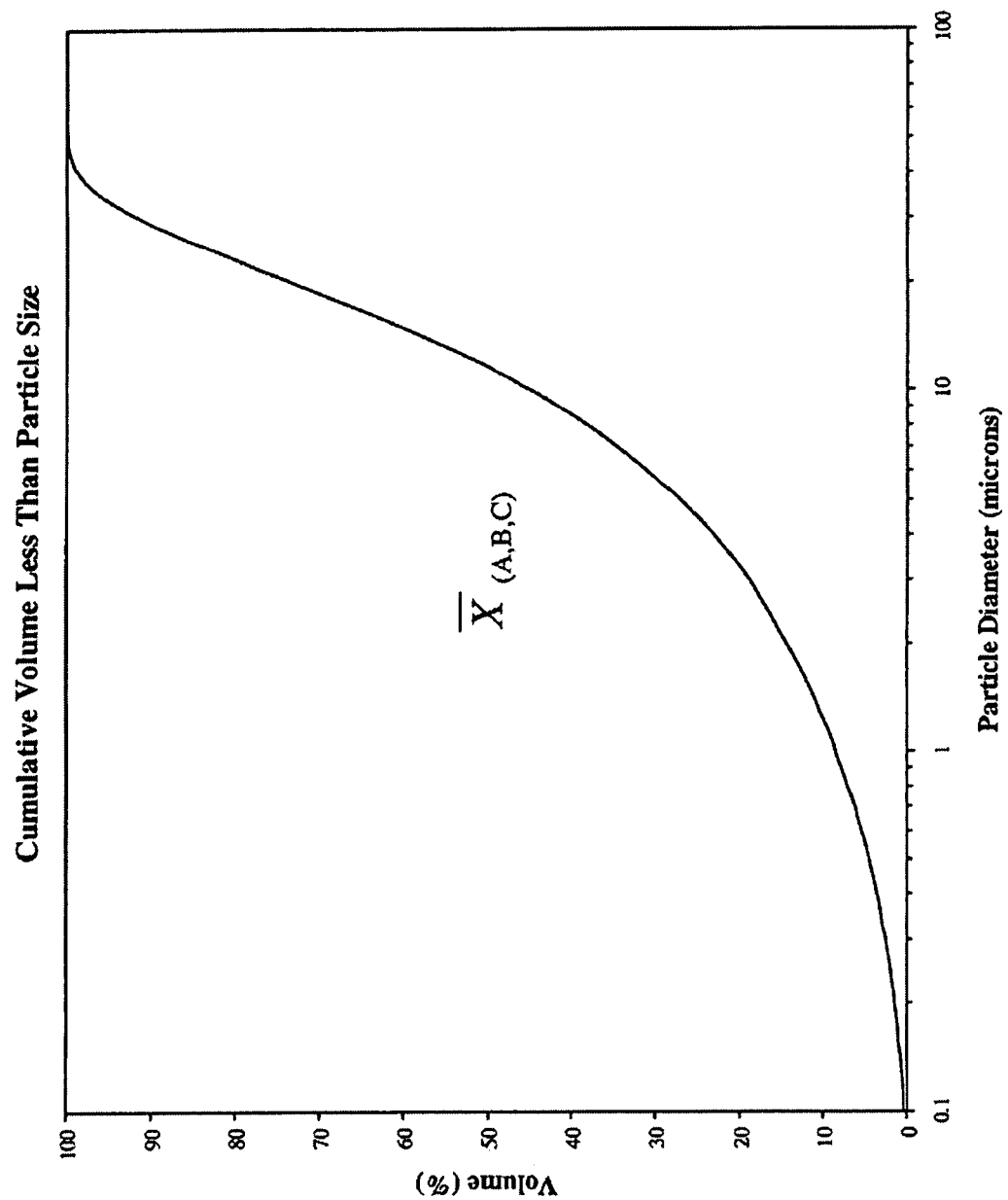
FIG. 12 shows the particle size distribution corresponding to the mean at each channel diameter, designated $\overline{X}_{(A,B,C)}$, of three samples (A, B, and C) of OMYA-Cal® USP-10-AZ calcium carbonate powder as measured on a Coulter Particle Size Analyzer, expressed as cumulative volume percent of particles of size less than the channel diameter, plotted on a logarithmic scale.
Figure 13:
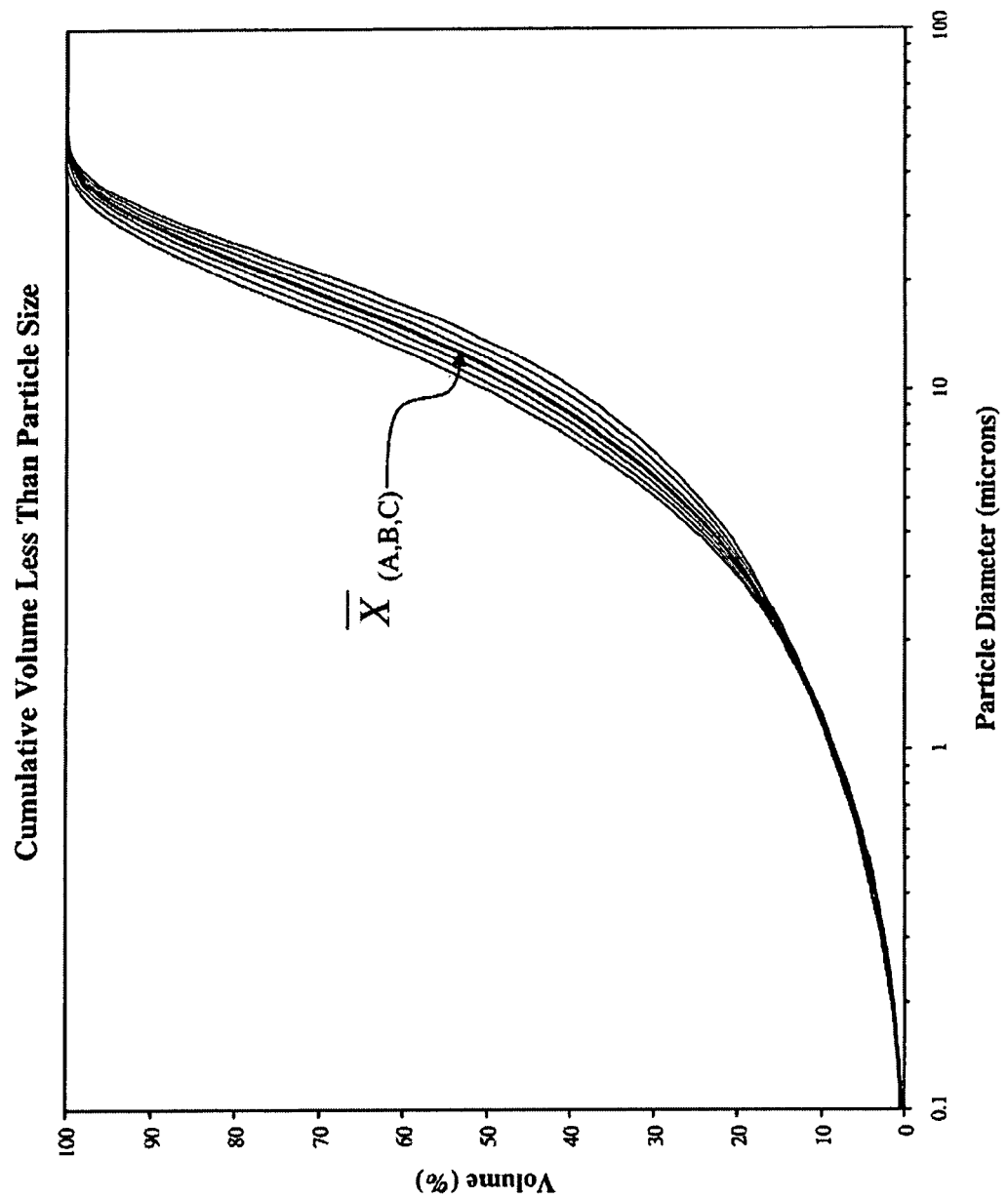
FIG. 13 shows the particle size distribution corresponding to the mean at each channel diameter, designated $\overline{X}_{(A,B,C)}$, of three samples (A, B, and C) of OMYA-Cal® USP-10-AZ calcium carbonate powder as measured on a Coulter Particle Size Analyzer, expressed as cumulative volume percent of particles of size less than the channel diameter, plotted on a logarithmic scale from 0.1 to 100 microns. The distribution corresponding to $\overline{X}_{(A,B,C)}$ is shown as the bold line. Distributions corresponding to ±1 SD (standard deviation), ±2 SD, and ±3 SD of the mean at each channel diameter are provided (thin lines).
Figure 14:
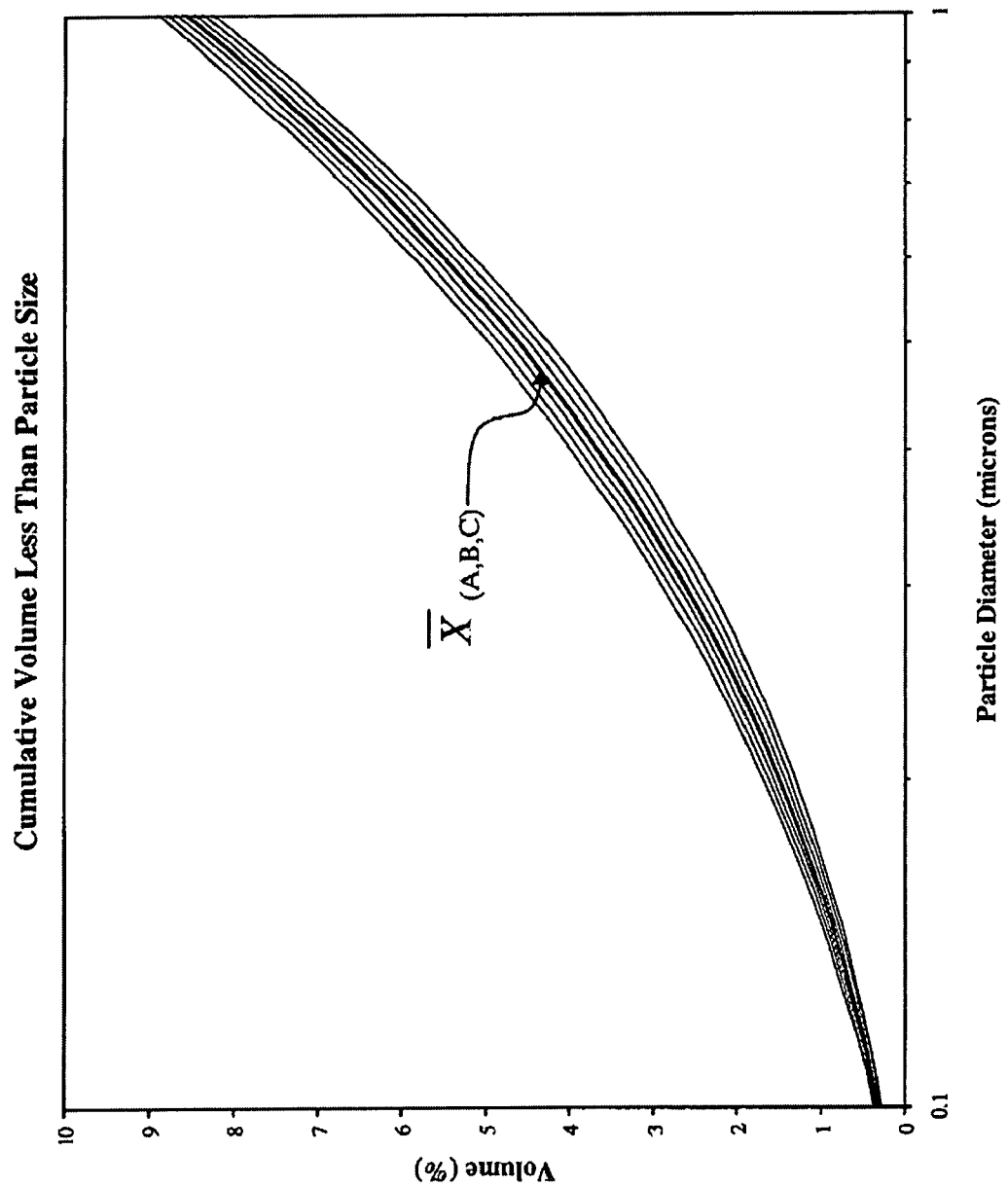
FIG. 14 is an enlargement of FIG. 13 in the small particle size range of 0.1 to 1 microns.
Figure 15:
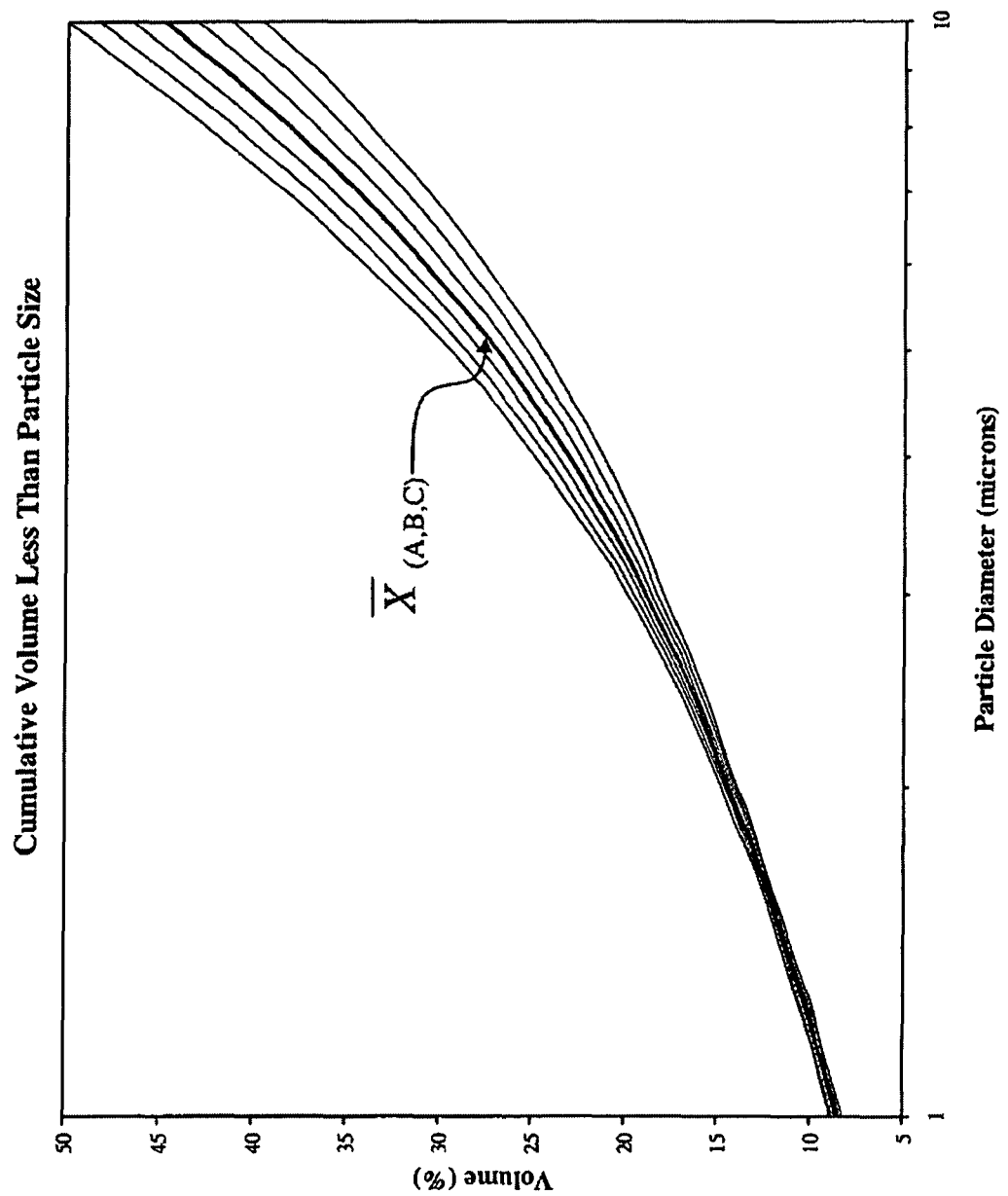
FIG. 15 is an enlargement of FIG. 13 in the intermediate particle size range of 1 to 10 microns.
Figure 16:
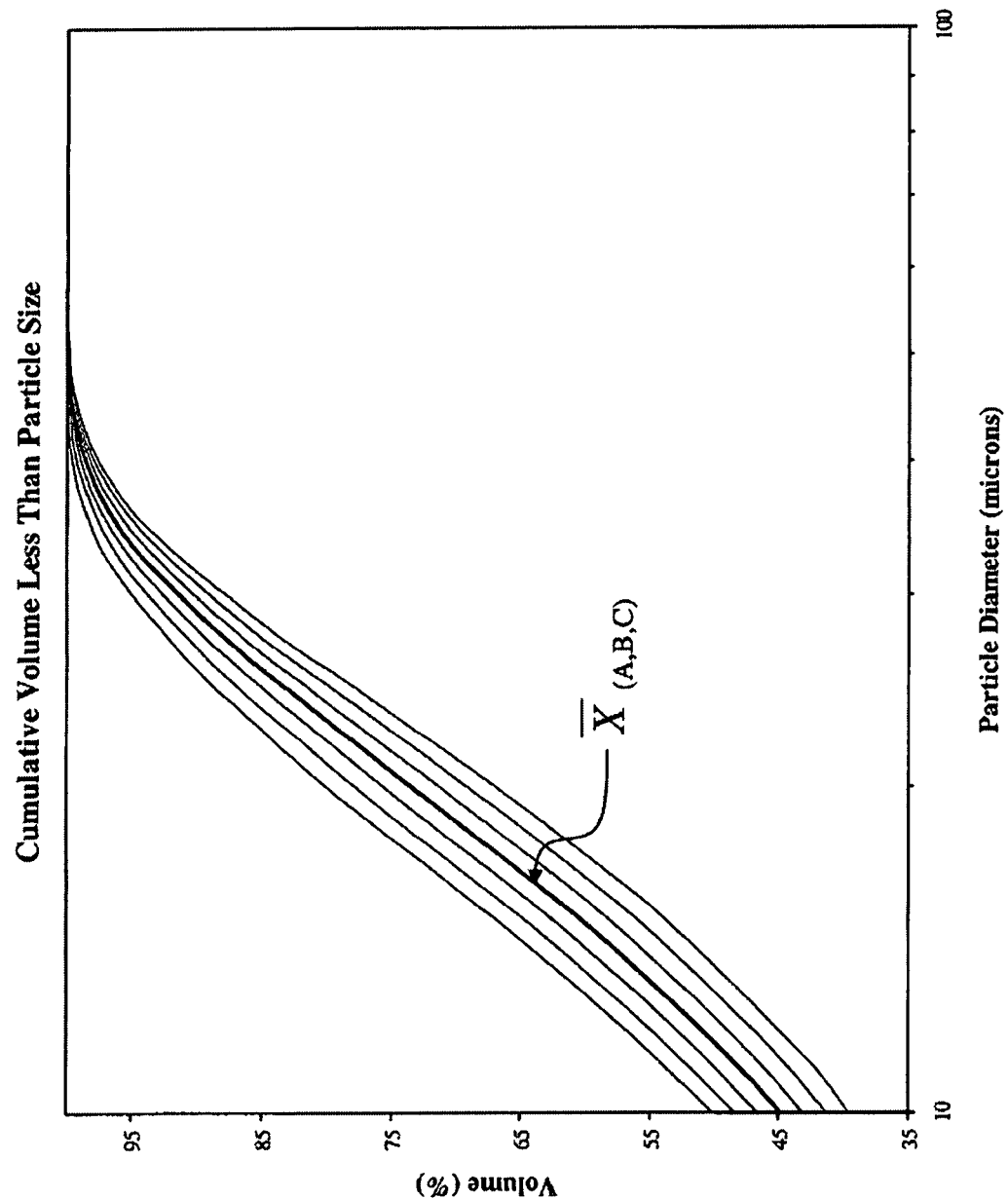
FIG. 16 is an enlargement of FIG. 13 in the large particle size range of 10 to 100 microns.

As used herein, "OMYA-Cal® USP-10-AZ" refers to the commercially available (Omya, Inc.) pharmaceutical grade mined limestone calcium carbonate powder (>99% $CaCO_3$) which has been ground to the particle size distribution of $\overline{X}_{(A,B,C)}$ provided in Table 7 of Example 2, which is shown graphically in FIGS. 9-16, in particular in FIG. 12, and characterized by the distribution statistics provided in Table 8. OMYA-Cal® USP-10-AZ is further characterized in that it has had acid insolubles removed.

The present invention is founded on the discovery that OMYA-Cal® USP-10-AZ, which has a median particle size of about 12 μm (microns), provides unexpectedly superior in vivo absorption efficiency and positive calcium balance as compared to calcium carbonate powders of other median particle sizes. The invention is not limited to the use of that OMYA-Cal® USP-10-AZ calcium carbonate powder, however. Rather, detailed analysis of the particle size distributions of this and other calcium carbonate powders has yielded critical insights into the parameters affecting absorption of calcium carbonate in the intestine. Without wishing to be bound by any theory, it is believed that the superior in vivo utilization efficiency of the about 12 μm median particle size OMYA-Cal® USP-10-AZ powder arises by virtue of its unique particle size distribution. As shown by its particle size distributions, this calcium carbonate powder provides substantial amounts of small (e.g., less than about 0.5 or 1 microns), intermediate (e.g. about 0.5 or 1 microns to about 10 or 11 microns), and large particles (e.g., greater than about 10, greater than about 11 microns, or greater than about 12.5 microns) which are believed to be differently utilized in the intestine to maximize net absorption, resulting in improved calcium balance.

Figure 1:
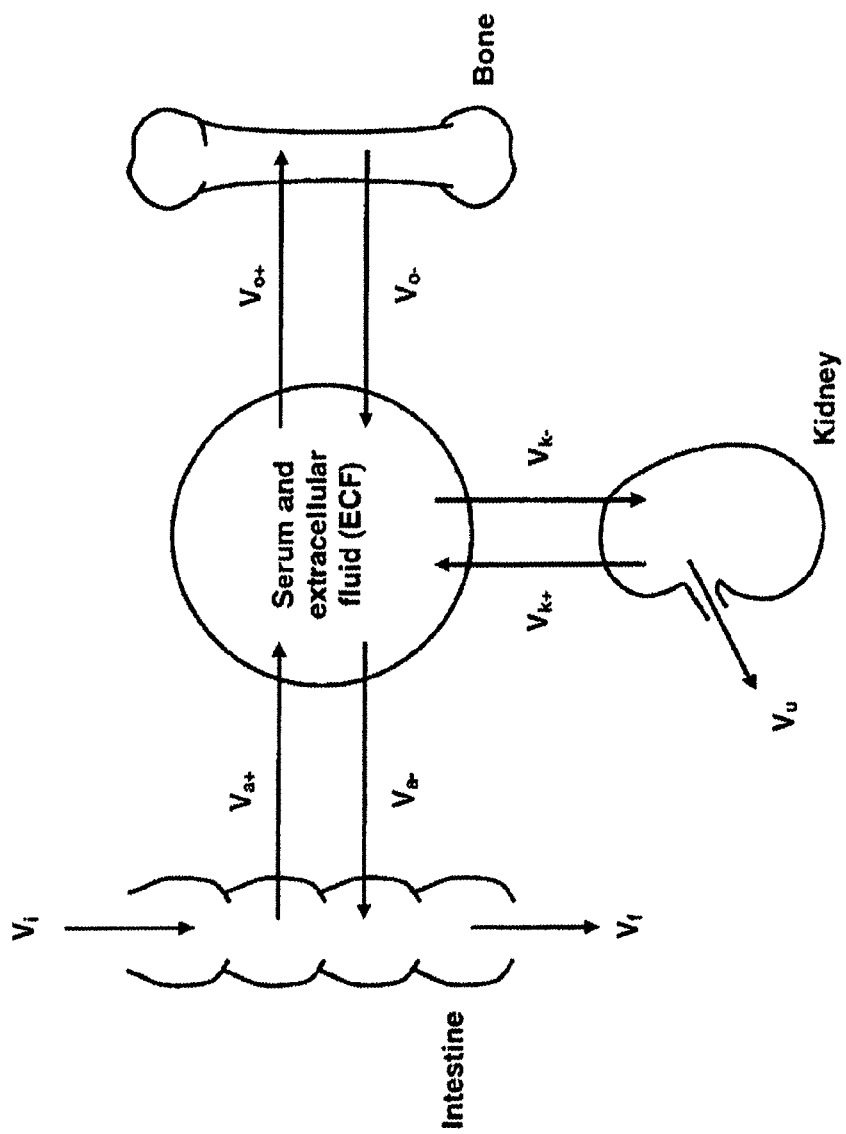
FIG. 1 illustrates the calcium regulatory system in humans.

Increasing net calcium absorption impacts bone calcium levels through the calcium homeostasis pathways. Calcium homeostasis in the body is maintained through the cooperative effects of the calcium regulatory system, primarily comprising: (1) calcium absorption and loss through the intestine; (2) absorption and desorption of calcium from the bone; and (3) calcium excretion in the urine and re-absorption from the kidneys. The primary pathways of calcium regulation are shown in FIG. 1. The serum and extracellular fluid (ECF) levels of calcium in humans is maintained in a relatively narrow range of about 2.25-2.5 mmol and thus may be regarded as a relatively constant calcium pool. These levels are maintained by the three principal regulatory components which act in concert to maintain the serum calcium levels. As illustrated in FIG. 1, the amount of ingested calcium $V_i$ is either lost through the feces, amount $V_f$, or is absorbed through the intestine in an amount $V_{a+}$. Endogenous calcium may also be lost from the calcium pool by desorption into the intestinal lumen, indicated by the quantity $V_{a-}$. At times the loss of endogenous calcium $V_{a-}$ may be substantial and may even exceed the amount $V_{a+}$. Accordingly, the term "net absorption" as used herein refers to the total net change in calcium through the intestine or $(V_{a+}-V_{a-})$ which can be measured as $(V_i-V_f)$. Net calcium absorption efficiency is measured as $(V_i-V_f)/V_i$. The term "absorption" refers only to the amount $V_{a+}$. The net change in calcium, commonly referred to as "calcium balance," is defined as $V_i-(V_f-V_u)$.

The absorption of calcium through the intestine may be regarded as the controlling factor of calcium balance whereas calcium loss from the bone and kidneys is up-regulated or down-regulated in response to intestinal calcium absorption. Thus, in healthy individuals calcium loss from the bones $V_{o-}$ is dependent on calcium absorption from the diet, with higher levels of absorption resulting in increased bone ossification $V_{o+}$. Conversely, inadequate calcium absorption through the intestine results in desorption of an amount of calcium $V_{o-}$ from the bone to maintain the serum levels. Similarly, the amount of calcium excreted in the urine $V_u$ is regulated by the re-absorption of calcium through the renal epithelial $V_{k-}$ which proceeds through a mechanism similar to active transport across the intestine, discussed below. The relevance of each of the three calcium regulatory mechanisms varies throughout life and thus presents different calcium demands at different times. For example, during early childhood the quantity $V_{o+}$ will exceed $V_{o-}$ resulting in net ossification of bone, highlighting the importance of adequate calcium intake at young age. In lactating women and post-menopausal women, however, the situation reverses, resulting in net calcium flux out of the bone reserves. Thus, at all life stages, and in particular in early life, lactation, and post-menopause, it is clearly desirable to increase $V_{a+}$.

There are two primary mechanisms of calcium absorption through the epithelial cells of the intestine: active transport (or facilitated diffusion) and passive transport, both of which contribute to the magnitude of $V_{a+}$. The first step in the active transport model involves the transport of $Ca^{2+}$ ions from the intestinal lumen through the transient receptor potential channel, vanilloid subfamily member 6 (TRPV6) calcium channels of the intestinal epithelial cells, primarily in the duodenum, jejunum, and ileum. Within the intestinal cells, intracellular diffusion of $Ca^{2+}$ is facilitated by the calcium binding protein calbindin $D_{9k}$ which binds two moles of calcium ion per mol of protein. The final step in the active transport model involves the release of calcium into the plasma by the action of plasma membrane calcium ATPases (PMCAs) or by the action of a $Na^+/Ca^{2+}$ exchanger. Because active transport of calcium requires $Ca^{2+}$ ions to be formed in the intestinal lumen, there must be a sufficient quantity of such ions present to maximize active transcellular transport, although this mechanism becomes saturated and no additional benefit is attained at high $Ca^{2+}$ levels. The action of hydrochloric acid in the gut on calcium carbonate produces $Ca^{2+}$ ions at a rate proportional to the surface area of the calcium carbonate particle. Therefore, small particles of calcium carbonate react more rapidly to generate $Ca^{2+}$ than do larger particles. To rapidly engage the active transport mechanism up to saturation, it was theorized that an optimal calcium supplement must have a sufficient volume of small calcium carbonate particles which will consume the available acid in the gut to yield $Ca^{2+}$. In this regard, small particles, as that term is used herein, refers to particle sizes typically below about 1 micron.

The second mechanism by which calcium crosses the intestinal epithelium is passive transport which involves the paracellular diffusion of both $Ca^{2+}$ and particulate calcium carbonate between the cells. Passive transport is believed to occur throughout the length of the intestine. This mechanism is independent of vitamin D status and regulated only by ionic gradients across the gut as well as bulk fluid flow properties. While not wishing to be bound by any theory, it is believed that the passive diffusion mechanism requires particles of specific particles sizes, including intermediate size particles, typically between about 1 micron to about 10 microns.

Thus, the total absorption of calcium through the intestine is the sum of active and passive calcium absorption. Because the active mechanism is saturatable and is down-regulated as calcium intake increases, above calcium doses of about 120 mg the passive diffusion of calcium is the controlling determinant of net calcium absorption. Because passive transport is not saturatable, net calcium absorption increases roughly linearly with calcium intake at intake levels above about 120 mg, although in vivo rat studies indicate that with calcium carbonate a plateau is reached with calcium carbonate at intake levels above 450 mg. Pansu et al., "Solubility and Intestinal Transit Time Limit Calcium Absorption in Rats," J. Nutrition Vol. 123, No. 8, pp. 1396-1404 (1993).

However, the efficiency of absorption, as a percentage of total calcium intake, is generally understood to be inversely related to calcium intake.

The presence of large particles, e.g., those having a size typically greater than about 10 microns, is also believed to be important to the improved absorption of the inventive calcium carbonate supplements. The larger particles react slowly with hydrochloric acid and are not believed to be available for passive transport across the intestine by virtue of their size. Accordingly, the residence time of large particles in the gut will be longer than for smaller particles. As hydrochloric acid acts on the large particles over time, they are degraded to smaller particles and calcium ions, thereby producing additional calcium in forms and sizes sufficient to engage the active and passive transport mechanisms. It is theorized that the calcium in the larger particles can therefore be metered out and presented to the intestinal epithelium over a longer period of time, essentially achieving a time-release calcium formulation. This is believed to be advantageous as it is known that calcium dosing regimens which are spread out throughout the day are substantially more effective than the delivery of the same dose in one bolus.

Ground limestone calcium carbonate powder having a median particle size of about 12 µm provides substantial volume of particles in each of the small, intermediate, and large particle ranges discussed above. The precise cutoffs for the various size ranges are derived empirically from the data in the Examples. Small particles are considered to be those which react instantly or rapidly to form solubilized $Ca^{+2}$ cations in the stomach and thus do not have substantial residence times in the intestine as particulates. Typically, the size of such particles will be less than 1 micron, although in various embodiments of the invention the "small" particles may by less than about 2 microns, less than about 1.5 microns, less than about 1 micron, less than about 0.5 microns, or less than about 0.25 microns in diameter. However, because solubilized $Ca^{+2}$ cations will be produced from calcium carbonate particles of all sizes, albeit at different rates, it is believed that sufficient calcium ion concentration will be present to saturate the active transport mechanism with most calcium carbonate sources regardless of the volume of small particles in the powder. Therefore, the precise volume of "small" particles is not considered essential to the practice of the invention, nevertheless it is believed to be advantageous to supply a substantial volume of small particles as they may further serve to deplete or reduce the available supply of gastric acid and thereby retard the degradation of intermediate and large particles. In one embodiment, the presence of small particle sizes of calcium carbonate powder is optional. In other embodiments, the small particles will comprise at least about 1%, at least about 2.5%, at least about 5%, at least about 7.5%, or at least about 9 or 10% of the total volume of calcium carbonate powder. In other embodiments, the amount of small particles comprises from about 1 to about 30%, from about 2.5 to about 25%, from about 5 to about 20%, from about 7.5 to about 10-15% by volume of the total volume of calcium carbonate. The small particles may comprise the lower end of the particle size distribution of a singular calcium carbonate source, such as for example OMYA-Cal® USP-10-AZ, in which about 9% of the total volume of calcium carbonate has a particle size below about 1 micron, or alternatively may be supplied by a separate powder source.

The intermediate size particles are typically between about 1 and about 11 microns, but in various embodiments the lower end of the intermediate range may be about 0.25 microns, about 0.5 microns, or about 0.75 microns, and the upper end of the intermediate range may be about 7.5 microns, about 10 microns, about 12 microns, or about 15 microns. It is believed that these particle sizes are important for increasing or optimizing the passive absorption of calcium. This conclusion follows from a comparison of the relative absorption efficiencies of OMYA-Cal® USP-10-AZ and OMYA-Cal® USP-15-AZ calcium carbonate powders in the rat model discussed in the Examples. As shown by the data in the Examples, the absorption efficiency and resulting calcium balance in rats is substantially and unexpectedly higher in rats fed OMYA-Cal® USP-10-AZ than in rats fed OMYA-Cal® USP-15-AZ. The particle size distributions of these two powders is compared in FIG. 2, where $\overline{X}_{(A,B,C)}$ represents the average of three samples (A, B, and C) of OMYA-Cal® USP-10-AZ powder having a median particle size of about 12 microns and $\overline{X}_{(D,E,F)}$ represents the average of three samples (D, E, and F) of OMYA-Cal® USP-15-AZ powder having a median particle size of about 16 microns. Comparison of these distributions reveals that the volume of particles of size greater than about 10 or 11 microns in the OMYA-Cal® USP-15-AZ powder is far greater than present in the OMYA-Cal® USP-10-AZ powder. In fact, the distribution curve for OMYA-Cal® USP-15-AZ subsumes that of OMYA-Cal® USP-10-AZ above about 12 microns (the exact cross-over point is at 11.83 microns). Thus, the superior results of OMYA-Cal® USP-10-AZ powder on absorption efficiency and calcium balance cannot be explained solely by the difference in particle size distributions in the region above 12 microns because the OMYA-Cal® USP-10-AZ powder provides less volume of particles at all sizes above 12 microns than provided by OMYA-Cal® USP-15-AZ. On the contrary, if this region of the distribution, alone, were important it would be expected that the larger median particle size material OMYA-Cal® USP-15-AZ would outperform. Similarly, below about 0.5 microns the distribution curves for these two calcium carbonate powders are similar and below about 0.25 they are essentially identical. Accordingly, the superior results of OMYA-Cal® USP-10-AZ cannot be explained solely on the basis of the small particles either.

Figure 2:
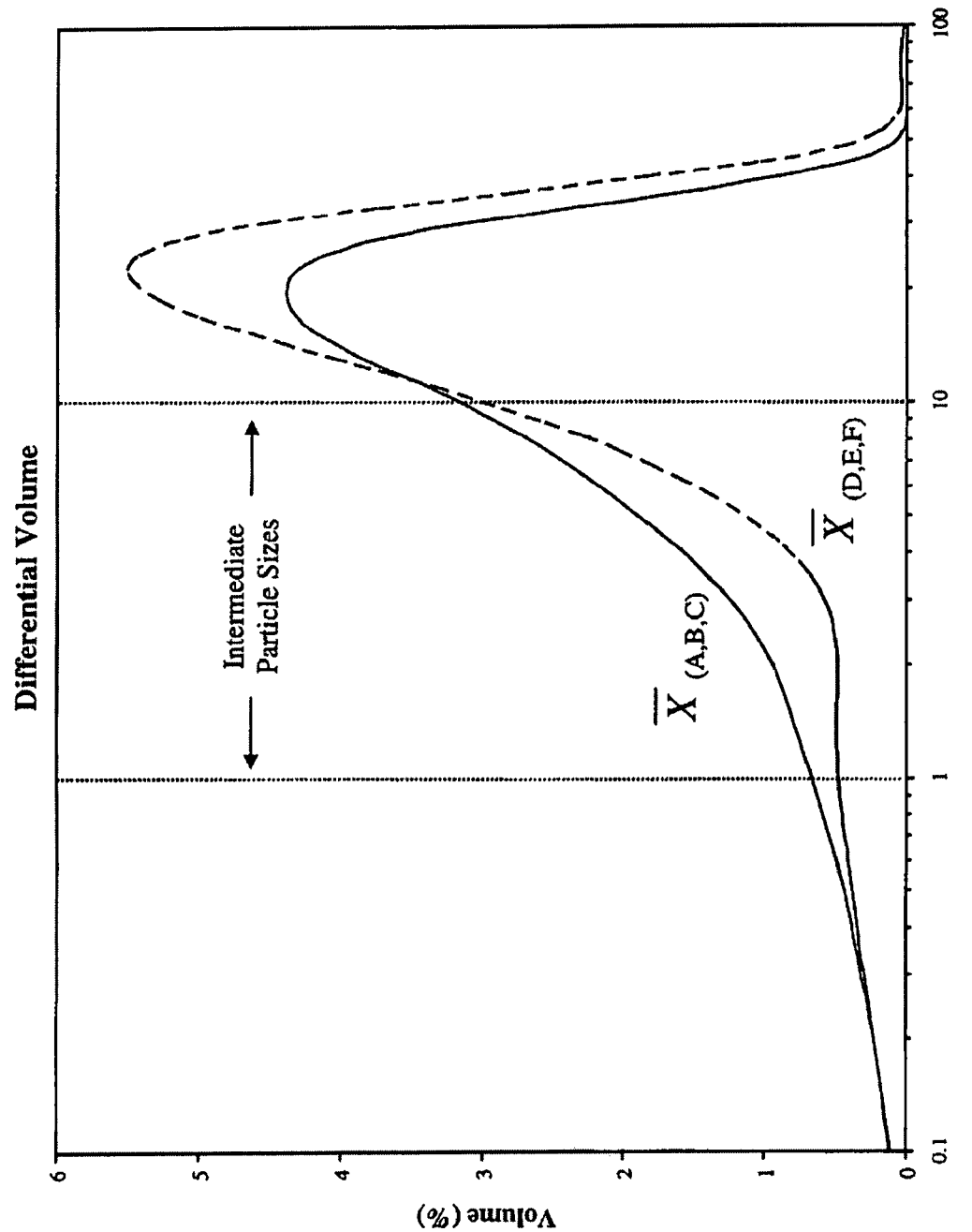
FIG. 2 shows the particle size distribution of the OMYA-Cal® USP-10-AZ calcium carbonate powder according to the invention (shown as the average of three samples, designated $\overline{X}_{(A,B,C)}$), expressed as percent differential volume between channel diameters of the Coulter Particle Size Analyzer, compared to the conventional OMYA-Cal® USP-15-AZ powder (shown as the average of three samples, designated $\overline{X}_{(D,E,F)}$). As illustrated, the OMYA-Cal® USP-10-AZ calcium carbonate powder provides substantially more powder volume in the intermediate particle size range than does the conventional OMYA-Cal® USP-15-AZ powder.

It is therefore theorized that the difference in absorption efficiency of OMYA-Cal® USP-10-AZ and OMYA-Cal® USP-15-AZ results from the differences seen in FIG. 2 between the particles of sizes in the range of about 0.5 or 1 micron to about 10 or 11 microns. Without wishing to be bound be any particular theory, it is believed that the higher volume of particles within this range in the OMYA-Cal® USP-10-AZ powder is important for enhancing or optimizing passive transport through the intestine (paracellular diffusion). Regardless of the correctness of the theory, the results in the Examples establish the importance of particle sizes within the intermediate size range. Typically, the calcium carbonate powders of the invention will comprise more than about 25% by volume of particles within the intermediate size range. In various embodiments, the calcium carbonate powder will comprise at least about 26%, at least about 28%, at least about 30%, at least about 32%, at least about 34%, at least about 36%, or at least about 38% by volume particles in the intermediate size range. The OMYA-Cal® USP-10-AZ calcium carbonate powder comprises about 38% by volume particles within the size range of about 1 micron to about 11 microns. The intermediate particles may comprise a portion of one calcium carbonate powder source or may be provided from a separate calcium carbonate source.

The lower size cutoff of the "large" particles is not particularly critical and may include particles larger than about 7.5, 10, 11, 12, or about 15 microns. The volume of large particles will typically comprise at least about 40%, at least about 42.5%, at least about 45%, at least about 47.5%, or at least about 50% of the total volume of calcium carbonate powder. Preferably, the volume of large particles will be greater than about 50%, or greater than about 52% of the total volume of the calcium carbonate powder, particularly in embodiments where the large particles are those having a particle size greater than about 10 or 11 microns. The OMYA-Cal® USP-10-AZ calcium carbonate powder comprises about 53% of the total volume at particle sizes greater than about 11 microns. It is believed that the presence of the large particles advantageously increases the residence time of the calcium carbonate in the digestive system and thereby presents calcium to the intestine for active and passive absorption over a longer period of time than achievable in the absence of such large particles.

The calcium carbonate powders meeting the criteria described herein may be provided in any suitable form for delivery to humans or animals. For example, the calcium carbonate powders may be added to any food, beverage, chewable, candy, nutritional bar or the like. In various embodiments, pharmaceuticals, nutraceuticals, functional foods, and dietary supplements are provided comprising the highly bioavailable calcium carbonate powders of the invention.

Preferably, the calcium carbonate powders of the invention are provided in the form of calcium supplement tablets, such as, for example, those described in U.S. Pat. No. 7,198,653 to Lang et al., the disclosure of which is hereby incorporated by reference. The tablets described in that patent will have a reduced tablet volume due in part to the unique processing parameters described therein. Further reduction in tablet volume is achieved according to the present invention based on the discovery that less enhanced absorption calcium carbonate is required to meet the AIs as compared to conventional calcium carbonate. In fact, particular synergies in tablet size reduction will be obtained where the preferred enhanced absorption calcium carbonate powders according to the present invention, which have a median particle diameter of about 12 μm, are incorporated into a highly compactable, high density granulation according to U.S. Pat. No. 7,198,653 and subsequently compressed into a tablet.

Tablets according to the present invention include but are not limited to molded tablets, chewable tablets, pellets, pills, triturates, hypodermic tablets, effervescent tablets, controlled-release tablets, and immediate release tablets. The calcium supplement tablet may comprise any additional ingredients known to one skilled in the art, including pharmaceutically or nutraceutically acceptable excipients, for example, carriers, diluents, disintegrants, lubricants, flavorants, and the like.

The calcium supplement tablets may comprise any amount of the calcium carbonate powders according to the invention, but will typically comprise from about 100 mg to about 4,000 mg of calcium carbonate powder, preferably OMYA-Cal® USP-10-AZ (Omya, Inc.) calcium carbonate powder. In various embodiments, the calcium supplement tablets will comprise at least 200 mg, at least 300 mg, at least 400, at least 500, at least 600 mg, at least 700 mg, at least 800 mg, at least 900 mg, at least 1,000 mg, at least 1,200 mg, at least 1,300 mg, at least 1,400 mg, at least 1,500 mg, at least 1,600 mg, at least 1,700 mg, at least 1,800 mg, at least 1,900 mg, or at least 2,000 mg of calcium carbonate powder according to the invention, preferably OMYA-Cal® USP-10-AZ (Omya, Inc.) calcium carbonate powder.

Preferably, the calcium supplements will also comprise vitamin D (including vitamin D metabolites). Typically, the supplement will comprise at least about 200 I.U. (international units) of vitamin D, preferably, at least 300 I.U. of vitamin D, at least about 400 I.U. of vitamin D, at least 500 I.U. of vitamin D, at least about 600 I.U. of vitamin D, at least about 700 I.U. of vitamin D, at least about 800 I.U. of vitamin D, or at least about 900 I.U. of vitamin D, and may range upwards of (at least) about 1,000 I.U., about 2,000 I.U., about 2,500 I.U., about 3,000 I.U. or about 3,500 I.U. of vitamin D. In some notable embodiments, the supplements will comprise about 400 I.U. of vitamin D or about 800 I.U. of vitamin D per tablet or per dosage form. It is contemplated that unexpectedly higher absorption efficiency will result from the use of large doses of vitamin D including, without limitation, daily vitamin D doses of about 800 I.U. or 1,000 I.U. up to about 2,000 I.U or above. In the preferred practice of the invention, the supplements will comprise vitamin D in the form of vitamin $D_3$ due to its superior ability to be stored in the human body as compared to the other forms of vitamin D, including vitamin $D_2$. In some embodiments, the vitamin D may consist essentially of vitamin $D_3$ by which is meant that any amounts of other vitamin D species (such as vitamin $D_2$), if present, should be of sufficiently low levels as to not have a measurable impact on calcium absorption as measured over a period of at least eight weeks. In other embodiments, the vitamin D will comprise at least about 75%, preferably at least about 85%, and more preferably, at least about 95% vitamin $D_3$ by weight. The vitamin D, particularly vitamin $D_3$, may be encapsulated in a gelatin matrix, or may be provided in an encapsulant that is substantially free of gelatin (e.g., less than 1% gelatin) or free of gelatin, such as, without limitation, a microcrystalline cellulose matrix.

The supplements of the invention may comprise one or more calcium carbonate powders, at least one of which meets the particle size distribution characteristics defined herein. Thus, the addition of other calcium carbonate powders, or other powders of calcium salts, is not contemplated to be deleterious to the practice of the invention provided that at least one calcium carbonate powder is present which satisfies the particle size distribution criteria discussed herein, including for example OMYA-Cal® USP-10-AZ.

Similarly, the invention is not limited to the use of a singular powder which meets the specified particle size limitations, but rather embraces mixtures of different calcium carbonate powders provided that the aggregate provides sufficient volume of small, intermediate, and large particles as described herein. Thus it is contemplated that two powders (or more) of different median particle size may be combined to provide a singular powder meeting the particle size distribution requirements for enhanced absorption.

In one embodiment, the calcium carbonate in the supplements of the invention comprises, consists essentially of, or consists of a singular calcium carbonate powder meeting the particle size limitations described herein, including without limitation, OMYA-Cal® USP-10-AZ calcium carbonate powder, and optionally one or more pharmaceutically or nutraceutically acceptable excipients, and optionally vitamin D or any other absorption enhancing agent. By "consists essentially of" is meant that any amounts of other calcium carbonate powder, such as conventional calcium carbonate powder, which would diminish the enhanced absorption of the inventive calcium carbonate is excluded. In one embodiment, the presence of additional calcium carbonate powder, such as conventional calcium carbonate powder, is excluded if the presence of such powder, in the aggregate, would result in a net decrease in the volume of particles in the intermediate size range.

It is further contemplated that other calcium sources may optionally be included with the calcium carbonate powders of the invention. However, it is preferred that such other calcium sources also exhibit high bioavailability (i.e., higher absorption than conventional calcium carbonate). In this regard, special mention may be made of the calcium citrate malate salts described in U.S. Pat. No. 5,128,374 to Kochanowski; U.S. Pat. No. 5,186,965 to Fox et al.; U.S. Pat. No. 5,314,919 to Jacobs; U.S. Pat. No. 5,468,506 to Andon; and U.S. Pat. No. 6,080,431 to Andon et al., the disclosures of which are hereby incorporated by reference herein. Accordingly, one embodiment of the invention comprises a composition comprising enhanced absorption calcium carbonate and calcium citrate malate, which composition may be included in a tablet, or any other delivery vehicle known in the art, including those described herein.

The invention provides methods for increasing calcium absorption or net calcium absorption in a human or mammal comprising administering to the human or mammal any of the inventive calcium carbonate forms defined herein. Preferably, the calcium form has a particle size distribution similar to ($\pm 3$ SD), approximately the same as ($\pm 2$ SD), substantially identical to ($\pm 1$ SD), or identical to the particle size distribution of $\overline{X}_{(A,B,C)}$ across the entire range of particle sizes. In other embodiments, the enhanced absorption calcium carbonate powders have a particle size distribution similar to, approximately the same as, substantially identical to, or identical to the particle size distribution of $\overline{X}_{(A,B,C)}$ across the range of intermediate particles (e.g., about 0.25, 0.5, 0.75, or 1 microns to about 10, 11 or 12.5 microns) and optionally similar to, approximately the same as, substantially identical to, or identical to the particle size distribution of $\overline{X}_{(A,B,C)}$ across the range of small and/or large particle sizes or any portion thereof.

In preferred embodiments of the inventive method, the calcium carbonate powder is delivered in conjunction with vitamin D, preferably at a level of at least 200 I.U. of vitamin D, and more preferably, at least about 400 I.U. of vitamin D per dose. The method embraces once-a-day dosing regimens as well as multiple dosing regimens. Typically, the dosing regimen will provide at least 300 mg, at least 350 mg, at least 400 mg, at least 500 mg, at least 600 mg, at least 700 mg, at least 1,000 mg, at least 1,200 mg, at least 1,300 mg, at least 1,500 mg, or at least about 1,800 mg of elemental calcium daily. In preferred embodiments, the methods of the invention achieve an absorption efficiency at least about 5% greater, at least 7.5% or greater, preferably at least about 10% greater, more preferably at least about 15% greater, and more preferred still, at least 20% or greater than achievable with otherwise comparable formulations of any other known calcium carbonate powder (i.e., "conventional calcium carbonate powder"), including those having a median particle size of 2, 5, or 16 microns as described herein. In a preferred embodiment, the method of the invention comprises administering to an individual in need thereof the calcium carbonate powder OMYA-Cal® USP-10-AZ (Omya, Inc.), preferably in a dose of at least about 600 mg daily up to about 3,500 mg or more daily, and at least 200 I.U., preferably at least 400 I.U., of vitamin D up to about 2,500 I.U., daily.

It is known that adequate calcium ingestion during childhood is critical for developing peak skeletal mass. For example, it has been estimated that 40% of the lifetime bone mass is accumulated during adolescence. See Greer et al., "Optimizing Bone Health and Calcium Intakes of Infants, Children, and Adolescents," *Pediatrics*, Vol. 117 No. 2 Feb. 2006, pp. 578-585. Building healthy bones during childhood will reduce fractures and may partially offset future calcium demands, thereby serving as a preventative measure against osteoporosis in later life. See Institute of Medicine, Food and Nutrition Board. Dietary Reference Intakes for Calcium, Phosphorus, Magnesium, Vitamin D, and Fluoride. Washington, D.C.: National Academy Press; 1997, the disclosure of which is hereby incorporated by reference. Accordingly, one embodiment of the invention provides a method of building or strengthening bones in pre-adolescents or adolescents humans or mammals comprising administering daily, preferably chronically or for a period of at least eight weeks, to a pre-adolescent or adolescent individual (male or female) any of the highly bioavailable calcium carbonate powders of the invention, including but not limited to OMYA-Cal® USP-10-AZ, and vitamin D. Preferably, at least about 1,500 mg to about 4,000 mg of calcium carbonate is administered daily and at least 400 I.U., at least 800 I.U., or at least 1,000 I.U. up to about 2,500 I.U. of vitamin D is administered daily. The compositions and methods of the invention are also contemplated to be useful for preventing bone fractures, improving healing time of bone fractures, and improving bone strength in bones which have been fractured.

The highly bioavailable calcium carbonate powders of the invention, including but not limited to OMYA-Cal® USP-10-AZ are contemplated to be useful for preventing, treating, reversing, and/or ameliorating bone loss associated with osteoporosis, particularly in combination with vitamin D. Accordingly, the invention provides in one embodiment a method of preventing, treating, reversing, and/or ameliorating bone loss comprising administering to a patient in need thereof (i.e., a patient suffering from osteoporosis or at risk of developing osteoporosis) an effective amount of any of the calcium carbonate powders of the invention, such as OMYA-Cal® USP-10-AZ, for a time sufficient to prevent, treat, reverse, and/or ameliorate bone loss. The term "effective amount" refers to a dosage sufficient to provide the recommended daily intake of elemental calcium. The time sufficient to prevent, treat, reverse, and/or ameliorate bone loss is not contemplated to be particularly limited and includes, for example, daily administration for at least two weeks, preferably at least eight weeks, and more preferably chronic administration.

It is contemplated that the methods of the invention will constitute a useful complement to pharmaceutical intervention or, ideally, as a replacement for osteoporosis drugs such as bisphosphonates. In one embodiment, a pharmaceutical composition comprises a pharmaceutically effective amount of any of the calcium carbonate materials having enhanced bioavailability described herein and a pharmaceutically effective amount of a bisphosphonate osteoporosis drug. In another embodiment, the pharmaceutically effective amounts of calcium carbonate and bisphosphonate are delivered to a patient in need thereof (e.g., a patient suffering from osteoporosis) seriatim. Thus, a method for treating osteoporosis comprises administering to a patient, simultaneously or seriatim, a pharmaceutically effective amount of any of the calcium carbonate materials having enhanced bioavailability described herein and a pharmaceutically effective amount of a bisphosphonate osteoporosis drug.

In this context, the term "pharmaceutically effective amount" refers to an amount sufficient to prevent, reduce, reverse, and/or ameliorate bone loss associated with osteoporosis. In the case of calcium carbonate, the pharmaceutically effective amount will typically be at least about 100 mg or at least about 200 mg, more typically at least about 300 mg, and preferably at least about 400 mg, and more preferably, at least about 500 mg, and more preferred still, at least about 600 mg of calcium carbonate per dosage form. On a daily basis, a pharmaceutically effective amount" of calcium carbonate will be from about 100 to about 3,500 mg/day, from about 200 to about 3,000 mg/day, from about 300 to about 2,500 mg/day, from about 400 to about 2,500 mg/day, from about 500 to about 2,500 mg/day, or from about 600 to about 2,500 mg/day. Ideally, the pharmaceutically effective amount of calcium carbonate will be such that typically at least about 600, more typically at least about 700, preferably at least about 800, more preferably at least about 900, and more preferred still at least about 1,000 mg of elemental calcium is delivered per dosage form or per day.

The "pharmaceutically effective amount" of calcium carbonate will optimally delivery sufficient elemental calcium to at least meet the AI of 1,000 mg/day in adults (ages 19 to 50) or 1,200 mg/day for those over 50, but will preferably be even higher and will include amounts up to about 1,800 mg/day, or even 2,500 mg/day of elemental calcium. The pharmaceutically effective amount of bisphosphonate will of course depend on the particular bisphosphonate, but will typically range from about 0.1 to about 500 mg. On a daily basis, the pharmaceutically effective amount will usually range from about 0.5 to about 25 mg, from about 0.75 to about 20 mg, from about 1 to about 17 mg, from about 1.5 to about 15 mg, or from about 2 to about 10 mg per day. Exemplary, pharmaceutically effective amounts of bisphosphate include about 0.5, 1, 1.5, 2, 2.5, 3, 4, 5, 6, 7, 8, 9, 10, 12.5, or about 15 mg per day, each being understood to be a distinct embodiment of the invention. Thus, individual dosage forms for daily administration will typically comprise the foregoing amounts of bisphosphonate or may be formulated as twice daily or thrice daily forms which collectively provide the foregoing amounts on a daily basis (for example, a twice daily dosage may comprise exactly or approximately half of the foregoing effective amounts). Preferably, the daily effective amount is delivered as a single dosage administered once daily. On a weekly basis, the pharmaceutically effective amount of bisphosphonate will usually range from about 5 to about 200 mg, from about 10 to about 150 mg, from about 20 to about 100 mg, from about 30 to about 80 mg, or from about 35 to about 75 mg per week provided as one or more doses. Exemplary, pharmaceutically effective amounts of bisphosphate include about 20, 25, 30, 35, 40, 45, 50, 55, 60, 65, or about 75 mg per week, each being understood to be a distinct embodiment of the invention. Thus, individual dosage forms for weekly administration will typically comprise the foregoing amounts of bisphosphonate, or dosage forms may be formulated to provide a dosage regimen which collectively provides these weekly effective amounts when administered once, twice, or thrice daily, every two days, twice weekly, once weekly, or the like. Preferably, the effective amount, on a weekly basis, is delivery as a single dosage once a week. The pharmaceutically effective amount of bisphosphonate may also be delivered as a monthly dosage which will typically range from about 20 to about 800 mg, from about 40 to about 600 mg, from about 80 to about 400 mg, from about 120 to about 350 mg, or from about 140 to about 300 mg per month provided as one or more doses. Exemplary, pharmaceutically effective amounts of bisphosphate include about 100, 125, 150, 175, 200, 225, 250, 275, 300, 325 or about 350 mg per month, each being understood to be a distinct embodiment of the invention. The effective amount on a monthly basis may be delivered daily, weekly, bi-weekly, once-a-month, or the like, where each administration is formulated to deliver equal amounts of bisphosphante which collectively total to the monthly effective amount. Preferably, the effective amount, on a monthly basis, is delivery as a single dosage once a month.

The osteoporosis treatment regimens preferably comprise the administration of a pharmaceutically effective amount of calcium carbonate on a daily basis, more preferably, on a twice-daily basis, and more preferred still at a plurality of intervals through a day, e.g. three times daily, four times daily, hourly, every two hours, etc. While it is contemplated that the benefits of the invention will be most fully realized with multiple daily administrations of calcium carbonate, it may be advantageous to administer calcium carbonate only once daily or twice daily due known difficulties with patient compliance in multi-dose regimens. The bisphosphonate will typically be administered once daily, once weekly or once monthly. When delivered once daily, the calcium carbonate and bisphosphonante may be administered together (e.g., in the same dosage form or in separate dosage forms taken together) or administered seriatim, in either order and with any period of time between each administration. It has been suggested that calcium may, to some extent, interfere with absorption of bisphosphonates. Therefore, it may be desirable to provide a daily regimen comprising, for example, taking calcium carbonate in the morning and bisphosphonate in the evening, or vice versa, or one before a meal and one after, etc. However, the advantages of high patient compliance with single doses will likely offset any reduction in bisphosphonate absorption. Therefore, in a preferred embodiment, the effective amounts of calcium carbonate and bisphosphonate are delivered together, preferably in a single dosage form.

Suitable bisphosphonates include, without limitation, those bisphosphonates suitable for oral delivery, for example, alendronate (Fosamax®); risedronate (Actonel®); ibandronate (Boniva®) and the like, as well as injectable bisphosphonates, such as etidronate (Didronel®), pamidronate (Aredia®), zoledronate (Zometa®) and the like. Preferred bisphosphonates according to the invention are alendronate, risedronate, and ibandronate.

The pharmaceutical compositions and dosing regimens may also include vitamin D in any dose described herein. Preferably, at least 200 I.U. of vitamin D are delivered daily and more preferably at least 400 I.U., 800 I.U., or 1,000 I.U. daily of vitamin D. In other embodiments, daily doses of vitamin D may be up to about 2,000 I.U. or more, including exemplary ranges of about 200 to about 2,000 I.U., about 400 to about 1,750 I.U., about 600 to about 1,500 I.U. or about 1,000 I.U. daily.

In a currently preferred embodiment, the bisphosphonate is alendronate, and the pharmaceutically effective dose is typically about 5 to about 15 mg, preferably, about 6 to about 14 mg, more preferably about 7 to about 13 mg, and more preferred still about 8 to about 12 mg per day. Superior results are contemplated where the dosage of alendronate is between about 9 and about 11 mg daily or about 10 mg daily. The pharmaceutically effective amounts for weekly or monthly administration are contemplated to be approximately the daily effective amount multiplied by the dosing interval. That is, a weekly effective amount will be, for example, approximately seven times the daily amount and a monthly effective amount will be approximately 30 times the daily effective amount. It is contemplated that a weekly dose of about 50 to about 80 mg/week or about 65 to about 75 mg/week will be particularly useful. Of course, any of the daily, weekly, or monthly pharmaceutically effective amounts of bisphosphonate described elsewhere herein are equally applicable to this embodiment.

In another currently preferred embodiment, the bisphosphonate is risedronate, and the pharmaceutically effective dose is typically about 1 to about 10 mg, preferably, about 1.5 to about 9 mg, more preferably about 2 to about 8 mg, and more preferred still about 2.5 to about 7 mg per day. Superior results are contemplated where the dosage of alendronate is between about 3 and about 6 mg daily, 4 and about 6 mg daily, or about 5 mg daily. The pharmaceutically effective amounts for weekly or monthly administration are contemplated to be approximately the daily effective amount multiplied by the dosing interval. It is contemplated that a pharmaceutically effective does of about 25 to about 45 mg/week or about 30 to about 40 mg/week will be particularly useful. The daily, weekly, or monthly pharmaceutically effective amounts of bisphosphonate described elsewhere herein are equally applicable to this embodiment.

In an additional embodiment, the bisphosphonate is ibandronate, and the pharmaceutically effective dose is typically about 0.5 to about 6 mg, preferably, about 1 to about 5 mg, more preferably about 1.5 to about 4 mg, and more preferred still about 2 to about 3 mg per day. Superior results are contemplated where the dosage of ibandronate is about 2.5 mg daily. The pharmaceutically effective amounts for weekly or monthly administration are contemplated to be approximately the daily effective amount multiplied by the dosing interval. It is contemplated that a pharmaceutically effective dose of ibandronate of about 100 to about 200 mg/month or about 125 to about 175 mg/month, or about 150 mg/month will be particularly useful. The daily, weekly, or monthly pharmaceutically effective amounts of bisphosphonate described elsewhere herein are equally applicable to this embodiment.

In one embodiment, a single dosage form, i.e., a tablet, capsule, pill, etc., comprises an effective amount of OMYA-Cal® USP-10-AZ calcium carbonate (or any other highly bioavailable calcium carbonate described herein) and a pharmaceutically effective amount of a bisphosphonate, preferably selected from the group consisting of alendronate, risedronate, and ibandronate. In another embodiment, a single dosage form is provided comprising from about from 100 to about 1,000 mg of OMYA-Cal® USP-10-AZ calcium carbonate and about 5 to about 15 mg of alendronate, or about 1 to about 10 mg risedronate, or about 0.5 to about 6 mg ibandronate, or combinations thereof. Preferably, the dosage form also includes vitamin D in any amount described herein. The dosage from may optionally include one or more pharmaceutically acceptable excipients.

In one embodiment contemplated to be especially useful, a composition for treating osteoporosis will comprises about 5 mg, 10 mg, 35 mg, 40 mg, or 70 mg of alendronate or about 5 mg to about 35 mg of risedronate, or about 2.5 mg to about 100 mg or 150 mg of ibandronate, and an effective amount of OMYA-Cal® USP-10-AZ calcium carbonate, or any other calcium carbonate powder described herein, and vitamin D, and optionally, one or more pharmaceutically acceptable excipients. The terms alendronate, risedronate, and ibandronate are intended to include pharmaceutically acceptable salts thereof, including alendronate sodium, risedronate sodium, ibandronate sodium, and the like.

In another embodiment, the calcium carbonate powders according to the invention are included in a multi-vitamin comprising one or more active agents selected from the group consisting of vitamin A, vitamin C, vitamin D, vitamin E, vitamin K, thiamin, riboflavin, niacin, vitamin $B_6$, folic acid, vitamin $B_{12}$, biotin, pantothenic acid, calcium, phosphorus, iodine, magnesium, zinc, selenium, copper, manganese, chromium, molybdenum, chloride, potassium, boron, nickel, silicon, vanadium, lutein, lycopene, iron, tin, *ginseng* root, and *ginkgo biloba* leaf, to name a few.

The multi-vitamin will typically comprise from about 10 mg to about 2,000 mg, more typically from about 25 mg to about 1,000 mg, preferably from about 50 mg to about 750 mg, and more preferred still, from about 100 mg to about 500 mg of calcium carbonate according to the invention, preferably OMYA-Cal® USP-10-AZ calcium carbonate powder. In one embodiment, the multi-vitamin will comprise about 385-420 mg of calcium carbonate and will preferably be capable of delivering at least about 50 mg, at least about 55 mg, at least about 60 mg, at least about 70 mg, at least about 80 mg, or at least about 90 mg of absorbable elemental calcium, by which is meant that the specified dose of elemental calcium is actually absorbed through the intestine based on a population average, rather than on an individual basis. In another embodiment, the multi-vitamin will comprise about 420-470 mg of calcium carbonate and will preferably be capable of delivering at least about 60 mg, at least about 65 mg, at least about 70 mg, at least about 75 mg, at least about 80 mg, or at least about 85 mg of absorbable elemental calcium. In another embodiment, the multi-vitamin will comprise about 470-520 mg of calcium carbonate and will preferably be capable of delivering at least about 70 mg, at least about 75 mg, at least about 80 mg, at least about 85 mg, at least about 90 mg, or at least about 95 mg, or at least about 100 mg of absorbable elemental calcium.

The multi-vitamin may comprise one or more vitamins selected from the group consisting of:
between 1 and about 35,000 IU of vitamin A;
between 1 and about 1,000 mg of vitamin C;
between 1 and about 4,000 IU of vitamin D;
between 1 and about 450 IU of vitamin E;
between 1 and about 250 mcg of vitamin K;
between 1 and about 15 mg of vitamin B-1 (thiamin);
between 1 and about 17 mg of vitamin B-2 (riboflavin);
between 1 and about 200 mg of vitamin B-3 (niacin);
between 1 and about 100 mg of vitamin B-5 (pantothenic acid);
between 1 and about 30 mg of vitamin B-6 (pyridoxine);
between 1 and about 4,000 mcg of vitamin B-9 (folic acid);
between 1 and about 250 mcg of vitamin B-12 (cobalamin); and
between 1 and about 1,000 mcg of vitamin H (biotin);
and combinations thereof.

The multi-vitamin may also comprise one or more minerals selected from the group consisting of:
between 1 and about 180 mg of iron;
between 1 and about 1,100 mg of phosphorous;
between 1 and about 1,500 mcg of iodine;
between 1 and about 4,000 mg of magnesium;
between 1 and about 150 mg of zinc;
between 1 and about 600 mcg of selenium;
between 1 and about 20 mg of copper;
between 1 and about 20 mg of manganese;
between 1 and about 2,000 mcg of chromium; and
between 1 and about 750 mcg of molybdenum;
between 0.001 and about 0.1 mg of tin;
between 1 and about 100 mcg of vanadium;
between 0.5 and 50 mcg of nickel;
and combinations thereof.

The multi-vitamin tablets may be of any volume, but are preferably sized to correspond to any of the tablet volumes or ranges of volumes specified herein, and in particular the volumes provided in Example 3.

Based on the discovery that the inventive calcium carbonate powders ("enhanced absorption calcium carbonate") have increased bioavailability, less enhanced absorption calcium carbonate, on a weight or volume basis, will be required to provide the same level of absorbable elemental calcium (i.e., the average amount actually absorbed through the intestine, as described herein) as provided by conventional calcium carbonate powders. Therefore, it will be seen that it is possible to reformulate an existing calcium supplement tablet (chewable or swallowable) by replacing the conventional calcium carbonate in such product with the enhanced absorption calcium carbonate according to the invention, e.g., on an equal weight basis, to boost the amount of absorbable elemental calcium delivered by the product. In some embodiments, the amount of absorbable elemental calcium may be increased by at least about 5%, at least about 7.5%, at least about 10%, at least about 15%, at least about 20%, or more without increasing the size of the tablet. It is contemplated that the boost in absorbable elemental calcium will provide a significant advantage in the marketplace as consumers are desirous of obtaining the maximum dosage of elemental calcium possible per tablet, particularly since the size of the tablet does not need to be increased to achieve the enhancement in absorbable elemental calcium.

Thus, in one embodiment of the invention, a method for reformulating a calcium supplement is provided comprising: (i) providing a calcium supplement comprising calcium carbonate powder ("first calcium carbonate powder"); and (2) reformulating said calcium supplement by replacing all or a portion of said first calcium carbonate powder in said calcium supplement with enhanced absorption calcium carbonate powder having an absorption efficiency greater than that of said first calcium carbonate powder. Preferably, the enhanced absorption calcium carbonate will have an absorption efficiency at least about 5% greater, at least about 7.5% greater, at least about 10% greater, at least about 15% greater, or at least about 20% greater than said first calcium carbonate powder. By "first calcium carbonate powder" is meant a calcium carbonate powder previously included in said calcium supplement, preferably but not necessarily, a commercially marketed calcium supplement, prior to the step of reformulating. In one embodiment, the step of reformulating will comprise replacing some or all of a first calcium carbonate powder having a median particle size greater than 15 µm or less than 10 µm with any of the enhanced absorption calcium carbonate powders according to the invention, in particular with OMYA-Cal® USP-10-AZ calcium carbonate powder. In another embodiment, the step of reformulating will comprise replacing some or all of a first calcium carbonate powder comprising OMYA-Cal® USP-15-AZ (Omya, Inc.), a ground mined limestone calcium carbonate powder having a median particle size of about 16 µm (typical range~15 to about ~17 due to error of measurement), with an enhanced absorption calcium carbonate powder, such as OMYA-Cal® USP-10-AZ calcium carbonate powder. In one embodiment, the first calcium carbonate powder will be replaced by the enhanced absorption calcium carbonate on an equal weight basis, and preferably all of the first calcium carbonate powder will be replaced. The size of the calcium supplement may remain the same, or substantially the same (e.g., with ±5%, or ±2.5% of the original volume), or may even advantageously be reduced without decreasing, while preferably increasing, the amount of absorbable elemental calcium as compared to the supplement prior to reformulation.

In a related embodiment, the calcium supplement may be reformulated according to the preceding method by removing a portion or all of the first calcium carbonate powder, but replacing therewith an amount of enhanced absorption calcium carbonate that is less than the amount of said first calcium carbonate powder removed on a weight basis. In this manner, a tablet which is smaller than the original supplement can be made which nevertheless provides the same, or ever greater, absorbable elemental calcium per tablet. In accordance with this embodiment, it may be desirable to replace 6, 7, or 8 parts by weight of the first calcium carbonate powder with 5 parts by weight of enhanced absorption calcium carbonate according to the invention.

In another embodiment, a method is provided comprising: (i) providing a calcium supplement marketed under a brand name, said calcium supplement comprising calcium carbonate powder ("first calcium carbonate powder"); (2) reformulating said calcium supplement by replacing all or a portion of said first calcium carbonate powder in said calcium supplement with enhanced absorption calcium carbonate powder having an absorption efficiency greater than that of said first calcium carbonate powder; and (3) marketing said reformulated calcium supplement under said same brand name. By "brand name" is meant, without limitation, a trademark, trade name, or the like (e.g., "Caltrate®") and by "same brand name" is meant that at least one trademark, trade name, etc. will be in common between the original and reformulated products. This method may find particular utility for any brand of calcium supplement which is widely recognized in the marketplace by consumers. For example, a manufacturer may not wish to substantially change the tablet size, calcium carbonate content, etc., due to the existing goodwill associated with an established commercial product, but nevertheless may wish to reformulate the product and market it under the same brand name but with an "improved absorption" claim or the like. It is contemplated that sales of calcium supplements under an existing brand name will be improved by the ability to make such a claim, regardless of whether the tablets remain substantially the same size, or decrease, after reformulation.

Special mention may be made of the use of the foregoing methods to reformulate any calcium supplement comprising about 600 mg (±manufacturing tolerances or customary overages) of elemental calcium, as this is a standard dosage form for commercially available calcium supplements because such tablets, when taken twice daily, provide the Adequate Intake (AI) of 1,200 mg elemental calcium set by the Institute of Medicine of the National Academy of Sciences. However, in embodiments where all of the conventional calcium carbonate in such a calcium supplement is replaced with enhanced absorption calcium carbonate having an absorption efficiency of about 50%, it is surprisingly seen that the reformulated tablet will provide the AI of 1,000 mg of elemental calcium when taken once daily. Thus, the reformulated product will have the advantage of being flexibly marketed as a twice-a-day tablet (e.g., to achieve AIs of 1,200 mg or 1,300 mg) or as a once-a-day tablet to achieve the AI of 1,000 mg recommend for the large population segment between 19 and 50 years old.

The ability to retain or even boost the amount of absorbable elemental calcium while removing or keeping constant the amount of calcium carbonate in a tablet is contemplated to also find utility in formulating or reformulating (e.g., according to the foregoing methods) chewable calcium supplement or chewable antacids comprising calcium carbonate. One drawback to such chewable products is the perception of chalky taste commonly associated therewith. Since less enhanced absorption calcium is required on a weight basis to achieve the same level of absorbable elemental calcium as compared to a conventional calcium carbonate powder, more volume in a tablet is thus provided for the inclusion of additional ingredients which can serve to mask the chalky taste, such as sweeteners (natural or artificial), flavorants, and components which modify the texture of the product in the mouth during chewing. Thus, it is possible to formulate superior tasting chewable tablets comprising enhanced absorption calcium carbonate without changing the size of the tablet, and preferably with a reduction in tablet size. A chewable calcium supplement or antacid according to the invention will typically comprise from about 2,000 mg to about 4,000 mg of enhanced absorption calcium carbonate, more typically between about 2,500 mg and about 3,500 mg, including a representative embodiment of a chewable tablet comprising about 3,000 mg of enhanced absorption calcium carbonate and preferably further including vitamin D in any amount specified herein, including without limitation, about 1,000 I.U. per tablet. The superior tasting chewable tablets will have a reduced perception of chalkiness, as determined by consumer testing or expert evaluation, as compared to a chewable tablet of the identical size which delivers substantially the same amount of absorbable elemental calcium provided by conventional calcium carbonate.

In one embodiment of the invention, a product is provided comprising: (a) a container comprising a plurality of tablets for dietary calcium supplementation, the tablets comprising an amount of enhanced absorption calcium carbonate powder sufficient to provide the AI of 1,000, 1,200, or 1,300 mg and vitamin D; and (b) instructions on the product labeling, packaging, or insert, for the use of the tablets in a single daily dose to achieve a full day requirement of calcium.

In another embodiment of the invention, a method is provided for increasing the absorbable calcium content of a calcium carbonate containing multi-vitamin product in tablet from, without requiring a change the size of the tablet, comprising replacing a portion or all of the conventional calcium carbonate in said multi-vitamin tablet with any of the inventive enhanced absorption calcium carbonate powders according to the invention, on an equal weight basis. In another embodiment of the invention, a method is provided for reducing the size (volume) of a conventional calcium carbonate containing multi-vitamin product, without substantially changing the amount (e.g., within ±5%) of absorbable elemental calcium in the product, comprising replacing a portion or all of the calcium carbonate in said multi-vitamin with any of the inventive enhanced absorption calcium carbonate powders according to the invention, on an less than equal weight basis, preferably by removing about 6-7 parts conventional calcium carbonate for each 5 parts enhanced absorption calcium carbonate added.

In one interesting variant, the calcium carbonate powder is added to chocolate or chocolate compound coating as described in U.S. patent application Ser. No. 11/437,371, the disclosure of which is hereby incorporated by reference. Calcium fortified chocolate or chocolate compounds coating is provided by substituting the calcium powders described herein for those of U.S. patent application Ser. No. 11/437,371. Advantageously, preferred calcium carbonate powders of the present invention will have median or mean particle sizes suited to formulating the composition of U.S. patent application Ser. No. 11/437,371. Preferred compositions according to this variant will comprise at least about 10%, at least about 15%, at least about 20%, or at least about 25% by weight calcium carbonate, preferably OMYA-Cal® USP-10-AZ calcium carbonate powder, dispersed homogenously in a chocolate or chocolate compound coating matrix, and optionally will comprise vitamin D wherein each dosage size or serving size may comprise any amount of vitamin D specified herein.

The calcium carbonate powders may also be used to enhance the dietary calcium content of bread products using the methods and ingredients described in U.S. Pat. Nos. 7,166,313 and 7,169,417 to Dibble et al., and U.S. patent application Ser. Nos. 11/462,560, and 11/462,581, the disclosures of which are hereby incorporated by reference. In one variant, a calcium additive comprises OMYA-Cal® USP-10-AZ calcium carbonate powder and citric acid in an intimate admixture in the ratios described in U.S. patent application Ser. Nos. 11/462,560 and 11/462,581, and optionally vitamin D. These additives will be useful for enriching the calcium content of baked goods, and the like. One embodiment of the present invention therefore is a composition for baking comprising a mixture of dough ingredients and a calcium additive comprising and intimate admixture of OMYA-Cal® USP-10-AZ or any suitable calcium carbonate according to the invention. In one embodiment, a baked product, particularly a leavened bread product, such as a hamburger bun, comprising OMYA-Cal® USP-10-AZ in any of the amounts described in U.S. Pat. Nos. 7,166,313 and 7,169,417 to Dibble et al., and U.S. patent application Ser. Nos. 11/462,560, and 11/462,581 is provided.

In other embodiments, the powders may be delivered neat, as slurries, tube-fed diets, or the like.

EXAMPLES

In the following examples, the following designations are used to refer to the specified commercially available calcium carbonate powders:

"Calcium Carbonate[16]" refers to the calcium carbonate powder having a median particle size of about 16 microns available from OMYA, Inc. under the trademark OMYA-Cal® USP-15-AZ. OMYA-Cal® USP-15-AZ is ground mined limestone calcium carbonate.

"Calcium Carbonate[12]" refers to the calcium carbonate powder having a median particle size of about 12 microns available from OMYA, Inc. under the trademark OMYA-Cal® USP-10-AZ. OMYA-Cal® USP-10-AZ is ground mined limestone calcium carbonate.

"Calcium Carbonate[5]" refers to the calcium carbonate powder having a median particle size of 4.6 microns available from OMYA, Inc. under the designation V-70. The V-70 product is a precipitated calcium carbonate powder comprising rose-shaped crystals.

"Calcium Carbonate[2]" refers to the calcium carbonate powder having a median particle size of about 2 microns available from Minerals Technologies Inc. under the trademark ALBAGLOS PCC® (advertised as having a particle size of 0.8 microns). The ALBAGLOS PCC® powder is a precipitated calcium carbonate product having prismatic and cubic shaped crystals.

"Calcium Hydroxide[5]" refers to the calcium hydroxide powder having a median particle size of about 5 microns available OMYA, Inc. This material comprises rhomboid shaped crystals of calcium hydroxide.

"Calcium mix" refers to a 1:1 mixture by weight of Calcium Hydroxide[5] and Calcium Carbonate[12]. The calcium mix has an median particle size of about 15 microns (14.8 microns).

Except in the case of Calcium Hydroxide[5], the foregoing median particle sizes are not those advertised by the manufacturer but rather reflect median particle sizes as determined using a Coulter Particle Size Analyzer as described in Example 2. All values represent the median particle size on a volume basis.

Example 1

The effects of calcium source, vitamin D, and L-lysine on calcium retention and bone quality was investigated in the rat model according to the procedure described in Zafar et al., "Nondigestible Oligosaccharides Increase Calcium Absorption and Suppress Bone Resorption in Ovariectomized Rats," *J. Nutrition*, 123:399-402, 2004, the disclosure of which is hereby incorporated by reference.

One hundred forty-four 3-week old Sprague-Dawley rats were randomized into nine groups (Groups 1-9) as listed in Table 1, with sixteen rats in each group, and twenty five rats were randomized into six groups (Groups 10-15) as listed in Table 2. For one week all rats (Groups 1-15) were fed a vitamin D-free AIN93-G control diet. At the end of week one (4 weeks of age) the 144 rats (Groups 1-9) were switched to the study diets adapted from the AIN93-G diet but containing the calcium, vitamin D, and/or L-lysine quantities listed in Table 1 and the 25 rats were switched to AIN96-G diets including the calcium, vitamin D, and/or L-lysine quantities listed in Table 2. At this time five rats from Group 10 were sacrificed and serum was aliquoted for vitamin D assay.

During the first week of feeding all rats were placed in metabolic cages for two days to determine calcium balance according to the procedure set forth in Zafar et al., *J. Nutrition*, 123:399-402, 2004. Six rats from each groups received $^{45}$Ca IP injections. At the end of the balance study, 10 rats from the Vitamin D study were sacrificed: 5 rats from Group 10 and 1 rat from each of Groups 11-15. After eight weeks on the test diets, a two-day balance study was again conducted on ten rats from each groups according to the same procedure. At the end of the balance study, 10 rats from the Vitamin D status study were sacrificed: 5 rats from Group 10 and 1 rat from each of Groups 11-15.

During week 10, all rats were sacrificed and both femurs and tibias were harvested. One femur and tibia from each rat were used for weight and length, bone breaking and calcium determination. Blood was collected from a randomly selected subset of rats for Vitamin D status as follows: 5 rats from Group 1 and one rat from each of Groups 2, 4, 6, 8 and 9.

Calcium analysis of diet, bones, feces, urine was determined by atomic absorption spectrophotmetry (AAnalyst 300, Perkin Elmer, Shelton, Conn.). Percent calcium absorption was measures as (intake−feces)/intake*100. Bone Strength was determined by a three point bending test (TA-XT2i, Texture Technologies, Corp, Scarsdale N.Y.), bone geometry was determined by μCT 40 (Scanco Medical, Bassersdorf, Switzerland), and bone density was determined by underwater weighing, DXA (Lunar, Madison Wis.). Serum 25 OH D levels were measure by Gamma-B 25-Hydroxy Vitamin D RIA (IDS, Inc).

Results: Calcium Balance

Calcium Balance data are provided in Tables 3 and 4. The data in Table 3 shows the effect of each diet on two day calcium balance in four week old rats after two days on the prescribed diet. The data in Table 4 shows the effect of each diet on two day calcium balance in twelve-week old rats after eight weeks on the prescribed diet. The values represent the group mean for all rats on the indicated diet (±SEM). The different superscripts within the columns of Tables 3 and 4 represent statistically significant differences at a 95% confidence level (p<0.05).

TABLE 1

Particle Size Study Diets

| Diet | Group | Rats (N) | Calcium Source | Median (μm) | Calcium (mg) | Vitamin D (I.U.) | L-Lysine (mg) |
|---|---|---|---|---|---|---|---|
| 1 | 1 | 16 | Calcium Carbonate[12] | 12 | 600 | — | — |
| 2 | 2 | 16 | Calcium Carbonate[12] | 12 | 600 | 400 | — |
| 3 | 3 | 16 | Calcium Carbonate[12] | 12 | 600 | 400 | 100 |
| 4 | 4 | 16 | Calcium Carbonate[12] | 12 | 600 | 400 | 200 |
| 5 | 5 | 16 | Calcium Carbonate[16] | 16 | 600 | 400 | — |
| 6 | 6 | 16 | Calcium Carbonate[5] | 5 | 600 | 400 | — |
| 7 | 7 | 16 | Calcium Carbonate[2] | 2 | 600 | 400 | — |
| 8 | 8 | 16 | Calcium Hydroxide[5] | 5 | 600 | 400 | — |
| 9 | 9 | 16 | Calcium Mix | 15 | 600 | 400 | — |

TABLE 2

Vitamin D Status Study Diets

| Diet | Group | Rats (N) | Calcium Source | Median (μm) | Calcium (mg) | Vitamin D (I.U.) | L-Lysine (mg) |
|---|---|---|---|---|---|---|---|
| 1 | 10 | 15 | Calcium Carbonate[12] | 12 | 600 | — | — |
| 2 | 11 | 2 | Calcium Carbonate[12] | 12 | 600 | 400 | — |
| 4 | 12 | 2 | Calcium Carbonate[12] | 12 | 600 | 400 | 200 |
| 6 | 13 | 2 | Calcium Carbonate[5] | 5 | 600 | 400 | — |
| 8 | 14 | 2 | Calcium Hydroxide[5] | 5 | 600 | 400 | — |
| 9 | 15 | 2 | Calcium Mix | 15 | 600 | 400 | — |

TABLE 3

| Diet | Ca Intake/2 d (mg) | Ca Absorption (%) | Ca Balance (mg/2 d) |
|---|---|---|---|
| 1 | 107.6$^{abcd}$ (5.4) | 86.6$^b$ (1.6) | 92.9$^{bc}$ (5.6) |
| 2 | 129.3$^a$ (9.7) | 92.1$^{ab}$ (1.4) | 118.9$^a$ (9.8) |
| 3 | 94.1$^{cde}$ (10.3) | 85.7$^b$ (5.7) | 86.4$^{bc}$ (10.1) |
| 4 | 102.4$^{cde}$ (10.3) | 96.1$^a$ (4.1) | 93.1$^{bc}$ (10.1) |
| 5 | 85.5$^e$ (8.5) | 94.3$^a$ (1.2) | 78.9$^c$ (8.4) |
| 6 | 126.9$^a$ (8.9) | 92.7$^{ab}$ (1.3) | 117.5$^a$ (9.1) |
| 7 | 87.8$^{de}$ (5.3) | 90.2$^{ab}$ (1.9) | 78.5$^c$ (5.5) |
| 8 | 115.0$^{abc}$ (5.3) | 91.1$^{ab}$ (1.3) | 102.9$^{ab}$ (4.9) |
| 9 | 118.4$^{ab}$ (3.8) | 92.9$^{ab}$ (1.3) | 108.1$^{ab}$ (3.7) |

Figure 3:
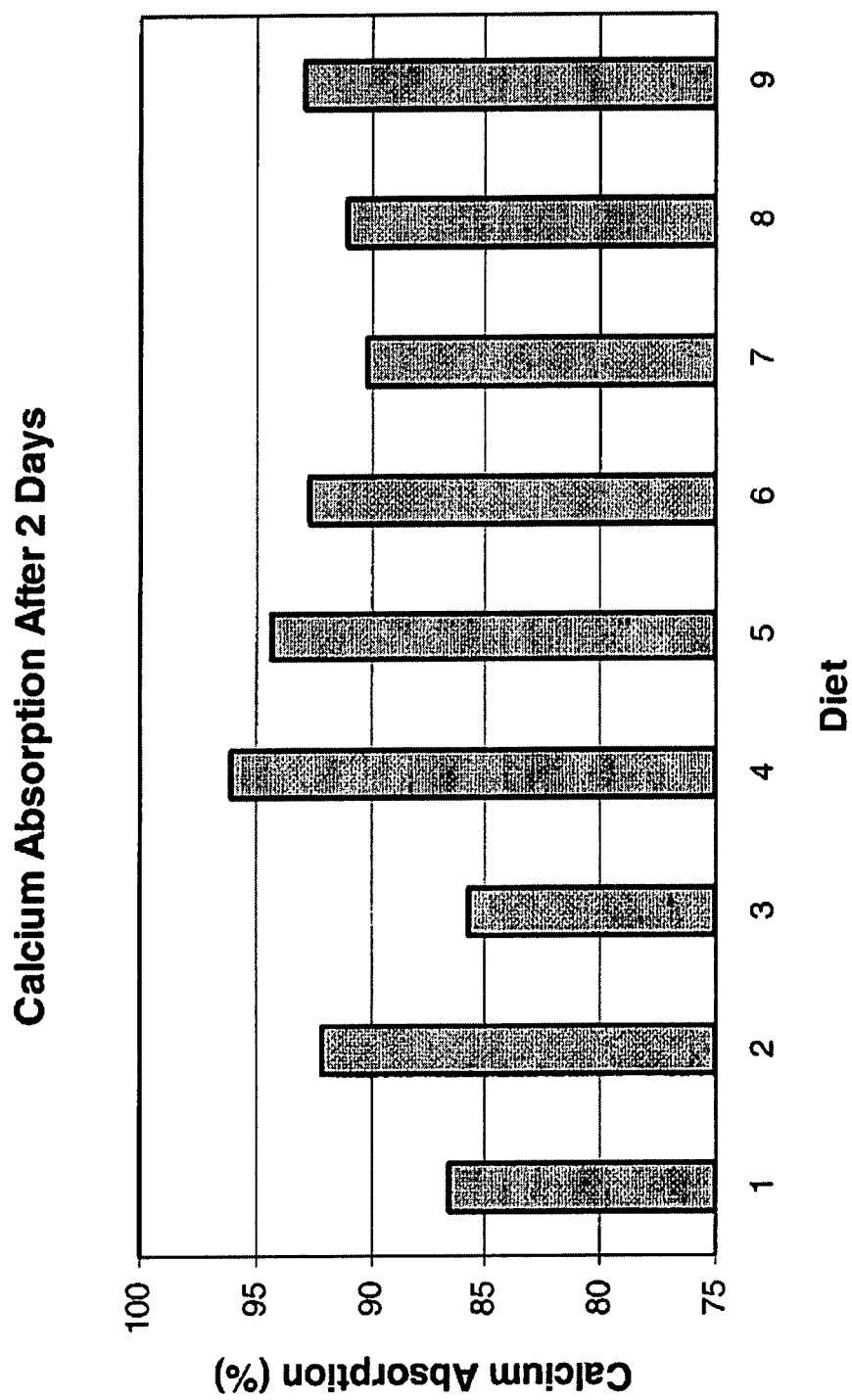
FIG. 3 shows the effect of the diets listed in Tables 1 and 2, comprising different calcium sources, vitamin D status, and L-lysine status, on the absorption efficiency in rats after two days of calcium supplementation.
Figure 4:
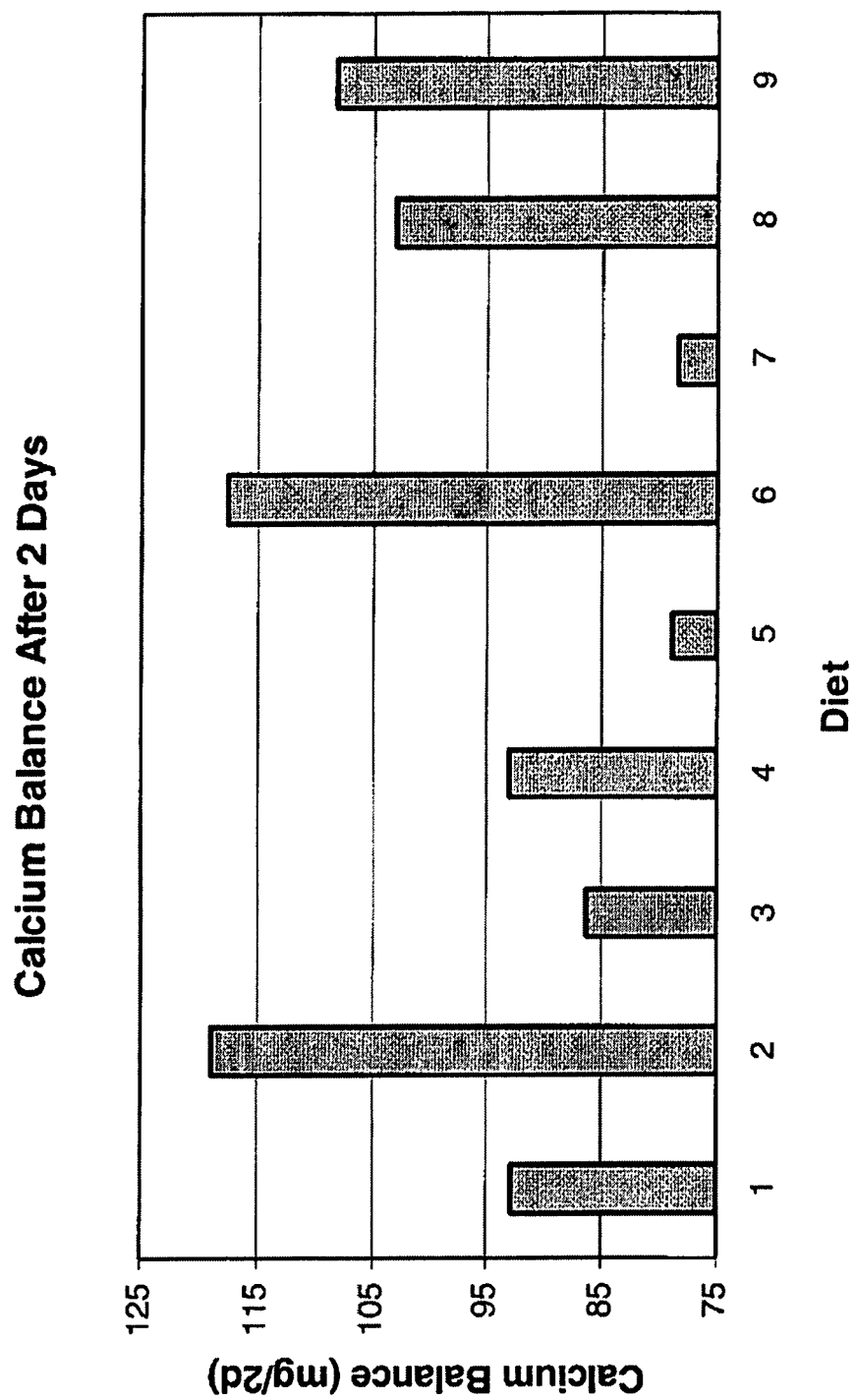
FIG. 4 shows the effect of the diets listed in Tables 1 and 2, comprising different calcium sources, vitamin D status, and L-lysine status, on the calcium balance in rats after two days of calcium supplementation.

The calcium absorption efficiency data and calcium balance data of Table 3 are plotted in FIGS. 3 and 4, respectively. It is notable that after only two days on the diet, rats fed Calcium Carbonate[12] plus 400 IU of Vitamin D (Diet 2) showed a significantly higher calcium balance than rats fed Vitamin D deficient diets of Calcium Carbonate[12] (Diet 1). This finding is in accordance with other studies which have demonstrated the importance of vitamin D in calcium absorption. The effect of L-lysine on calcium balance appears to be negative, as both Diet 3 (100 mg L-lysine) and Diet 4 (200 mg L-lysine) produced significantly lower calcium balance than Diet 2 after two days. However, significance was observed with the 200 mg L-lysine diet as compared to the 100 mg L-lysine diet on the basis of absorption efficiency although this difference had no impact on calcium balance. The Vitamin D fortified diet of Calcium Carbonate[12] (Diet 2) also produced a statistically significant improvement in calcium balance over the Vitamin D sufficient diets of Calcium Carbonate[16] (Diet 5) and Calcium Carbonate[2] (Diet 7).

Comparable data after eight weeks on the specified diets is provided in Table 4. The eight week data is considered to be more meaningful as it is likely to account for any adaptive effects of chronic feeding. For example, after eight weeks no significance is seen between the two L-lysine diets for either calcium absorption efficiency or calcium balance. In fact, L-lysine shows a statistically significant (p<0.05) negative effect on both percentage calcium absorption and calcium balance as compared to Diet 2 when fed at a level of 200 mg (Diet 4).

TABLE 4

| Diet | Ca Intake/2 d (mg) | Ca Absorption (%) | Ca Balance (mg/2 d) |
|---|---|---|---|
| 1 | 117.5$^{cd}$ (4.7) | 27.9$^d$ (3.6) | 32.8$^c$ (5.4) |
| 2 | 139.3$^{ab}$ (5.1) | 51.4$^a$ (2.9) | 69.9$^a$ (5.3) |
| 3 | 125.7$^{cd}$ (5.5) | 47.9$^{ab}$ (4.1) | 60.8$^{ab}$ (7.2) |
| 4 | 123.3$^{bcd}$ (6.6) | 40.4$^{bc}$ (3.3) | 47.6$^{bc}$ (4.5) |
| 5 | 113.6$^d$ (4.6) | 36.1$^{cd}$ (2.5) | 39.0$^c$ (3.8) |
| 6 | 113.7$^d$ (5.7) | 37.8$^{bcd}$ (5.3) | 43.8$^{bc}$ (7.1) |
| 7 | 110.8$^d$ (3.8) | 39.3$^{bc}$ (2.5) | 41.8$^{bc}$ (3.3) |
| 8 | 132.2$^{abc}$ (4.3) | 44.3$^{abc}$ (3.8) | 56.9$^{ab}$ (5.6) |
| 9 | 147.1$^a$ (9.9) | 44.0$^{abc}$ (4.7) | 66.2$^a$ (9.7) |

The eight-week data in Table 4 also confirms the role of Vitamin D in improving calcium absorption as the amount absorbed on a percentage basis increased significantly (p<0.05) from 27.9% in the Vitamin D deficient diet (Diet 1) to 51.4% in the comparable Vitamin D sufficient diet (Diet 2). Similarly, the calcium balance increased significantly (p<0.05) from 32.8% in the Vitamin D deficient diet (Diet 1) to 69.9% in the sufficient Vitamin D diet (Diet 2).

Figure 5:
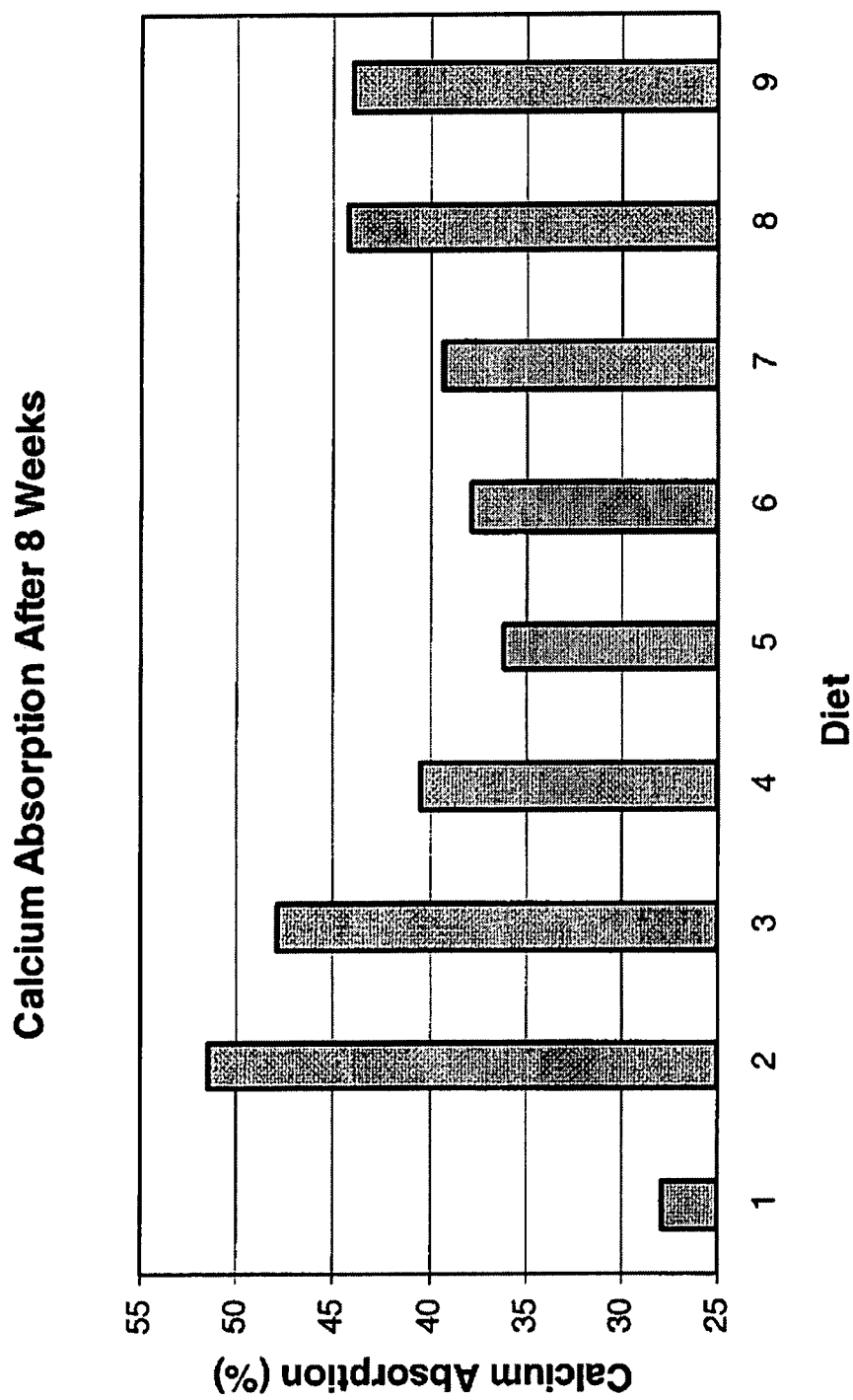
FIG. 5 shows the effect of the diets listed in Table 1 and 2, comprising different calcium sources, vitamin D status, and L-lysine status, on the absorption efficiency in rats after eight weeks of calcium supplementation.
Figure 6:
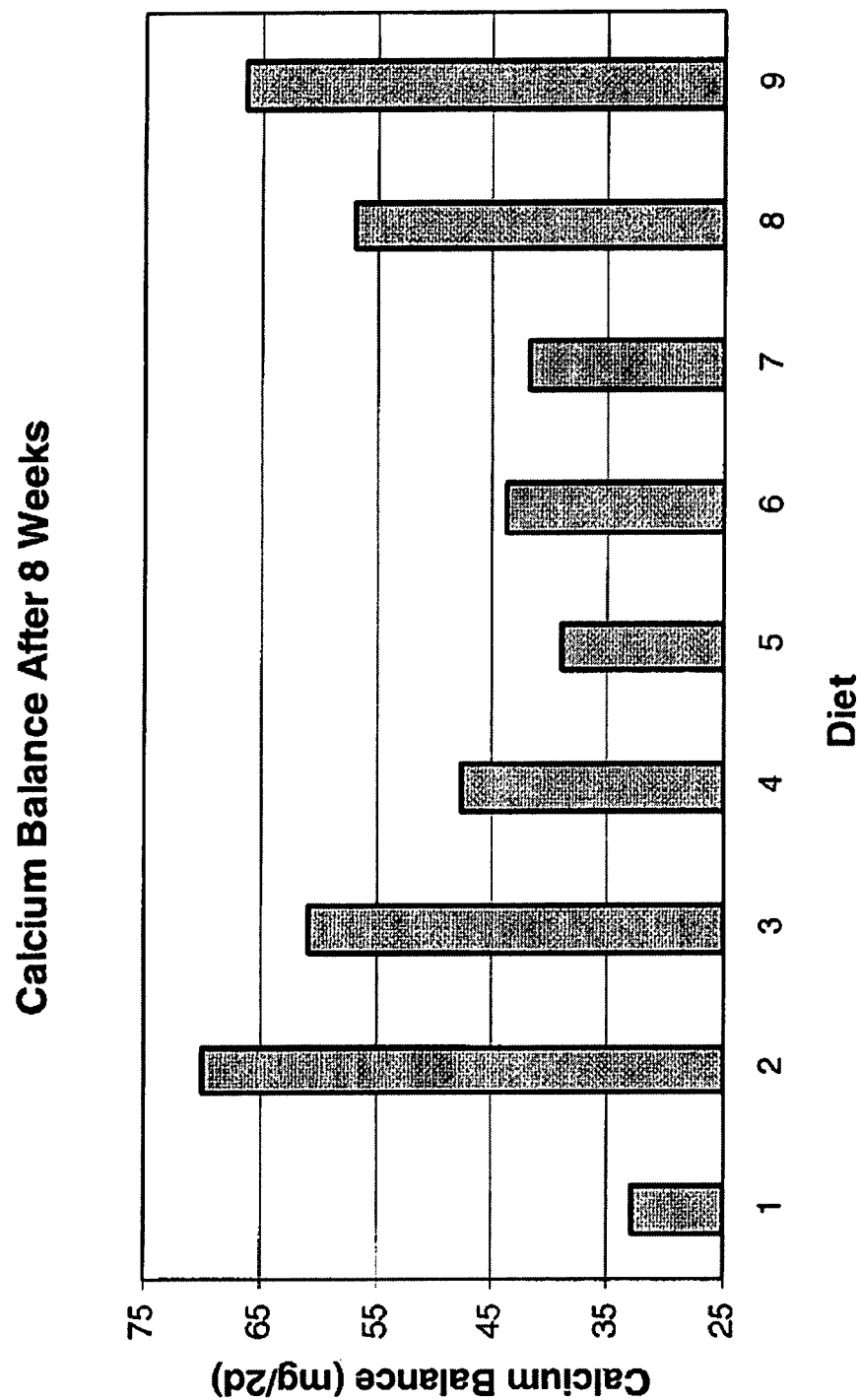
FIG. 6 shows the effect of the diets listed in Table 1 and 2, comprising different calcium sources, vitamin D status, and L-lysine status, on the calcium balance in rats after eight weeks of calcium supplementation.

Most notably, rats fed Calcium Carbonate[12] plus 400 IU of Vitamin D (Diet 2) showed the highest percentage absorption of calcium and calcium balance after eight weeks. A significantly (p<0.05) higher percentage calcium absorption and calcium balance was achieved with Diet 2 than with any other form of calcium carbonate, i.e., Diets 5, 6, and 7. Rats fed Diet 2 had a 42.4% advantage in calcium absorption efficiency as compared to rats fed Diet 5 (p<0.05). The effect of each diet on calcium absorption after eight weeks on the diet is shown in FIG. 5. The effect of diet on calcium balance after eight weeks on the prescribed diets, shown in FIG. 6, parallel the effects of diet on absorption.

Figure 7:
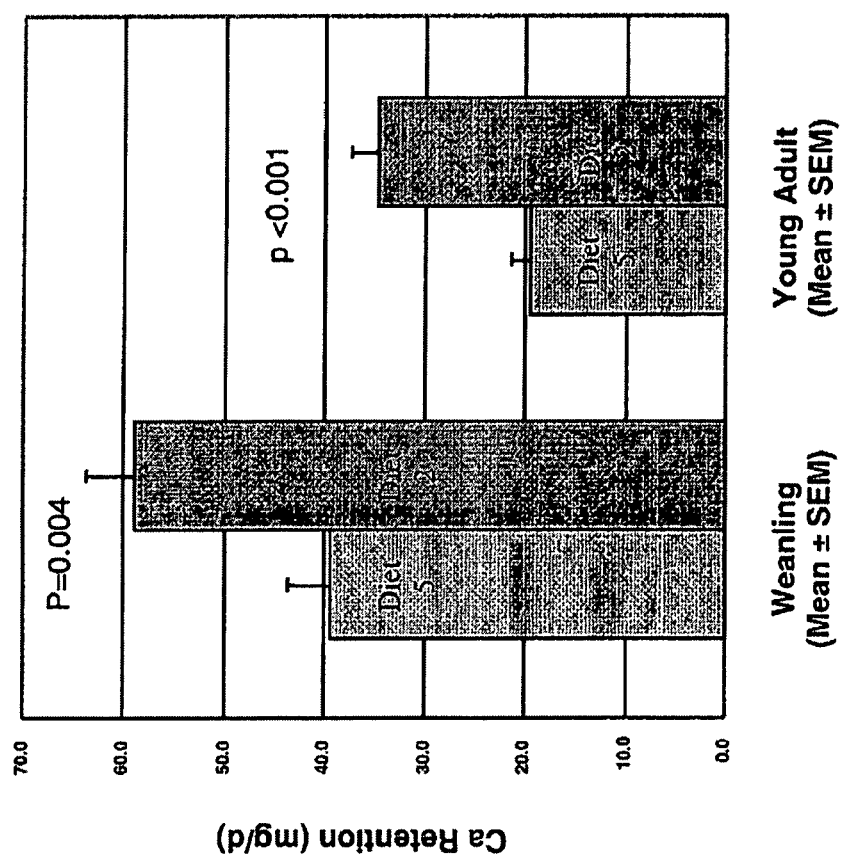
FIG. 7 compares the calcium retention in rats after two days (weanlings) and after eight weeks (young adults) on Diets 2 and 5 listed in Tables 1 and 2.

FIG. 7 compares calcium retention between rats fed Diet 2 versus rats fed Diet 5, which notably is representative of the national leading brand, after two weeks on the diet (weanling rats) and eight weeks on the diet (young adults). In weanling rats, the differences are significant at p=0.004. In young adult rats, the differences are significant at p<0.001. This data may be projected to humans to estimate that an adolescent female will retain sufficiently more calcium to increase bone mass by at least 4% over a one year period and potentially more than 8% over a two year period, relative to other forms of calcium carbonate, by consuming Calcium Carbonate[12] plus 400 IU of Vitamin D Results: Bone-Breaking Table 5 provides the means values (±SEM) for the right femur dimensions, weight, and bone breaking peak force after eight weeks on the diets shown in Tables 1 and 2.

TABLE 5

| Group | Length (mm) | Width (mm) | Dry Weight (g) | Underwater Weight (g) | Peak Force (g) | Gradient |
|---|---|---|---|---|---|---|
| 1 | 33.53 (0.29) | 3.01 (0.13) | 0.80 (0.02) | 0.24 (0.01) | 9429$^a$ (623) | 11702 (1686) |
| 2 | 33.85 (0.21) | 3.11 (0.02) | 0.88 (0.01) | 0.26 (0.00) | 10993$^b$ (247) | 10462 (1825) |
| 3 | 33.67 (0.16) | 3.06 (0.03) | 0.82 (0.01) | 0.26 (0.00) | 10776$^{ab}$ (206) | 14754 (1414) |
| 4 | 33.72 (0.29) | 3.06 (0.03) | 0.85 (0.02) | 0.26 (0.01) | 10207$^{ab}$ (266) | 12818 (1469) |
| 5 | 33.65 (0.22) | 3.07 (0.03) | 0.85 (0.02) | 0.26 (0.01) | 10218$^{ab}$ (278) | 13480 (1822) |
| 6 | 33.80 (0.20) | 3.06 (0.02) | 0.85 (0.02) | 0.26 (0.01) | 10398$^{ab}$ (265) | 12707 (1864) |
| 7 | 33.61 (0.20) | 3.06 (0.03) | 0.85 (0.02) | 0.26 (0.00) | 10697$^{ab}$ (264) | 13252 (1707) |
| 8 | 33.72 (0.24) | 3.07 (0.04) | 0.90 (0.02) | 0.26 (0.00) | 10320$^{ab}$ (205) | 12745 (1567) |

TABLE 5-continued

| Group | Length (mm) | Width (mm) | Dry Weight (g) | Underwater Weight (g) | Peak Force (g) | Gradient |
|---|---|---|---|---|---|---|
| 9 | 33.70 (0.17) | 3.04 (0.03) | 0.84 (0.02) | 0.26 (0.01) | 10888[b] (799) | 12657 (1631) |

Figure 8:
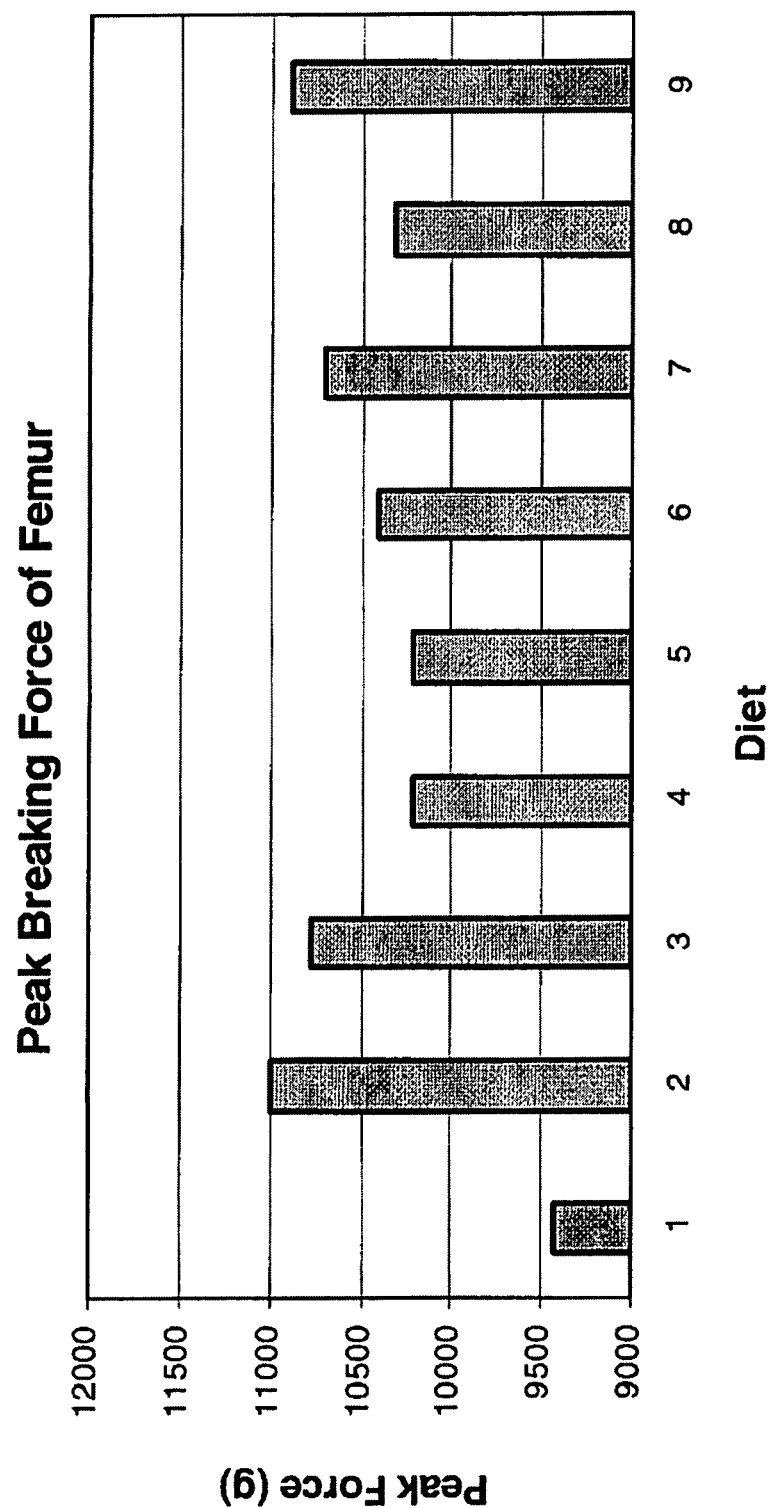
FIG. 8 shows the effect of the diets listed in Table 1 and 2, comprising different calcium sources, vitamin D status, and L-lysine status, on the peak break force of femurs from rats after eight weeks of calcium supplementation.

The different superscripts within the peak break force column represent statistically significant differences at a 95% confidence level (p<0.05). There were significant differences in peak bone breaking force of the femur (p=0.0251): peak breaking force of femurs of rats on Diet 1 (vitamin D deficient) was significantly lower than for rats on Diet 2 (the same calcium source plus Vitamin D) or for rats on Diet 9. At a 90% confidence interval (p<0.10) the differences in peak bone breaking force of the femur between rats on Diets 2 and 5 were significant. The significance between Diets 2 and 5 was p=0.04 using a one-tailed T-test. Thus, it may be concluded that Calcium Carbonate [12] provides a statistically significant increase in peak bone breaking force as compared to rats fed Calcium Carbonate [16]. The peak breaking force data of Table 5 is plotted in FIG. 8.

Results: Calcium Content of Bone

The levels of calcium in the tibia were analyzed for the rats on Diets 1, 2 and 5 after eight weeks on the prescribed diets by atomic absorption spectroscopy after dissolving the tibias in acid. The group means and standard errors of measurement for tibial calcium content are shown in Table 6.

TABLE 6

| Diet | Ca (mg)/tibia |
|---|---|
| 1 | 85 (SEM ± 2.0) |
| 2 | 91 (SEM ± 1.3) |
| 5 | 88 (SEM ± 1.8) |

The rats on Diet 2 exhibited higher levels of calcium in the tibia after eight weeks feeding than either the vitamin D deficient diet (Diet 1) or the Calcium Carbonate[16] diet (Diet 5), which was selected to correspond to the national leading brand of calcium supplement. Between Diets 1 and 2 the differences were significant at p=0.004 and between Diets 2 and 5 the differences were significant at p=0.056 using a one-tailed T-test.

In summary, rats fed Calcium Carbonate[12] (Diet 2) exhibited superior percent calcium absorption, calcium balance, bone dimension (length and width), bone weight, peak break force, and gradient (i.e., bone flexibility) than rats fed any other form of calcium carbonate after eight weeks on calcium fortified diets. Also, tibial calcium content was significantly greater in rats fed Calcium Carbonate[12] (Diet 2) than rats fed Calcium Carbonate[16] (Diet 5), chosen to correspond to the calcium carbonate of the national leading brand.

Determination of Intraperitoneal Ionized Calcium

To further investigate the improved bioavailability of the calcium carbonate according to the invention, the calcium ion concentration [$Ca^{+2}$] in the peritoneal interstitial fluid (ISF) of rats was determined using an ultrafiltrate probe. The ultrafiltrate probe is a device which can sample ISF in vivo in an awake, freely moving animal. The ultrafiltrate probe comprises semi-permeable hollow fiber membranes with a 30,000 molecular weight cut-off attached to a non-permeable tube. The fibers are implanted in the tissue to be sampled, in this case, the peritoneal cavity, and the microbore tubing is externalized. A negative pressure is applied to the tubing and the ISF flows into the tubing down the pressure gradient. Samples are collected externally at desired intervals. The ultrafiltrate probe has previously been described and employed to study tissue glucose in diabetes (Janle-Swain et al., *American Society of Artificial Internal Organs Transactions*, 33:336-340, 1987; Janle et al., *Current Separations*, 14:58-63, 1995; and Janle et al., *Journal of Herbal Pharmacotherapy*, 5:55-64, 2005), electrolytes and metabolites in simulated weightlessness (Janie et al., *Acta Astonautica*, 43:87-99, 1998), and distribution of dietary calcium (Janie et al., *Contemporary Topics in Laboratory Animal Science*, 39:46-50, 2000; and Soji et al., *Journal of Investigative Surgery*, 13:289-249, 2000), each of which is hereby incorporated by reference herein.

In this study, six female Harlan Sprague Dawley rats (200-225 g, 65-75 days old) were randomly assigned to two groups. Each groups received a nutritionally complete diet based on AIN-93G formulation and containing 0.5% calcium. For the rats in group 1, the calcium was provided by the Calcium Carbonate[12] powder and for the rats in group 2 the calcium was provided by the Calcium Carbonate[16] powder. The rats were meal trained for a week to eat food when presented to them.

Figure 27:
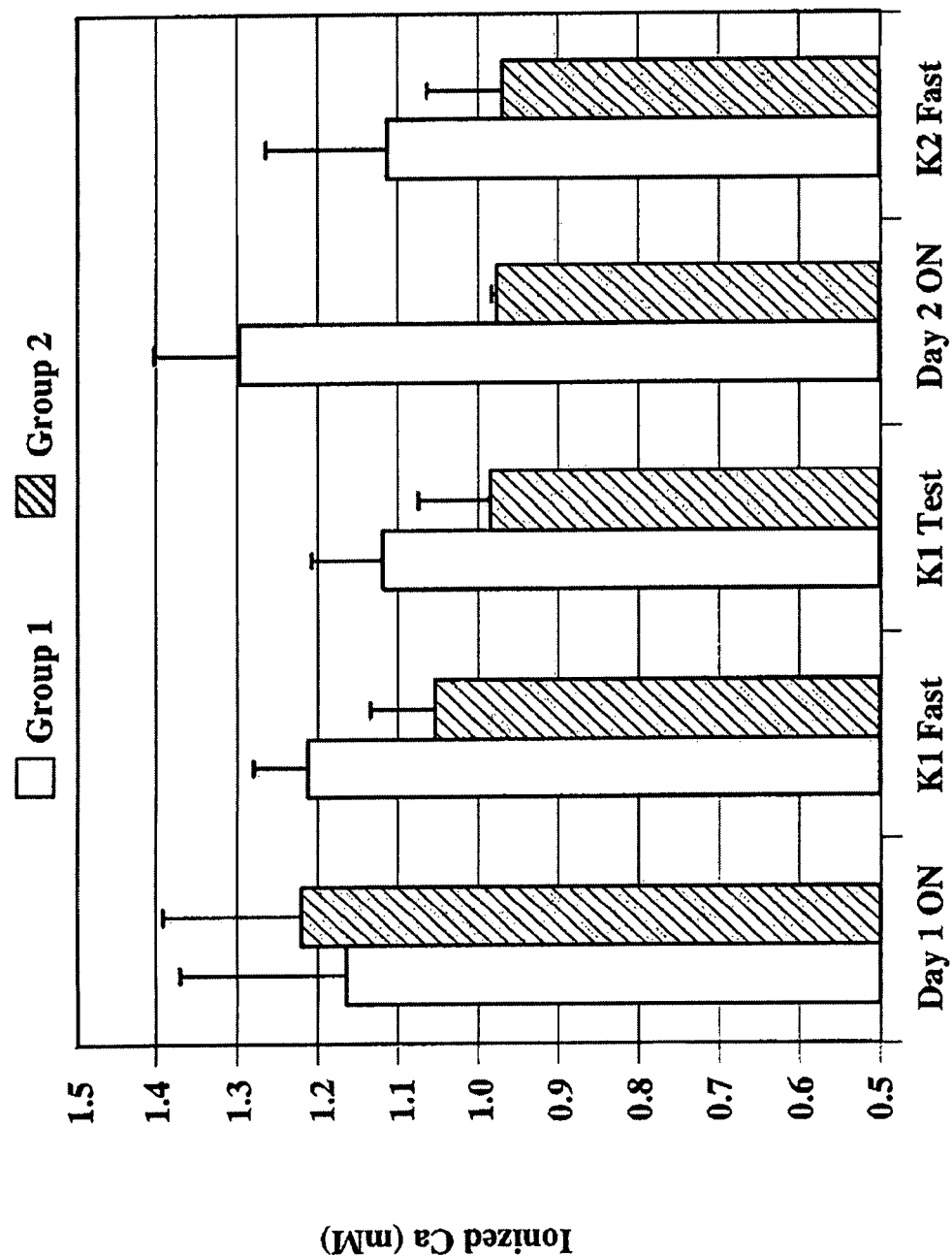
FIG. 27 compares the calcium ion concentrations in the peritoneal interstitial fluid (ISF) as measured using an ultrafiltrate probe over various time intervals for rats fed diets comprising OMYA-Cal® USP-10-AZ (Omya, Inc.) calcium carbonate powder (group 1) or OMYA-Cal® USP-15-AZ (Omya, Inc.) calcium carbonate powder (group 2).

Ultrafiltrate probes were implanted into the peritoneal cavities of the rats and ISF samples were collected at regular intervals for two days. The ultrafiltrate samples were analyzed for ionized calcium using a clinical analyzer. The results of the analysis for ionized calcium concentration in the peritoneal ISF for the group 1 rats receiving the Calcium Carbonate[12] compared to the group 2 rats receiving the Calcium Carbonate[16] diets are shown in FIG. 27. In FIG. 27, "Day 1 ON" designates the first day of the study and corresponds to a measurement cycle during which the rats had access to the food, "K1 Fast" corresponds to a period following "Day 1 ON" during which food had been removed from the rats for about four hours, and "K1 Test" corresponds to a measurement during a subsequent feeding cycle on day one of the study.

As shown in FIG. 27, during the initial measurement, "Day 1 ON," the Calcium Carbonate[16] diet (group 2) provided a slightly higher calcium ion concentration in the ISF as compared to the Calcium Carbonate[12] diet (group 1), although the differences were not statistically significant. However, during the subsequent fasting cycle "K1 Fast" the rats fed Calcium Carbonate[12] exhibited a substantially higher calcium ion concentration in the ISF as compared to the rats fed Calcium Carbonate[16]. This result was also observed during the subsequent feeding period "K1 Test."

It is believed that during the initial feeding on day one ("Day 1 ON"), both diets yielded substantially the same calcium ion concentration in the peritoneal ISF because during continuous feeding there is essentially a continuous infusion of calcium carbonate to maintain the active transport mechanism in a saturated state, as well as a continuous supply of particles of appropriate size to optimize passive transport. However, during the fasting cycle ("K1 Fast"), the Calcium Carbonate[12] powder clearly produced a higher [$Ca^{+2}$] in the ISF which is believed to have resulted from the fact that this powder provides more material in the intermediate particle size range as compared to the Calcium Carbonate[16] powder, and is thus capable of metering out a more substantial volume of particles capable of active transport and passive diffusion across the intestine over a longer time course. Surprisingly, even during the subsequent feeding cycle "K1 Test," the superiority of Calcium Carbonate[12] continues to manifest and is evidently not outweighed by the effects of continuous feeding.

The ultrafiltrate samples were collected for a second day under the same feeding conditions as day one. As shown in FIG. 27, the peritoneal calcium ion concentration was dramatically higher for rats fed the Calcium Carbonate[12] powder as compared to rats fed the Calcium Carbonate[16] powder during the first feeding cycle on day 2, designated as "Day 2 ON," and was also substantially higher during the subsequent fasting cycle "K2 Fast," similar to what was observed on day one. The next measurement on day 2, showed a very slight (~0.05 mM) difference in calcium ion levels between the two diets, with the group 2 rats exhibiting negligibly higher levels of calcium ion in the ultrafiltrate. However, this result was discarded as spurious, as it was determined that the ultrafiltrate probes had become dislodged in several rats.

Example 2

The particle size distributions of commercially available calcium carbonate powders were determined. Samples A, B, and C were each samples of Calcium Carbonate[12]. Samples D, E, and F were each samples of Calcium Carbonate[16]. Sample G was Calcium Carbonate[5] and Sample H was Calcium Carbonate[2].

The particle size distributions were obtained using a Beckman Coulter LS13 320 Particle Size Analyzer with the Aqueous Liquid Sample Module. Each calcium carbonate sample was dispersed in water and added to the Aqueous Liquid Sample Module using transfer pipettes. The particle size distributions were calculated by using an optical model for calcium carbonate with the following parameters: Diluent R.I.=1.333; Sample Real R.I.=1.596; Imaginary=0.1. The distributions were measured over the range of channel diameters from 0.04 microns to 2,000 microns.

Figure 9:
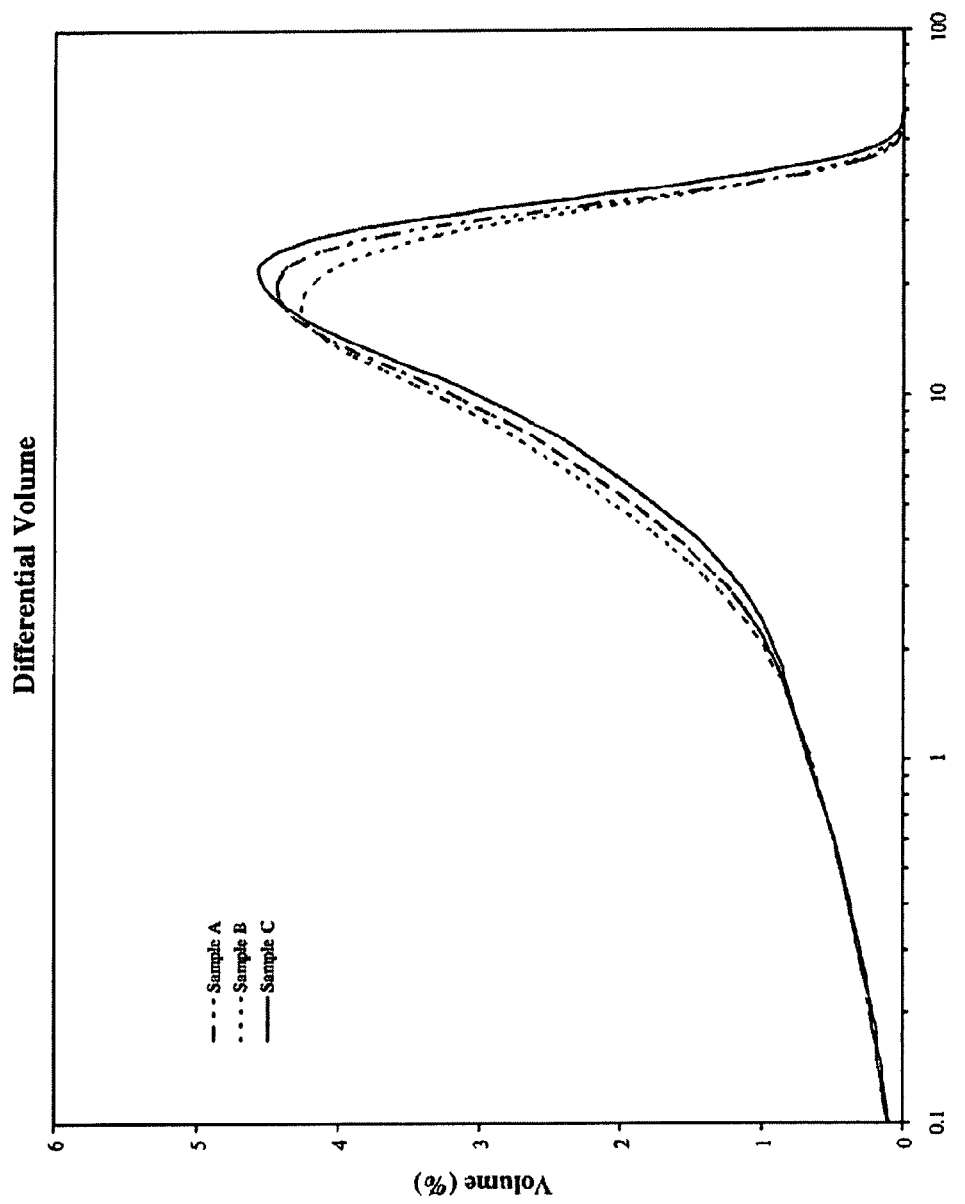
FIG. 9 shows the particle size distribution of three samples (A, B, and C) of OMYA-Cal® USP-10-AZ calcium carbonate powder as measured on a Coulter Particle Size Analyzer, expressed as cumulative volume percent between each channel diameter, plotted on a logarithmic scale.

The distributions of Samples A, B, and C (Calcium Carbonate[12]) are plotted in FIG. 9 as the differential volume percent between each channel diameter and in FIG. 10 as the cumulative volume percent of particle size less than the channel diameter. The particle size distributions of Samples A, B, and C were then averaged by taking the arithmetic mean at each channel diameter. The resulting average distribution of Samples A, B, and C, referred to herein as $\overline{X}_{(A,B,C)}$, is shown in FIG. 11 as the differential volume percent between each channel diameter and in FIG. 12 as the cumulative volume percent of particle size less than the channel diameter. FIGS. 13-16 shows $\overline{X}_{(A,B,C)}$ as cumulative volume percent less than the channel diameter across the indicated size range (bold line) along with the distribution curves corresponding to ±1 SD (standard deviation from the mean at each diameter), ±2 SD, and ±3 SD (thin lines), wherein the pair of curves corresponding to ±3 SD are the outermost, the pair of curves corresponding to ±1 SD are the inner-most to the bold $\overline{X}_{(A,B,C)}$ curve, and the pair of curves corresponding to ±2 SD are intermediate the ±1 SD and ±3 SD curves. Table 7 provides the numerical data corresponding to FIG. 13-16.

TABLE 7

CUMULATIVE VOLUME (%) OF PARTICLES OF SIZE LESS THAN CHANNEL DIAMETER

| Channel Diameter (microns) | $\overline{X}_{(A,B,C)}$ (−3SD) | $\overline{X}_{(A,B,C)}$ (−2SD) | $\overline{X}_{(A,B,C)}$ (−1SD) | $\overline{X}_{(A,B,C)}$ | $\overline{X}_{(A,B,C)}$ (+1SD) | $\overline{X}_{(A,B,C)}$ (+2SD) | $\overline{X}_{(A,B,C)}$ (+3SD) |
|---|---|---|---|---|---|---|---|
| 0.040 | 0.0000 | 0.0000 | 0.0000 | 0.0000 | 0.0000 | 0.0000 | 0.0000 |
| 0.044 | 0.0017 | 0.0017 | 0.0018 | 0.0019 | 0.0020 | 0.0021 | 0.0022 |
| 0.048 | 0.0037 | 0.0040 | 0.0042 | 0.0044 | 0.0047 | 0.0049 | 0.0051 |
| 0.053 | 0.0070 | 0.0074 | 0.0079 | 0.0083 | 0.0088 | 0.0092 | 0.0097 |
| 0.058 | 0.0135 | 0.0144 | 0.0154 | 0.0163 | 0.0173 | 0.0182 | 0.0192 |
| 0.064 | 0.0278 | 0.0292 | 0.0306 | 0.0320 | 0.0334 | 0.0348 | 0.0362 |
| 0.070 | 0.0528 | 0.0561 | 0.0594 | 0.0627 | 0.0660 | 0.0693 | 0.0726 |
| 0.077 | 0.0925 | 0.0972 | 0.1020 | 0.1067 | 0.1114 | 0.1161 | 0.1208 |
| 0.084 | 0.1450 | 0.1545 | 0.1639 | 0.1733 | 0.1828 | 0.1922 | 0.2016 |
| 0.093 | 0.2076 | 0.2217 | 0.2359 | 0.2500 | 0.2641 | 0.2783 | 0.2924 |
| 0.102 | 0.2923 | 0.3093 | 0.3263 | 0.3433 | 0.3603 | 0.3773 | 0.3943 |
| 0.112 | 0.3852 | 0.4068 | 0.4284 | 0.4500 | 0.4716 | 0.4932 | 0.5148 |
| 0.122 | 0.4979 | 0.5242 | 0.5504 | 0.5767 | 0.6029 | 0.6292 | 0.6554 |
| 0.134 | 0.6177 | 0.6507 | 0.6837 | 0.7167 | 0.7497 | 0.7827 | 0.8157 |
| 0.148 | 0.7558 | 0.7961 | 0.8364 | 0.8767 | 0.9169 | 0.9572 | 0.9975 |
| 0.162 | 0.9084 | 0.9534 | 0.9984 | 1.0433 | 1.0883 | 1.1333 | 1.1782 |
| 0.178 | 1.076 | 1.128 | 1.181 | 1.233 | 1.286 | 1.338 | 1.391 |
| 0.195 | 1.251 | 1.313 | 1.375 | 1.437 | 1.498 | 1.560 | 1.622 |
| 0.214 | 1.451 | 1.520 | 1.588 | 1.657 | 1.725 | 1.794 | 1.862 |
| 0.235 | 1.669 | 1.745 | 1.821 | 1.897 | 1.973 | 2.048 | 2.124 |
| 0.258 | 1.912 | 1.992 | 2.073 | 2.153 | 2.234 | 2.314 | 2.395 |
| 0.284 | 2.167 | 2.257 | 2.347 | 2.437 | 2.527 | 2.617 | 2.706 |
| 0.311 | 2.449 | 2.544 | 2.639 | 2.733 | 2.828 | 2.923 | 3.017 |
| 0.342 | 2.762 | 2.861 | 2.961 | 3.060 | 3.159 | 3.259 | 3.358 |
| 0.375 | 3.077 | 3.186 | 3.295 | 3.403 | 3.512 | 3.621 | 3.730 |
| 0.412 | 3.434 | 3.545 | 3.656 | 3.767 | 3.878 | 3.988 | 4.099 |
| 0.452 | 3.802 | 3.920 | 4.039 | 4.157 | 4.275 | 4.393 | 4.511 |
| 0.496 | 4.212 | 4.330 | 4.449 | 4.567 | 4.685 | 4.803 | 4.921 |
| 0.545 | 4.649 | 4.769 | 4.890 | 5.010 | 5.130 | 5.251 | 5.371 |
| 0.598 | 5.109 | 5.229 | 5.350 | 5.470 | 5.590 | 5.711 | 5.831 |
| 0.656 | 5.596 | 5.718 | 5.841 | 5.963 | 6.086 | 6.208 | 6.331 |
| 0.721 | 6.116 | 6.238 | 6.361 | 6.483 | 6.606 | 6.728 | 6.851 |
| 0.791 | 6.687 | 6.802 | 6.918 | 7.033 | 7.149 | 7.264 | 7.380 |
| 0.868 | 7.262 | 7.380 | 7.499 | 7.617 | 7.735 | 7.853 | 7.971 |

TABLE 7-continued

CUMULATIVE VOLUME (%) OF PARTICLES OF SIZE
LESS THAN CHANNEL DIAMETER

| Channel Diameter (microns) | $\overline{X}_{(A,B,C)}$ (−3SD) | $\overline{X}_{(A,B,C)}$ (−2SD) | $\overline{X}_{(A,B,C)}$ (−1SD) | $\overline{X}_{(A,B,C)}$ | $\overline{X}_{(A,B,C)}$ (+1SD) | $\overline{X}_{(A,B,C)}$ (+2SD) | $\overline{X}_{(A,B,C)}$ (+3SD) |
|---|---|---|---|---|---|---|---|
| 0.953 | 7.907 | 8.016 | 8.125 | 8.233 | 8.342 | 8.451 | 8.560 |
| 1.047 | 8.560 | 8.666 | 8.773 | 8.880 | 8.987 | 9.094 | 9.200 |
| 1.149 | 9.259 | 9.359 | 9.460 | 9.560 | 9.660 | 9.761 | 9.861 |
| 1.261 | 9.893 | 10.02 | 10.14 | 10.27 | 10.39 | 10.52 | 10.64 |
| 1.384 | 10.75 | 10.84 | 10.94 | 11.03 | 11.13 | 11.22 | 11.32 |
| 1.520 | 11.55 | 11.64 | 11.74 | 11.83 | 11.93 | 12.02 | 12.12 |
| 1.668 | 12.35 | 12.44 | 12.54 | 12.63 | 12.73 | 12.82 | 12.92 |
| 1.832 | 13.08 | 13.22 | 13.36 | 13.50 | 13.64 | 13.78 | 13.92 |
| 2.011 | 13.98 | 14.12 | 14.26 | 14.40 | 14.54 | 14.68 | 14.82 |
| 2.207 | 14.82 | 14.99 | 15.16 | 15.33 | 15.50 | 15.67 | 15.84 |
| 2.423 | 15.65 | 15.87 | 16.08 | 16.30 | 16.52 | 16.73 | 16.95 |
| 2.660 | 16.58 | 16.84 | 17.10 | 17.37 | 17.63 | 17.89 | 18.15 |
| 2.920 | 17.61 | 17.92 | 18.22 | 18.53 | 18.84 | 19.15 | 19.46 |
| 3.205 | 18.58 | 18.96 | 19.35 | 19.73 | 20.12 | 20.51 | 20.89 |
| 3.519 | 19.57 | 20.07 | 20.57 | 21.07 | 21.57 | 22.06 | 22.56 |
| 3.863 | 20.73 | 21.31 | 21.89 | 22.47 | 23.05 | 23.63 | 24.20 |
| 4.240 | 22.00 | 22.66 | 23.33 | 24.00 | 24.67 | 25.34 | 26.00 |
| 4.655 | 23.44 | 24.18 | 24.93 | 25.67 | 26.41 | 27.15 | 27.89 |
| 5.110 | 24.84 | 25.70 | 26.57 | 27.43 | 28.30 | 29.16 | 30.03 |
| 5.610 | 26.43 | 27.42 | 28.41 | 29.40 | 30.39 | 31.38 | 32.37 |
| 6.158 | 28.12 | 29.24 | 30.35 | 31.47 | 32.58 | 33.70 | 34.81 |
| 6.760 | 30.00 | 31.23 | 32.47 | 33.70 | 34.93 | 36.17 | 37.40 |
| 7.421 | 31.99 | 33.35 | 34.71 | 36.07 | 37.42 | 38.78 | 40.14 |
| 8.147 | 34.17 | 35.65 | 37.12 | 38.60 | 40.08 | 41.55 | 43.03 |
| 8.943 | 36.40 | 38.05 | 39.69 | 41.33 | 42.98 | 44.62 | 46.26 |
| 9.818 | 39.06 | 40.78 | 42.51 | 44.23 | 45.96 | 47.68 | 49.41 |
| 10.78 | 41.67 | 43.56 | 45.45 | 47.33 | 49.22 | 51.11 | 53.00 |
| 11.83 | 44.75 | 46.72 | 48.69 | 50.67 | 52.64 | 54.61 | 56.59 |
| 12.99 | 48.10 | 50.16 | 52.21 | 54.27 | 56.32 | 58.38 | 60.43 |
| 14.26 | 51.66 | 53.79 | 55.93 | 58.07 | 60.20 | 62.34 | 64.47 |
| 15.65 | 55.43 | 57.65 | 59.88 | 62.10 | 64.32 | 66.55 | 68.77 |
| 17.18 | 59.63 | 61.85 | 64.08 | 66.30 | 68.52 | 70.75 | 72.97 |
| 18.86 | 63.95 | 66.18 | 68.40 | 70.63 | 72.86 | 75.09 | 77.32 |
| 20.71 | 68.59 | 70.74 | 72.88 | 75.03 | 77.18 | 79.33 | 81.48 |
| 22.73 | 73.55 | 75.50 | 77.45 | 79.40 | 81.35 | 83.30 | 85.25 |
| 24.95 | 78.40 | 80.17 | 81.93 | 83.70 | 85.47 | 87.23 | 89.00 |
| 27.39 | 83.45 | 84.90 | 86.35 | 87.80 | 89.25 | 90.70 | 92.15 |
| 30.07 | 87.90 | 89.09 | 90.28 | 91.47 | 92.66 | 93.85 | 95.04 |
| 33.01 | 91.87 | 92.77 | 93.67 | 94.57 | 95.47 | 96.37 | 97.26 |
| 36.24 | 95.16 | 95.75 | 96.34 | 96.93 | 97.52 | 98.11 | 98.71 |
| 39.78 | 97.43 | 97.79 | 98.14 | 98.50 | 98.86 | 99.21 | 99.57 |
| 43.67 | 98.92 | 99.09 | 99.26 | 99.43 | 99.60 | 99.77 | 99.94 |
| 47.94 | 99.73 | 99.77 | 99.82 | 99.87 | 99.91 | 99.96 | 100.0 |
| 52.62 | 99.92 | 99.94 | 99.96 | 99.97 | 99.99 | 100.0 | 100.0 |
| 57.77 | 99.99 | 99.99 | 100.0 | 100.0 | 100.0 | 100.0 | 100.0 |
| 63.41 | 100.0 | 100.0 | 100.0 | 100.0 | 100.0 | 100.0 | 100.0 |

As used herein, the phrase "similar to," when used in reference to the particle size distribution of $\overline{X}_{(A,B,C)}$ expressed as cumulative volume percent of particles of size less than the channel diameter (as shown in FIGS. 13-16), means within ±3SD of the corresponding cumulative volume percent for $\overline{X}_{(A,B,C)}$ at each channel diameter. Similarly, the term "approximately the same as," when used in reference to the particle size distribution of $\overline{X}_{(A,B,C)}$ expressed as cumulative volume percent of particles of size less than the channel diameter (as shown in FIGS. 13-16), means within ±2SD of the corresponding cumulative volume percent for $\overline{X}_{(A,B,C)}$ at each channel diameter. The term "substantially identical to," when used in reference to the particle size distribution of $\overline{X}_{(A,B,C)}$ expressed as cumulative volume percent of particles of size less than the channel diameter (as shown in FIGS. 13-16), means within ±1 SD of the corresponding cumulative volume percent for $\overline{X}_{(A,B,C)}$ at each channel diameter. The data in Table 7 is provided to assist the skilled artisan in determining if a distribution is "similar to," "approximately the same as," or "substantially identical to" the particle size distribution of $\overline{X}_{(A,B,C)}$.

Figure 17:
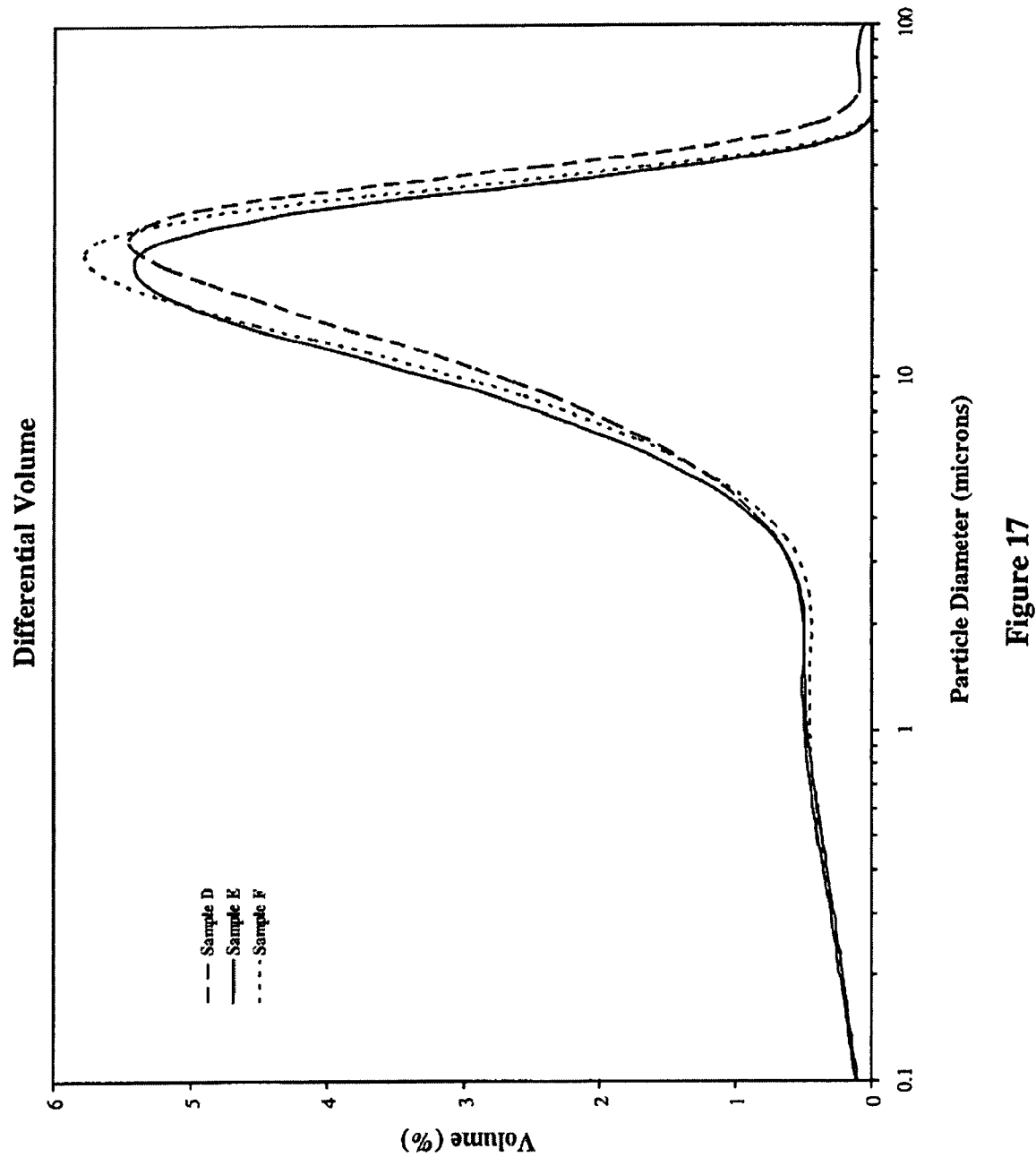
FIG. 17 shows the particle size distribution of three samples (D, E, and F) of OMYA-Cal® USP-15-AZ calcium carbonate powder as measured on a Coulter Particle Size Analyzer, expressed as cumulative volume percent between each channel diameter, plotted on a logarithmic scale from 0.1 to 100 microns.
Figure 18:
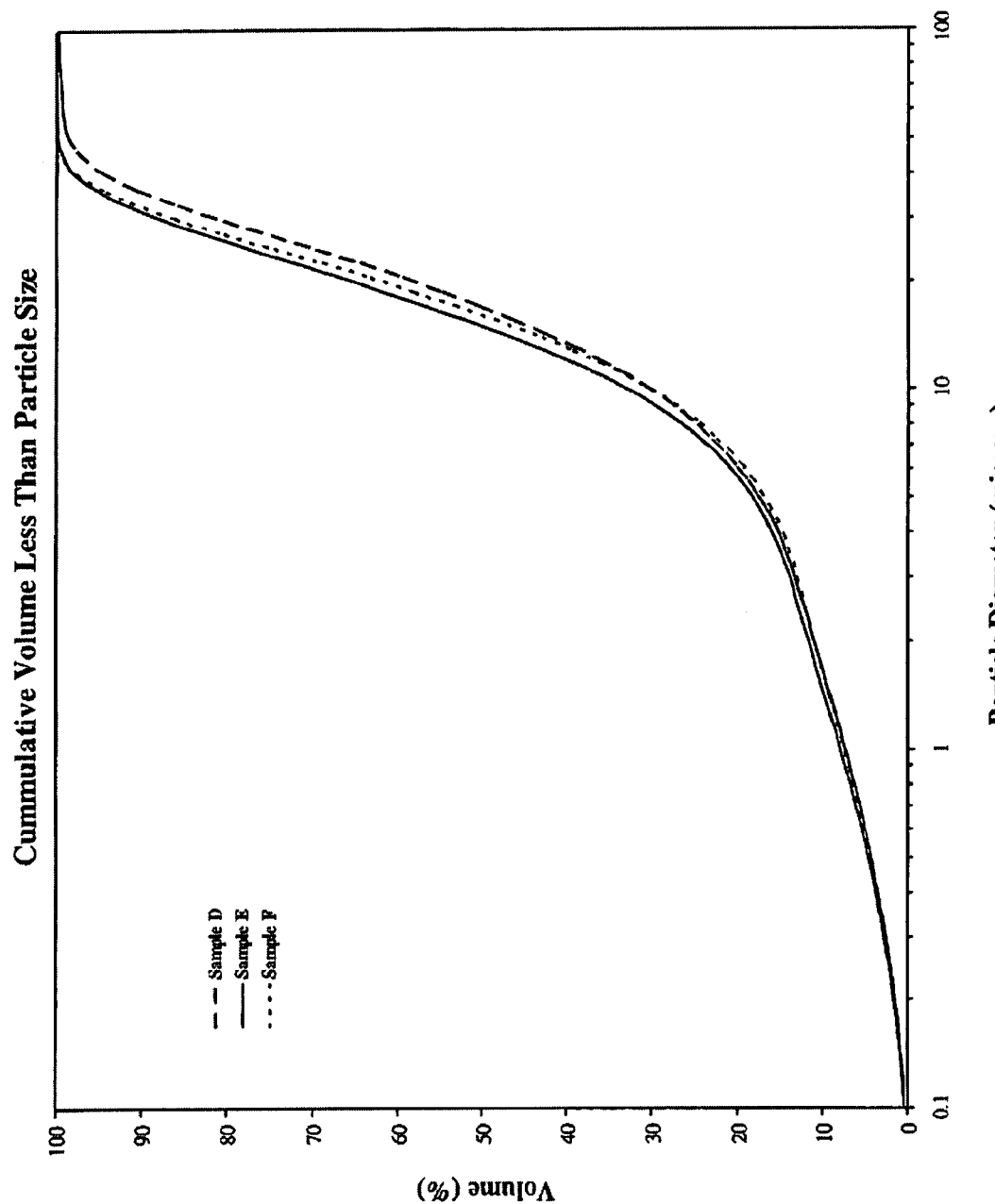
FIG. 18 shows the particle size distribution of three samples (A, B, and C) of OMYA-Cal® USP-10-AZ calcium carbonate powder as measured on a Coulter Particle Size Analyzer, expressed as cumulative volume percent of particle size less than the channel diameter, plotted on a logarithmic scale from 0.1 to 100 microns.
Figure 19:
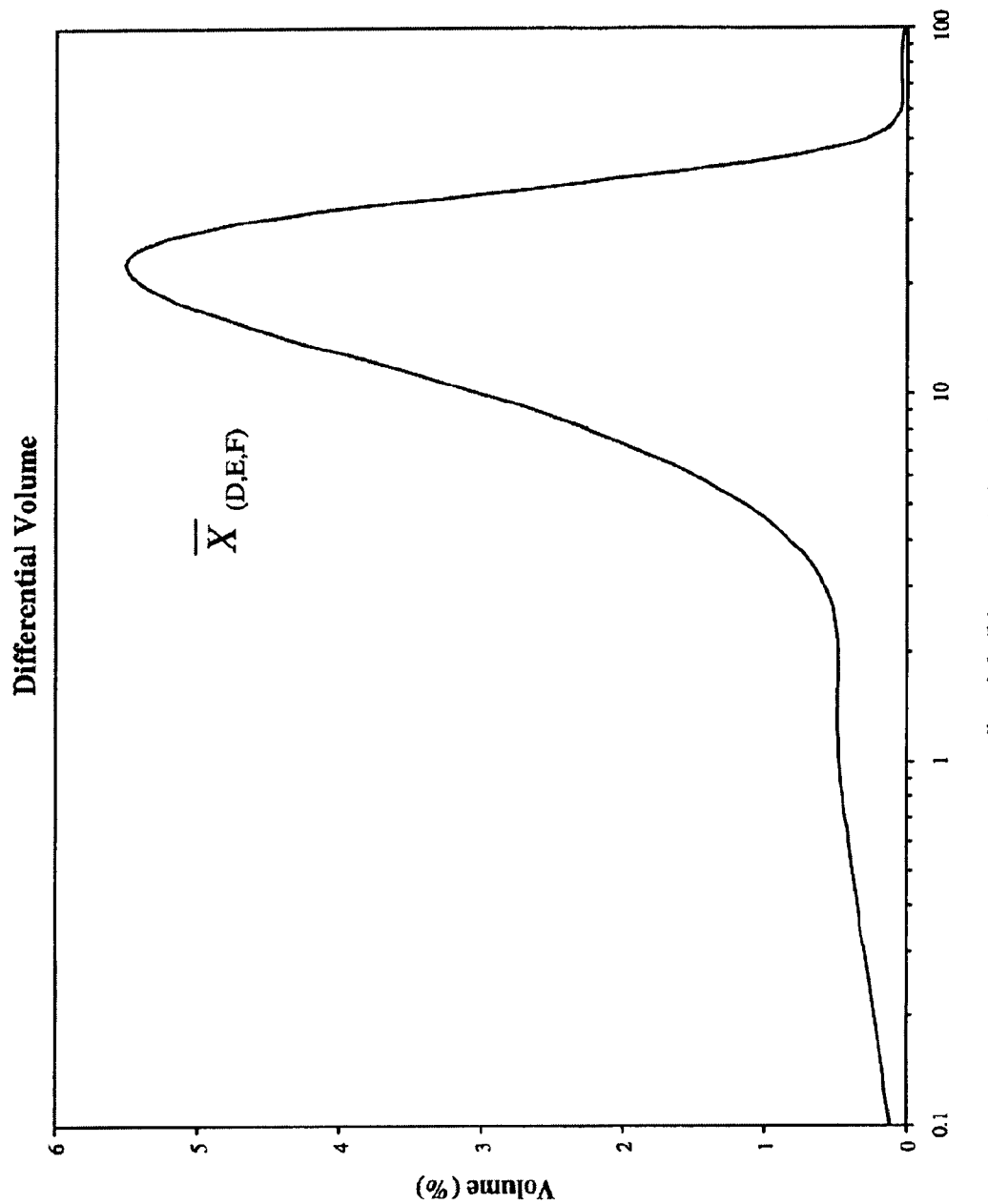
FIG. 19 shows the particle size distribution corresponding to the mean at each channel diameter, designated $\overline{X}_{(D,E,F)}$, of three samples (D, E, and F) of OMYA-Cal® USP-15-AZ calcium carbonate powder as measured on a Coulter Particle Size Analyzer, expressed as cumulative volume percent between each channel diameter, plotted on a logarithmic scale from 0.1 to 100 microns.
Figure 20:
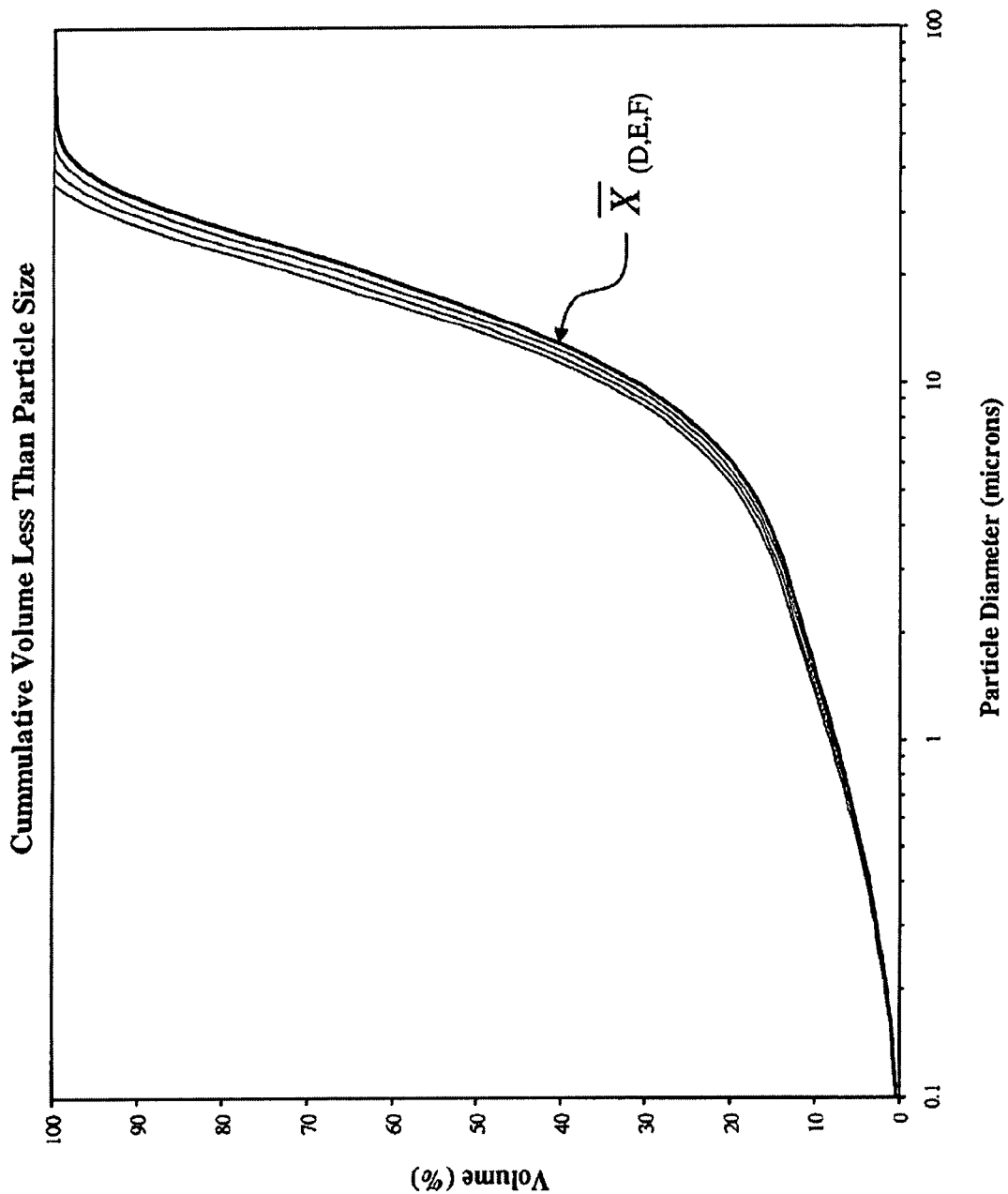
FIG. 20 shows the particle size distribution corresponding to the mean at each channel diameter, designated $\overline{X}_{(D,E,F)}$, of three samples (D, E, and F) of OMYA-Cal® USP-15-AZ calcium carbonate powder as measured on a Coulter Particle Size Analyzer, expressed as cumulative volume percent of particles smaller than the channel diameter, plotted on a logarithmic scale from 0.1 to 100 microns. The distribution corresponding to $\overline{X}_{(D,E,F)}$ is shown as the bold line. Distributions corresponding to +1 SD (standard deviation), +2 SD, and +3 SD of the mean at each channel diameter are provided (thin lines).
Figure 21:
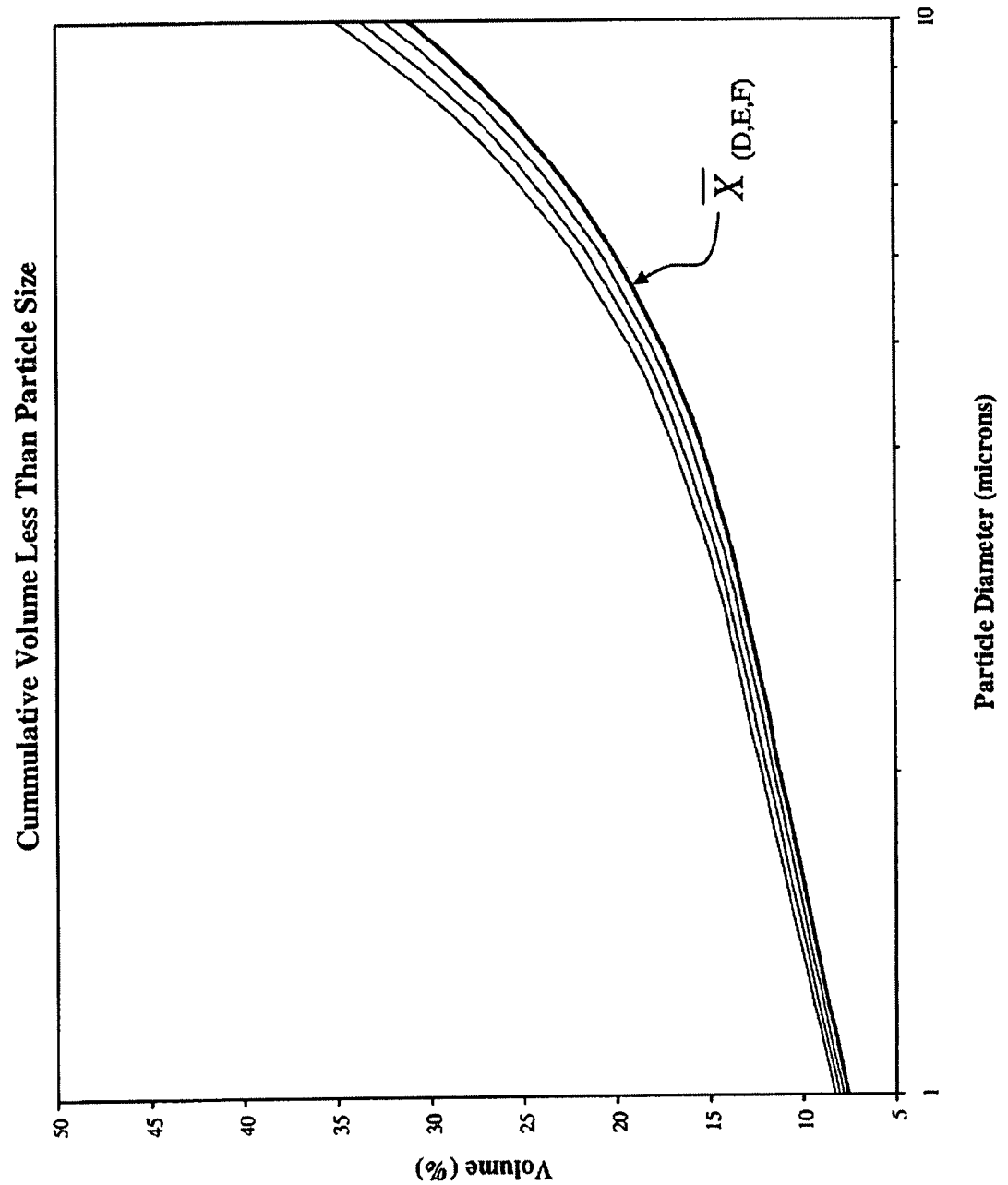
FIG. 21 is an enlargement of FIG. 20 in the intermediate particle size rang of 1 to 10 microns.

The distributions of Samples D, E, and F (Calcium Carbonate[16]) are plotted in FIG. 17 as the differential volume percent between each channel diameter and in FIG. 18 as the cumulative volume percent of particle size less than the channel diameter. The particle size distributions of Samples D, E, and F were likewise averaged by taking the arithmetic mean at each channel diameter. The resulting average distribution $\overline{X}_{(D,E,F)}$ is shown in FIG. 19 as the differential volume percent between each channel diameter and in FIG. 20 as the cumulative volume percent of particle size less than the channel diameter (bold line), along with the distribution curves corresponding to +1 SD (standard deviation from the mean at each diameter), +2 SD, and +3 SD (thin lines). FIG. 21 is an expansion of FIG. 20 to show the intermediate particle size region, in this case, from 1 to 10 microns.

Figure 22:
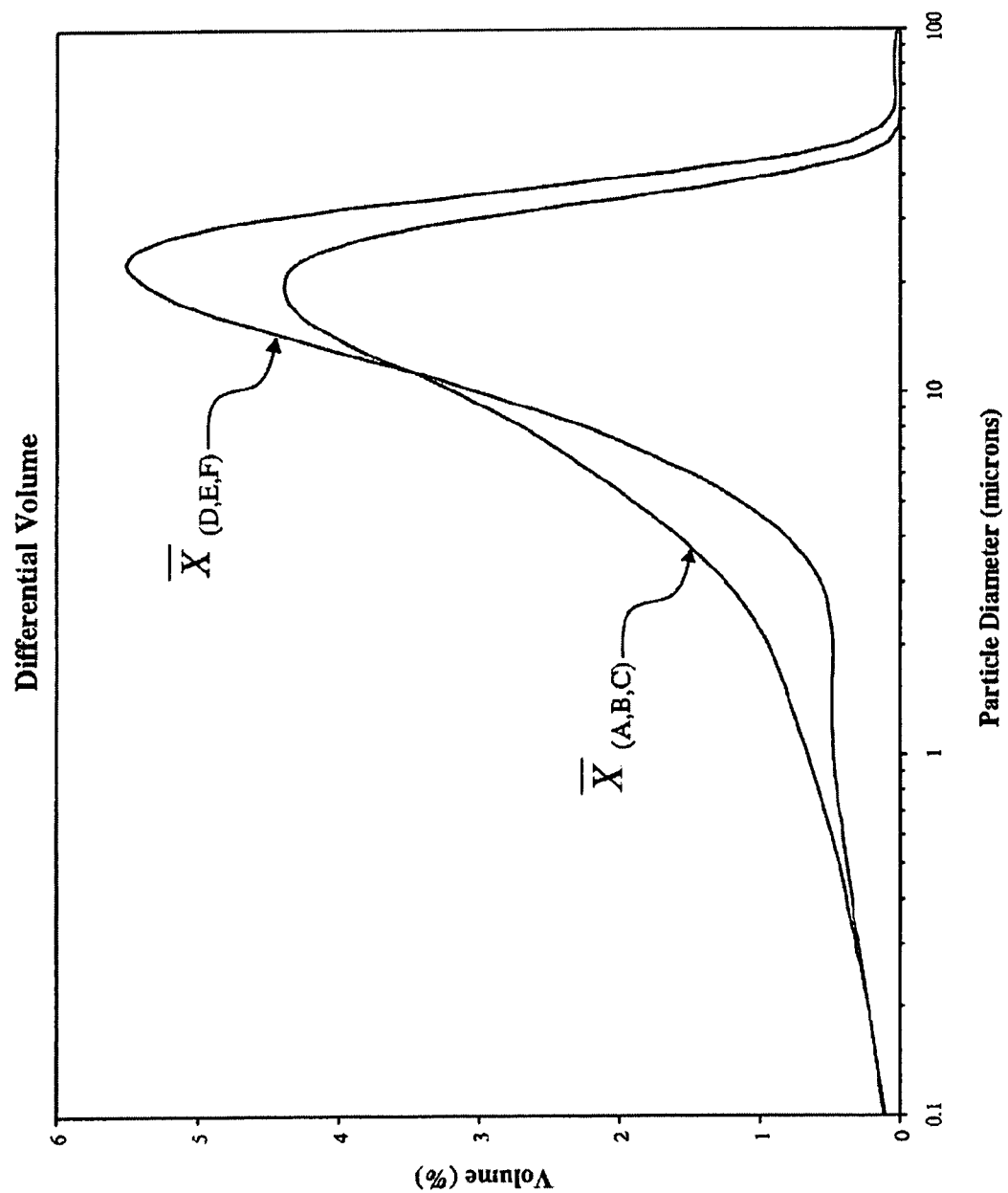
FIG. 22 shows the particle size distributions corresponding to $\overline{X}_{(A,B,C)}$ and $\overline{X}_{(D,E,F)}$ expressed as cumulative volume percent between each channel diameter, plotted on a logarithmic scale from 0.1 to 100 microns.
Figure 23:
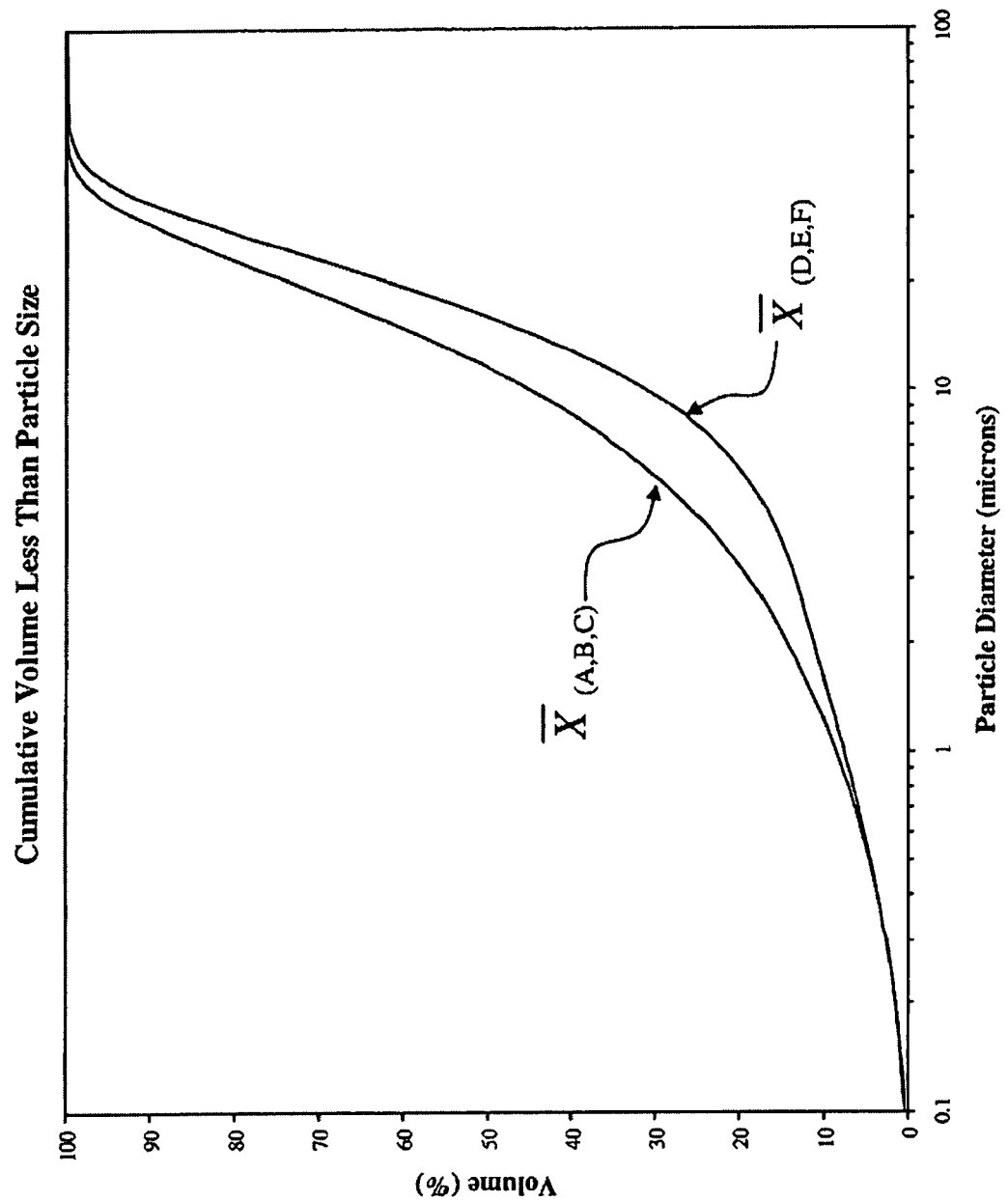
FIG. 23 shows the particle size distributions corresponding to $\overline{X}_{(A,B,C)}$ and $\overline{X}_{(D,E,F)}$ expressed as cumulative volume percent of particles of size less than the channel diameter, plotted on a logarithmic scale from 0.1 to 100 microns.
Figure 24:
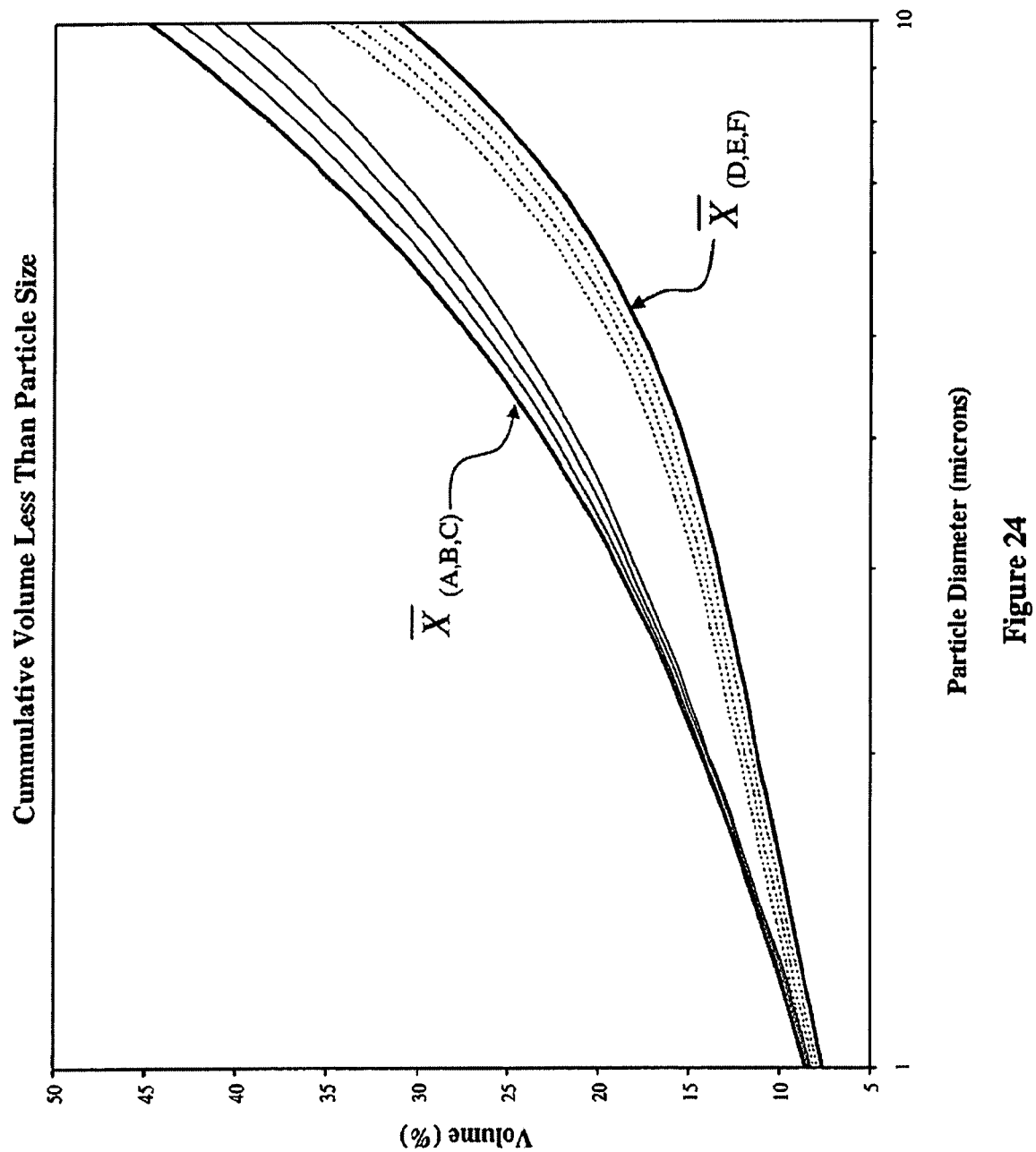
FIG. 24 shows the particle size distributions in the intermediate size range corresponding to $\overline{X}_{(A,B,C)}$ and $\overline{X}_{(D,E,F)}$ expressed as cumulative volume percent of particles of size less than the channel diameter, plotted on a logarithmic scale from 1 to 10 microns. For $\overline{X}_{(A,B,C)}$, distribution curve corresponding to −1 SD, −2 SD, and −3 SD are provided. For $\overline{X}_{(D,E,F)}$, distribution curve corresponding to +1 SD, +2 SD, and +3 SD are provided.

FIGS. 22 and 23 compare the distributions of $\overline{X}_{(A,B,C)}$ and $\overline{X}_{(D,E,F)}$ as differential volume percent between each channel diameter across and as the cumulative volume percent of particle size less than the channel diameter, respectively. FIG. 24 compares the distributions of $\overline{X}_{(A,B,C)}$ (including −1

SD, −2 SD, and −3 SD) with the $\overline{X}_{(D,E,F)}$ (including +1 SD, +2 SD, and +3 SD) distribution as differential volume percent between each channel diameter across the range of 1 to 10 microns. It can be seen that substantial difference between these powders are evident even at ±3 SD, as the Table 8 provides the descriptive statistics for the particle size distributions for calcium carbonate powders according to the invention, i.e., samples A, B, C, and $\overline{X}_{(A,B,C)}$, in comparison with calcium carbonate powders of lesser bioavailability, i.e., samples D, E, F, G, H and $\overline{X}_{(D,E,F)}$.

TABLE 8

|  | A | B | C | $\overline{X}_{(A,B,C)}$ | D | E | F | $\overline{X}_{(D,E,F)}$ | G | H |
|---|---|---|---|---|---|---|---|---|---|---|
| mean (μm) | 13.39 | 12.99 | 14.31 | 13.56 | 18.55 | 16.15 | 17.04 | 17.25 | 5.08 | 14.78 |
| median (μm) | 11.52 | 10.94 | 12.46 | 11.64 | 17.04 | 15.11 | 16.24 | 16.13 | 4.59 | 1.99 |
| D[3,2] (μm) | 2.41 | 2.39 | 2.53 | 2.44 | 2.86 | 2.66 | 2.77 | 2.76 | — | 0.88 |
| mean/median | 1.62 | 1.187 | 1.15 | 1.32 | 1.089 | 1.069 | 1.05 | 1.069 | 1.105 | 7.4 |
| mode (μm) | 21.69 | 18.00 | 23.81 | 21.17 | 26.14 | 21.69 | 23.81 | 23.88 | 6.45 | 1.32 |
| SSA (cm²/g) | 9180 | 9268 | 8753 | 9067 | 7748 | 8330 | 7982 | 8020 | — | 25037 |
| SD (μm) | 10.41 | 10.3 | 11.05 | 10.59 | 13.56 | 10.97 | 11.18 | 11.90 | 3.603 | 34.04 |
| variance (μm²) | 108.3 | 106.2 | 122.1 | 112.2 | 183.8 | 120.3 | 125 | 143.0 | 12.98 | 1158 |
| CV (%) | 77.7 | 79.3 | 77.2 | 78.1 | 73.1 | 67.9 | 65.6 | 68.9 | 70.9 | 230 |
| skewedness | 0.70 | 0.80 | 0.67 | 0.72 | 1.12 | 0.48 | 0.39 | 0.66 | 0.68 | 3.30 |
| kurtosis | −0.25 | 0.01 | −0.28 | −0.17 | 3.34 | −0.38 | −0.48 | 0.83 | −0.04 | 10.66 |
| $D_{10}$ (μm) | 1.203 | 1.21 | 1.24 | 1.22 | 1.66 | 1.47 | 1.64 | 1.59 | 0.62 | 0.33 |
| $D_{50}$ (μm) | 11.52 | 10.94 | 12.46 | 11.64 | 17.04 | 15.11 | 16.24 | 16.13 | 4.59 | 1.99 |
| $D_{90}$ (μm) | 28.55 | 28.01 | 30.20 | 28.92 | 35.88 | 31.51 | 32.48 | 33.29 | 10.19 | 41.86 | curve corresponding to $\overline{X}_{(A,B,C)}$−3 SD is substantially above that of $\overline{X}_{(A,B,C)}$+3 SD across substantially all of the intermediate size range from 1 to 10 microns.

Figure 25:
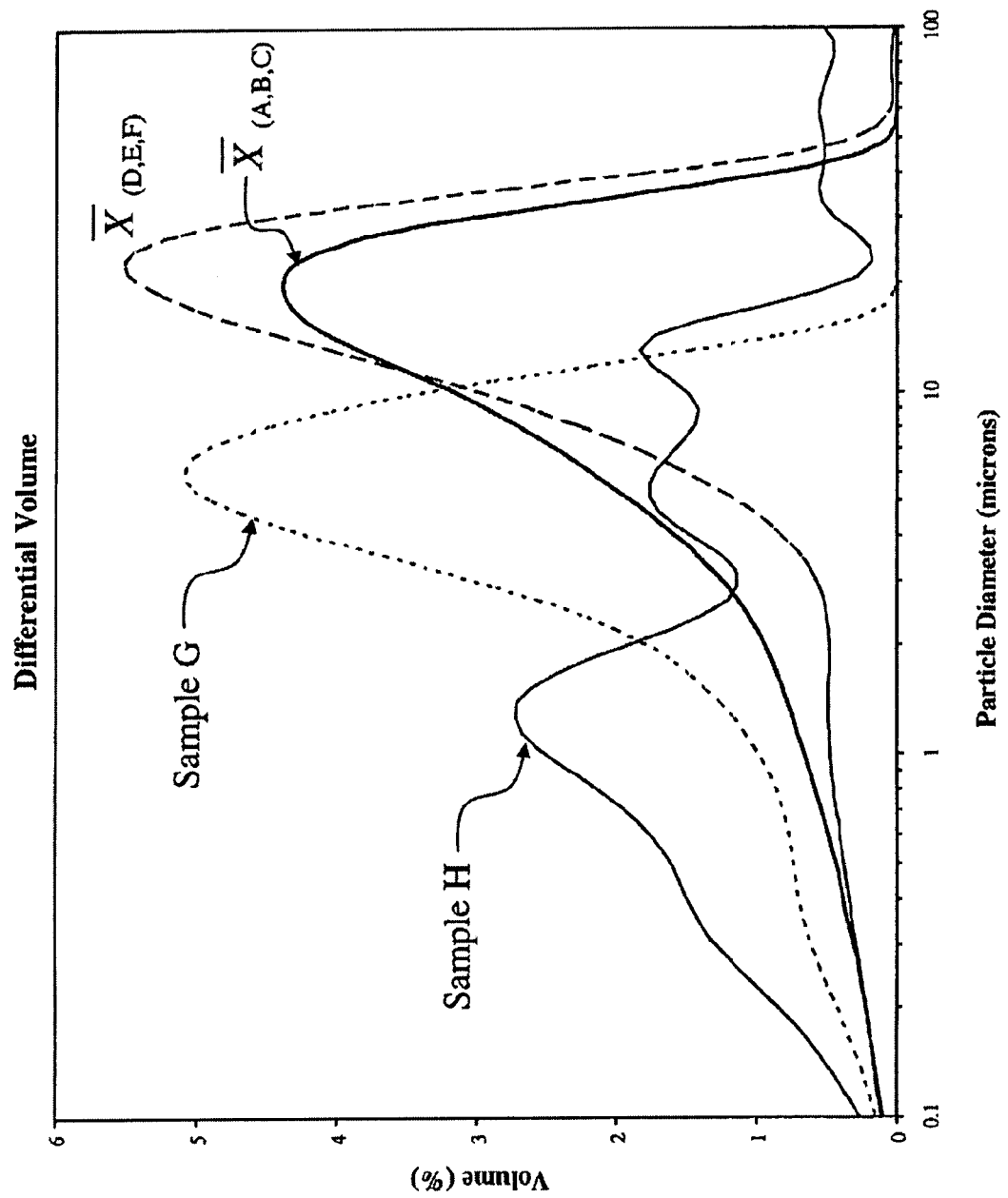
FIG. 25 shows the particles size distributions plotted on a logarithmic scale from 0.1 to 100 microns, expressed as volume percent between each channel diameter, for $\overline{X}_{(A,B,C)}$, $\overline{X}_{(D,E,F)}$, Sample G, and Sample H, corresponding to calcium carbonate powders having median particle sizes of 11.64, 16.13, 4.59, and 1.99 microns, respectively.
Figure 26:
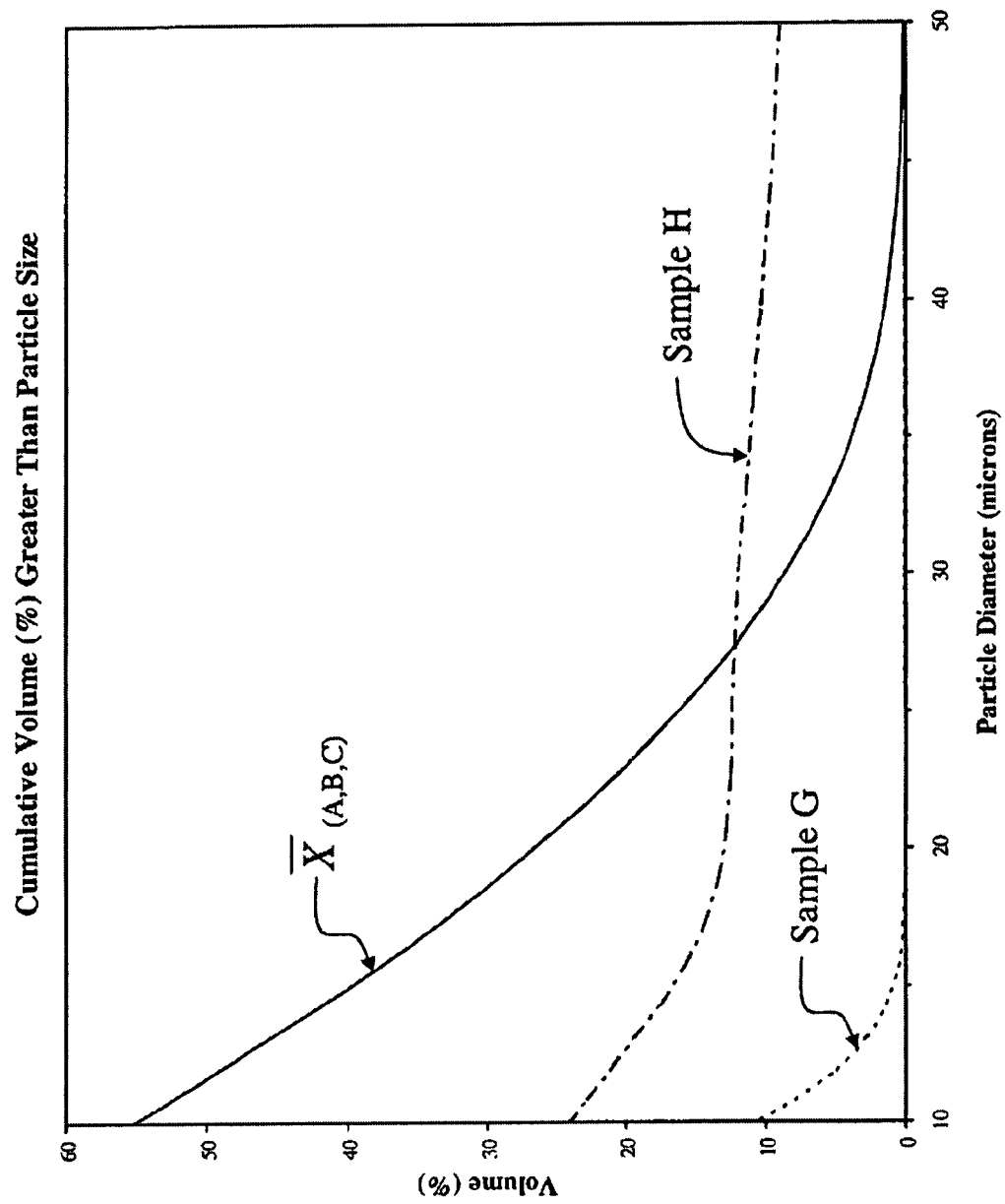
FIG. 26 shows particles size distributions in the large particle size range, expressed as cumulative volume of particles of size greater than the channel diameter for channel diameters between 10 micron and 100 microns on a logarithmic scale, for $\overline{X}_{(A,B,C)}$, Sample G, and Sample H.

FIG. 25 shows the distributions of $\overline{X}_{(A,B,C)}$, $\overline{X}_{(D,E,F)}$, Sample G, and Sample H expressed as cumulative volume percent of particle size between the channel diameters. Inspection of FIG. 25 reveals that $\overline{X}_{(A,B,C)}$ is the only powder which provides substantial volume under the curve at both the intermediate and large particle size ranges. While the distribution of Sample H is robust in the small particle range, it is deficient in both intermediate and large particles. Sample G provides the substantial portion of its volume in the intermediate size range, but likewise has very little area under the curve in the large particle region. The deficiency of these powders in the rat studies of Example 1, relative to Calcium Carbonate[12], can be explained on this basis. Similarly, $\overline{X}_{(D,E,F)}$ is also inferior to $\overline{X}_{(A,B,C)}$ in the intermediate particle size region, though it does provide more volume in the large particle size region. The results detailed in Example 1 therefore compel the conclusion that optimal in vivo utilization of calcium requires more volume in the intermediate particle size range than is provided by $\overline{X}_{(D,E,F)}$.

The distributions may be defined by various well known descriptive statistical parameters including mean (arithmetic mean by volume), median (i.e., the particle size at which half the volume is above and half the volume is below), mode (most common particle size by volume), mean to median ratio (mean/median), standard deviation (SD), variance, coefficient of variance (CV), skewedness, and kurtosis (leptokurtic or platykurtic). The distributions can also be characterized by the $D_{10}$, $D_{50}$, and $D_{90}$ values which represent the particle diameters at which 10%, 50% and 90% of the sample volume, respectively, is less than that diameter. The surface area of the various powders may be defined in terms of specific surface area (SSA) or the surface area mean moment D[3,2]. The specific surface area is defined as the ratio of the surface area to mass and provided in units of cm²/g. The surface area mean moment D[3,2] is the diameter of a particle having the same volume/surface area ratio as the entire distribution and defined by the equation:

$$D[3,2] = \frac{\sum_i d_i^3}{\sum_i d_i^2}$$

The calcium carbonate powders according to the invention, represented in Table 8 as samples A, B, C, and $\overline{X}_{(A,B,C)}$, may be described in term of any one of the parameters of Table 8, or any combinations thereof. In some embodiments, the calcium carbonate powders according to the invention are described in terms of their $D_{10}$, $D_{50}$, and $D_{90}$ values. Table 9 shows the $D_{10}$, $D_{50}$, and $D_{90}$ values for $\overline{X}_{(A,B,C)}$ as well as the values corresponding to ±1 SD, ±2 SD, and ±3 SD of the mean, each of which is considered to be an embodiment of the invention.

TABLE 9

|  | $D_{10}$ | $D_{50}$ | $D_{90}$ |
|---|---|---|---|
| $\overline{X}_{(A,B,C)}$ + 3SD | 1.27 | 13.5 | 31.7 |
| $\overline{X}_{(A,B,C)}$ + 2SD | 1.25 | 12.9 | 30.8 |
| $\overline{X}_{(A,B,C)}$ + 1SD | 1.24 | 12.3 | 29.9 |
| $\overline{X}_{(A,B,C)}$ | 1.22 | 11.6 | 28.9 |
| $\overline{X}_{(A,B,C)}$ − 1SD | 1.20 | 11.0 | 28.0 |
| $\overline{X}_{(A,B,C)}$ − 2SD | 1.19 | 10.4 | 27.1 |
| $\overline{X}_{(A,B,C)}$ − 3SD | 1.17 | 9.8 | 26.1 |

Accordingly, the invention embraces embodiments having a $D_{10}$ value ranging from about 1.17 to about 1.27 microns, about 1.19 to about 1.25 micron, about 1.20 to about 1.24 microns, or about 1.22 microns. Similarly, various embodiments will have a $D_{50}$ value ranging from about 9.8 to about 13.5 microns, about 10.4 to about 12.9 microns, about 11 to about 12.3 microns, and about 11.6 microns. The $D_{90}$ value in various embodiments will range from about 26.1 to about 31.7 microns, about 27.1 to about 30.8 microns, about 28.0 to about 29.9 microns. Any combinations of these ranges and sub-ranges are also considered to be within the scope of the invention but are omitted herein for brevity. In one embodiment, the D90 value will be about 28.9 microns.

As discussed above, the exceptional bioavailability of the calcium forms of the invention is believed to result, in part, from the volume of particles in the intermediate size range. The particle size data across an exemplary intermediate particle size range for $\overline{X}_{(A,B,C)}$ and $\overline{X}_{(D,E,F)}$ (including ±1 SD, ±2SD, and ±3 SD of the mean at each particle size) is provided in Table 10 along with the corresponding data for Samples G and H.

of $\overline{X}_{(A,B,C)}$ (−3 SD), $\overline{X}_{(A,B,C)}$ (−2 SD), $\overline{X}_{(A,B,C)}$ (−1 SD), $\overline{X}_{(D,E,F)}$, $\overline{X}_{(D,E,F)}$ (+1 SD), $\overline{X}_{(D,E,F)}$ (+2 SD), or $\overline{X}_{(D,E,F)}$ (+3 SD) where the upper end of the volume percent range for particles of intermediate size is not critical and is only

TABLE 10

| Channel Diameter (microns) | $\overline{X}_{(A,B,C)}$ | $\overline{X}_{(A,B,C)}$ (−1SD) | $\overline{X}_{(A,B,C)}$ (−2SD) | $\overline{X}_{(A,B,C)}$ (−3SD) | $\overline{X}_{(D,E,F)}$ | $\overline{X}_{(D,E,F)}$ (+1SD) | $\overline{X}_{(D,E,F)}$ (+2SD) | $\overline{X}_{(D,E,F)}$ (+3SD) | Sample G | Sample H |
|---|---|---|---|---|---|---|---|---|---|---|
| 1.05 | 8.9 | 8.8 | 8.7 | 8.6 | 7.8 | 8.1 | 8.3 | 8.6 | 14.8 | 32.2 |
| 1.15 | 9.6 | 9.5 | 9.4 | 9.3 | 8.3 | 8.6 | 8.8 | 9.1 | 15.8 | 34.8 |
| 1.26 | 10.3 | 10.1 | 10.0 | 9.9 | 8.8 | 9.1 | 9.3 | 9.6 | 16.9 | 37.5 |
| 1.38 | 11.0 | 10.9 | 10.8 | 10.8 | 9.3 | 9.6 | 9.9 | 10.1 | 18.1 | 40.2 |
| 1.52 | 11.8 | 11.7 | 11.6 | 11.6 | 9.8 | 10.1 | 10.4 | 10.7 | 19.3 | 42.9 |
| 1.69 | 12.6 | 12.5 | 12.4 | 12.4 | 10.3 | 10.6 | 10.9 | 11.2 | 20.7 | 45.5 |
| 1.83 | 13.5 | 13.4 | 13.2 | 13.1 | 10.7 | 11.1 | 11.4 | 11.7 | 22.2 | 48.0 |
| 2.01 | 14.4 | 14.3 | 14.1 | 14.0 | 11.2 | 11.6 | 11.9 | 12.2 | 23.8 | 50.2 |
| 2.21 | 15.3 | 15.2 | 15.0 | 14.8 | 11.7 | 12.1 | 12.4 | 12.8 | 25.6 | 52.1 |
| 2.42 | 16.3 | 16.1 | 15.9 | 15.7 | 12.2 | 12.6 | 12.9 | 13.3 | 27.6 | 53.7 |
| 2.66 | 17.4 | 17.1 | 16.8 | 16.6 | 12.7 | 13.1 | 13.4 | 13.8 | 29.8 | 55.1 |
| 2.92 | 18.5 | 18.2 | 17.9 | 17.6 | 13.2 | 13.6 | 13.9 | 14.3 | 32.4 | 56.3 |
| 3.21 | 19.7 | 19.3 | 19.0 | 18.6 | 13.8 | 14.2 | 14.6 | 15.0 | 35.3 | 57.4 |
| 3.52 | 21.1 | 20.6 | 20.1 | 19.6 | 14.4 | 14.9 | 15.3 | 15.8 | 38.5 | 58.6 |
| 3.86 | 22.5 | 21.9 | 21.3 | 20.7 | 15.1 | 15.6 | 16.1 | 16.5 | 42.2 | 59.8 |
| 4.24 | 24.0 | 23.3 | 22.7 | 22.0 | 15.8 | 16.4 | 16.9 | 17.4 | 46.2 | 61.2 |
| 4.66 | 25.7 | 24.9 | 24.2 | 23.4 | 16.7 | 17.3 | 17.8 | 18.3 | 50.6 | 62.8 |
| 5.11 | 27.4 | 26.6 | 25.7 | 24.8 | 17.7 | 18.3 | 19.0 | 19.6 | 55.3 | 64.5 |
| 5.61 | 29.4 | 28.4 | 27.4 | 26.4 | 18.9 | 19.6 | 20.3 | 21.0 | 60.2 | 66.3 |
| 6.16 | 31.5 | 30.4 | 29.2 | 28.1 | 20.3 | 21.0 | 21.7 | 22.5 | 65.2 | 68.0 |
| 6.76 | 33.7 | 32.5 | 31.2 | 30.0 | 21.8 | 22.6 | 23.5 | 24.3 | 70.3 | 69.8 |
| 7.42 | 36.1 | 34.7 | 33.4 | 32.0 | 23.6 | 24.5 | 25.4 | 26.2 | 75.3 | 71.4 |
| 8.15 | 38.6 | 37.1 | 35.6 | 34.2 | 25.6 | 26.6 | 27.6 | 28.6 | 80.1 | 72.9 |
| 8.94 | 41.3 | 39.7 | 38.0 | 36.4 | 27.9 | 29.0 | 30.2 | 31.3 | 84.6 | 74.3 |
| 9.82 | 44.2 | 42.5 | 40.8 | 39.1 | 30.5 | 31.8 | 33.1 | 34.3 | 88.6 | 75.8 |
| 10.78 | 47.3 | 45.4 | 43.6 | 41.7 | 33.4 | 34.9 | 36.4 | 37.8 | 92.1 | 77.2 |

The intermediate particle size range may encompass the entire size range of Table 10 (i.e., 1.05 to 10.78 microns) or may consist of any sub-range therein (e.g., 1.05 to 8.94 microns or 1.26 microns to 9.82 microns), each of which is omitted herein for brevity but will be understood to comprise distinct embodiments of the invention. Further, the intermediate particle size range may be defined at the lower end of the range by any of the values described elsewhere herein, including about 0.25 microns, about 0.5 microns, about 0.75 microns, or about 1 micron and defined at the upper end by any of the particle size values in Table 7 or Table 10. Similarly, the lower end of the intermediate particle size range may be defined by any of the values in Table 7 or Table 10 and the upper end of the range defined by any of the values described elsewhere herein, including about 20 microns, about 15 microns, about 12.5 microns, and about 10 microns.

The volume percent of calcium carbonate particles within the intermediate size range may be, without limitation, the volume percent of $\overline{X}_{(A,B,C)}$ (−3 SD) or greater at each particle size, the volume percent of $\overline{X}_{(A,B,C)}$ (−2 SD) or greater at each particle size, the volume percent of $\overline{X}_{(A,B,C)}$ (−1 SD) or greater at each particle size, the volume percent of $\overline{X}_{(A,B,C)}$ or greater at each particle diameter, or the volume percent of calcium carbonate particles within the intermediate size range may be defined as greater than the volume percent of $\overline{X}_{(D,E,F)}$ at each particle diameter, greater than the volume percent of $\overline{X}_{(D,E,F)}$ (+1 SD) at each particle diameter, greater than the volume percent of $\overline{X}_{(D,E,F)}$ (+2 SD) at each particle diameter, or greater than the volume percent of $\overline{X}_{(D,E,F)}$ (+3 SD) at each particle diameter. The invention further embraces intermediate size range volume percents defined on the lower end of the range as the volume percent of any limited by the requirement that sufficient volume be provided in the large particle size range and, optionally, in the small particle size range. In some embodiments, the upper end of the volume percent range may be the volume percent of any of $\overline{X}_{(A,B,C)}$ (+3 SD), $\overline{X}_{(A,B,C)}$ (+2 SD), or $\overline{X}_{(A,B,C)}$ (+1 SD) over the same particle size range, the data for which is provided in Table 7 above.

Table 11 compares the volume (%) of particles of size less than 1.05 microns between $\overline{X}_{(A,B,C)}$ (including ±3 SD), $\overline{X}_{(D,E,F)}$, Sample G, and Sample H. It is apparent that Sample H has a substantially larger volume of particles in the small particle size range than any of the other powders, whereas $\overline{X}_{(D,E,F)}$ has the least volume in this range. In embodiment where the small particle range is defined as less than about 1 micron, preferred calcium carbonate powders according to the invention will have volume percents of greater than about 8 microns, greater than about 10 percent, greater than about 11 percent. While there is essentially no constraint placed on the upper limit of the volume in the small particle size range, it should not be so large as to reduce the volume of particles in the large particle size range or more important intermediate size ranges. Thus, preferred calcium carbonate powders will have at most about 15 percent and preferably at most about 13 percent of the volume in the small particle size range, particularly where the small range is defined as particle less than 1 micron in diameter.

TABLE 11

Volume (%) of Particles of Size Less Than Channel Diameter of 1.05 microns

| Sample H | 32.2 |
|---|---|
| Sample G | 14.8 |

TABLE 11-continued

Volume (%) of Particles of Size Less Than
Channel Diameter of 1.05 microns

| $\overline{X}_{(A,B,C)}$ + 3SD | 12.1 |
|---|---|
| $\overline{X}_{(A,B,C)}$ | 11.8 |
| $\overline{X}_{(A,B,C)}$ − 3SD | 11.6 |
| $\overline{X}_{(D,E,F)}$ | 7.9 |

Table 12 compares the volume percent of particles in the intermediate size range expressed as the difference between volume (%) of particles of size less than 10.78 microns and volume (%) of particles of size less than 1.05 microns for $\overline{X}_{(A,B,C)}$ (including −3 SD, −2 SD, and −1 SD), $\overline{X}_{(D,E,F)}$ (including +1 SD, +2 SD, and +3 SD), Sample G, and Sample H. The data in Table 12 is obtained by subtracting the total volume percent less than 1.05 microns from the total volume percent less than 10.78 microns and therefore may be said to represent the volume percent of particles in the intermediate range from and including 1.05 microns to less than 10.78 microns.

TABLE 12

Difference Between Volume (%) of Particles of
Size Less Than Channel Diameter of 10.78
microns and Volume (%) of Particles of Size
Less Than Channel Diameter of 1.05 microns

| Sample H | 47.4 |
|---|---|
| Sample G | 77.3 |
| $\overline{X}_{(A,B,C)}$ + 3SD | 43.8 |
| $\overline{X}_{(A,B,C)}$ + 2SD | 42.0 |
| $\overline{X}_{(A,B,C)}$ + 1SD | 40.4 |
| $\overline{X}_{(A,B,C)}$ | 38.4 |
| $\overline{X}_{(A,B,C)}$ − 1SD | 36.6 |
| $\overline{X}_{(A,B,C)}$ − 2SD | 34.9 |
| $\overline{X}_{(A,B,C)}$ − 3SD | 33.1 |
| $\overline{X}_{(D,E,F)}$ + 3SD | 29.7 |
| $\overline{X}_{(D,E,F)}$ + 2SD | 28.1 |
| $\overline{X}_{(D,E,F)}$ + 1SD | 26.8 |
| $\overline{X}_{(D,E,F)}$ | 25.6 |

As shown in Table 12, $\overline{X}_{(D,E,F)}$ provides the least volume percent in the intermediate size range of about 1 to about 11 microns. Thus, the volume percent required to achieved enhanced absorption efficiency is, according to one embodiment, at least about 26 percent. With due regard for the standard deviations of the $\overline{X}_{(D,E,F)}$ powder, other embodiments include without limitation, at least about 27 percent by volume, at least about 28 percent by volume, and at least about 30 percent by volume, particularly where the intermediate range is defined as about 1 micron to about 11 microns. In other embodiments, the intermediate range will comprise about 33 percent or more, about 35 percent or more, or about 36 percent or more of the total volume of calcium carbonate powder, particularly where the intermediate range is defined as about 1 to about 11 microns. The upper end of the volume range is not particularly limited but must not be so large as to substantially reduce the volume of particles in the small size region or, more significantly, in the large particle size region. For example, Sample G (Calcium Carbonate[5]) possess the most volume in the intermediate particle size range, having the substantial bulk of its volume within the range of about 1 to about 11 microns. However, as demonstrated in Example 1, Calcium Carbonate[5] does not shown significant improvement in absorption efficiency or calcium balance after an eight-week feeding regimen as compared to any of the other calcium carbonate powders. As shown in Table 13, Sample G is clearly deficient in the large particle size region. Thus, in preferred embodiments, the calcium carbonate of the invention will have a volume percent range of intermediate size particles defined at the upper end by about 60, about 55, or about 50 percent of the total volume of calcium carbonate, and more preferably about 40 percent, about 42 percent, and about 44 percent of the total volume of calcium carbonate, particularly where the intermediate size range is defined as about 1 micron to about 11 microns.

In one embodiment, the intermediate particle size range is about 1 micron to about 11 microns and the volume percent of particles within this range is about 33 to about 44 percent, about 35 to about 42 percent, about 36 to about 41 percent, about 37 to about 41 percent, or about 38 percent. In another embodiment, the intermediate particle size range is about 0.5 microns to about 11 microns and the volume percent of particles within this range is about 37 to about 49 percent, about 40 to about 46 percent, about 42 percent to about 44 percent, or about 43 percent. Preferred volume percent ranges are established over any given range of intermediate particle sizes as the volume percent differences between $\overline{X}_{(A,B,C)}$ (+3 SD) and $\overline{X}_{(A,B,C)}$ (−3 SD); $\overline{X}_{(A,B,C)}$ (+2 SD) and $\overline{X}_{(A,B,C)}$ (−2 SD); or $\overline{X}_{(A,B,C)}$ +1 SD) and $\overline{X}_{(A,B,C)}$ (−1 SD) over the particle size range which can be readily calculated based on the data provided in Table 7.

Table 13 compares the volume percent of particles in the large particle size region for the various calcium carbonate powders. It is seen that Sample G lacks substantial volume of large particles, such as particles greater than about 11 microns in diameter. This observation is believed to explain the inability of Calcium Carbonate[5] to increase calcium absorption efficiency and calcium balance relative to other calcium carbonate powders, as described in Example 1. Sample G (Calcium Carbonate[2]) is similarly deficient.

TABLE 13

Volume (%) of Particles of Size Greater Than
Channel Diameter of 10.78 microns

| $\overline{X}_{(D,E,F)}$ | 66.6 |
|---|---|
| $\overline{X}_{(A,B,C)}$ + 3SD | 58.3 |
| $\overline{X}_{(A,B,C)}$ + 2SD | 56.4 |
| $\overline{X}_{(A,B,C)}$ + 1SD | 54.6 |
| $\overline{X}_{(A,B,C)}$ | 52.7 |
| $\overline{X}_{(A,B,C)}$ − 1SD | 50.8 |
| $\overline{X}_{(A,B,C)}$ − 2SD | 48.9 |
| $\overline{X}_{(A,B,C)}$ − 3SD | 47.0 |
| Sample G | 7.9 |
| Sample H | 22.8 |

In the broadest embodiments of the invention, the volume percent of large particles will typically be greater than 23 percent, and more typically will be greater than about 30 percent, preferably greater than about 35 percent, and more preferably greater than about 40 percent of the total volume of the calcium carbonate powder. Preferred volume percent ranges of large particles may be defined as, for example, the volume percent ranges defined at the upper and lower ends by $\overline{X}_{(A,B,C)}$ (+3 SD) and $\overline{X}_{(A,B,C)}$ (−3 SD); $\overline{X}_{(A,B,C)}$ (+2 SD) and $\overline{X}_{(A,B,C)}$ (−2 SD); or $\overline{X}_{(A,B,C)}$ (+1 SD) and $\overline{X}_{(A,B,C)}$ (−1 SD), respectively, including for example, in the case where the large particle range is defined as greater than about 11 microns, about 47 to about 59 percent, about 49 to about 57 percent, or about 51 to about 55 percent of the total volume of the calcium carbonate powder. In embodiments where the lower end of the large particle range is about 7.5 micron, about 10 microns, about 12.5 microns, or about 15 microns, preferred volume percent ranges can be similarly calculated based on the data in Table 7.

All ranges disclosed herein will be understood to explicitly disclose every value within the range, each intermediate value being omitted herein for the sake of brevity. Thus, the reader will understand that, for example, the intermediate particle size range of about 0.25 to about 10 microns explicitly discloses particle sizes of, for example, about 0.3, 0.4, 0.5, 0.6, 0.7, 0.8 and 0.9 microns and about 1, 2, 3, 4, 5, 6, 7, 8, and about 9 microns. Further, the ranges will be understood to disclose every sub-range therein. Thus, the upper and lower endpoints of each sub-range will include every intermediate value within the range. For example, the small particle size range of, for example, less than about 1 micron, will include sub-ranges of less than about 0.9, 0.8, 0.7, 0.6, 0.5, 0.4, 0.3, 0.2, or about 0.1 micron. The intermediate particle size ranges, including for example about 0.25 to about 10 microns, will explicitly disclose sub-ranges wherein the lower end is increased in increments of 0.05 (i.e., 0.3 to 10, 0.4 to 10, etc.), 0.1 (0.35 to 10, 0.45 to 10, etc.), 0.5 (0.75 to 10, 1.25 to 10, etc.), or 1 micron (1.25 to 10, 2.25 to 10, etc.) and wherein the upper end of the range is decreased in increments of 0.5 (i.e., 0.25 to 9.5, 0.25 to 9, etc.) or 1 (i.e. 0.25 to 9, 0.25 to 8, 0.25 to 7, etc.), as well as any sub-ranges formed by increasing the lower endpoint and decreasing the upper end point in this manner. All such sub ranges are omitted herein for brevity but will be understood to be explicitly disclosed.

While the preferred embodiment described above utilize mined limestone calcium carbonate, the invention is not so limited and also embraces in some embodiments precipitated calcium carbonate powders which meet the particle size distribution requirements described herein. Precipitated calcium carbonates can be prepared having a variety of crystal habits, including cubic, prismatic, rose-shaped, needle-shaped, barrel-shaped and the like, which are expected to have different capabilities toward paracellular diffusion. Accordingly, each of the foregoing crystal forms is contemplated to be an embodiment of the invention. Typically, though not always, precipitated calcium carbonate powders have a narrower particle size distribution than mined calcium carbonate powder which have been ground. Therefore, when using precipitated calcium carbonate powders, it might be necessary to combine one or more powders to achieve sufficient volume in the small, intermediate, and large particle size ranges. It is within the skill in the art to provide powders have such distributions using mesh screening or similar techniques and by combining commercially available calcium carbonate powders of varying average particle size. In preferred embodiments, the calcium carbonate powders are USP grade rather than food grade, as food grade powders may comprise substantial levels impurities which interfere with calcium absorption. In this regard, it will be recognized that food grade calcium carbonate powders may be functionally very different than USP or pharmaceutical grade powders.

In determining whether a particular calcium carbonate powder meets the requirement described herein, it is preferred to measure the particle size distributions using a Beckman Coulter LS13 320 Particle Size Analyzer with the Aqueous Liquid Sample Module or comparable particle size analyzer using the parameter defined herein. The Beckman Coulter LS13 320 Particle Size Analyzer and the Aqueous Liquid Sample Module are described in Beckman Coulter publication BR-9809A (2004), the contents of which are incorporated by reference, and complies with ISO 13320-1:1999 (Particle size analysis—Laser diffraction methods—Part 1: General principles) as described in Beckman Coulter publication TA-403, the content of which is incorporated by reference. The term "channel diameter" is used synonymously with particle size.

Example 3

Due to the enhanced absorption attainable with the calcium carbonate powders of the invention, less calcium carbonate, on a weight basis, will be required to provide a supplement which meets the Dietary Reference Intakes (DRIs), as compared to other calcium carbonate powders having lower absorption.

The DRIs set by the Institute of Medicine of the National Academy of Sciences are provided in terms of Adequate Intakes (AIs). See Standing Committee on the Scientific Evaluation of Dietary Reference Intakes, Food and Nutrition Board, Institute of Medicine. Dietary Reference Intakes for Calcium, Phosphorus, Magnesium, Vitamin D and Fluoride, Washington D.C.: The National Academies Press, 1997. The recommended AI for children and teenagers 9 to 18 years olds is 1,300 mg of elemental calcium per day. For adults of age 19 to 50 years, the AI is 1,000 mg of elemental calcium per day and for adults over 50 the AI is 1,200 mg per day. These values reflect the recognition that not all calcium consumed is actually utilized. Rather, in the case of adults, the elemental calcium AI values of 1,000 mg and 1,200 mg are based on the observation that only about 30% of the calcium will be absorbed, as reported by Heaney et al., "Variability of calcium absorption," *Am. J. Clin. Nutr.* 47: 262-264 (1988), which is hereby incorporated by reference, and for the 9 to 18 year olds group the value of 1,300 mg reflects a percent absorption of 38%, as reported by Wastney et al., "Differences in calcium kinetics between adolescent girls and young women," *Am. J. Physiol.* 271: R208-R216 (1996), which is hereby incorporated by reference.

Accordingly, much of the elemental calcium present in a conventional calcium supplement will not be absorbed through the intestine but rather will be excreted, as indicated by $V_f$ in FIG. 1. In the case of adults, for example, $V_f$ will account for approximately 70% of the elemental calcium in a conventional calcium supplement. In contrast, the calcium carbonate powders of the present invention exhibit a surprisingly higher percent absorption, i.e., absorption efficiency $(V_i-V_f)/V_i$ expressed on a percentage basis, than the relatively low percent absorption values used to derive the recommended AI (e.g., 30%). As shown in Table 4 of Example 1, a percentage absorption of 50% or above is attainable with the inventive calcium carbonate powders, such as OMYA-Cal® USP-10-AZ (Diet 2). It will therefore be apparent that less of the calcium carbonate powder of the present invention will be required to provide the desired daily amount of elemental calcium as compared to other commercially available sources of calcium.

For example, a calcium supplement having 360 mg of elemental calcium provided by the calcium carbonate powder of the present invention (e.g., OMYA-Cal® USP-10-AZ), which is 50% absorbable, is expected to deliver the same amount of absorbable elemental calcium as a conventional tablet having 600 mg of elemental calcium, which is 30% absorbable, i.e., (360 mg)×(0.50)=(600 mg)×(0.30). The concomitant reduction in tablet size will therefore be quite large, as about 900 mg of calcium carbonate powder according to the invention is expected to deliver the same amount of elemental calcium as about 1,500 mg of conventional calcium carbonate powder. Put another way, by employing the calcium carbonate powers of the invention in place of conventional calcium carbonate powders, about 40% less calcium carbonate will be required to deliver the same absorbable elemental calcium dose and, consequently, the tablet volume required to provide a given dose of absorbable elemental calcium will also be reduced by about 40%.

It has heretofore proven impractical to formulate a single dose tablet which supplies the daily requirement of elemental calcium because the size of the tablet would be larger than most consumers find tolerable to swallow. With conventional calcium carbonate powder (i.e., calcium carbonate powder which is about 30% absorbable in adults), the AI of 1,200 mg of elemental calcium would require that a single tablet comprise about 3 g of calcium carbonate. Such a large amount of calcium carbonate cannot be compressed into a tablet small enough to swallow without discomfort. Not surprisingly, commercially available calcium supplements, such as Caltrate®, are typically provided as a two-a-day formulation having 600 mg of elemental calcium per tablet, such that two tablets are required to provide the recommended daily AI of elemental calcium for adults. However, with the highly bioavailable calcium forms of the present invention, a calcium supplement need only comprise 720 mg of elemental calcium, rather than 1,200 mg, to deliver the same amount of absorbable elemental calcium, i.e, (720 mg)×(0.50)=(1,200 mg)×(0.30). Because 720 mg of elemental calcium is provided by about 1,800 mg of calcium carbonate, once-daily tablets which are not objectionable to swallow can be prepared with the calcium carbonate powder according to the invention, including but not limited to OMYA-Cal® USP-10-AZ.

To further evaluate the reduction in tablet size obtainable using the highly absorbable calcium carbonate powders of the invention, as series of tablets were prepared as once-daily and twice-daily supplements capable of providing amounts of absorbable calcium equivalent to the AIs of 1,000 mg, 1,200 mg, and 1,300 mg of elemental calcium per day. In each case, the tablets were prepared from a calcium carbonate granulation having the formulation of Table 14 which delivers about 37.5% by weight elemental calcium.

TABLE 14

| Component | Weight % |
| --- | --- |
| OMYA-Cal ® USP-10-AZ | 93 |
| maltodextrin | 5.0 |
| mineral oil | 1.0 |
| glycerin | 0.5 |
| water | 0.5 |

The granulation was prepared according to the method for making high density calcium carbonate granulation described in U.S. patent application Ser. No. 10/631,923, the contents of which are hereby incorporated by reference. Briefly, this method entailed mixing the calcium carbonate powder (OMYA-Cal® USP-10-AZ) and binder (maltodextrin) in a Collette Gral Model 600 high shear mixer for about one minute at mixer speeds from about 200 to about 300 rpm, adding water heated to about 93° C. to the mixture through a water line and mixing for an additional period until steam stopped being produced from the composition, then spraying onto the composition the mineral oil and glycerin using a spray nozzle fed by a line through the head of the mixer with continued mixing for about one minute. The resulting granulation was dried to a water content of 0.5% by weight in a Carrier model QAD/C 1260 S horizontal fluidized bed convection oven at a product temperature between 100° C. and 150° C.

The granulation was compressed into tablets comprising 300 mg, 360 mg, 390 mg, 500 mg, 600 mg, 650 mg, 720 mg, 780 mg, 1000 mg, 1200 mg, and 1300 mg of elemental calcium, plus an overage of 5% by weight in each case, using conventional techniques. The rational for each of these dosages is as follows: (1) For a recommended AI of 1,000 mg, once-daily and twice-daily tablets will comprise 1,000 mg and 500 mg of elemental calcium, respectively, based on the conventional 30% absorption value, or will comprise 600 mg and 300 mg of elemental calcium, respectively, based on the 50% absorption value of the calcium carbonate according to the present invention; (2) For a recommended AI of 1,200 mg, once-daily and twice-daily tablets will comprise 1,200 mg and 600 mg of elemental calcium, respectively, based on the conventional 30% absorption value, or will comprise 720 mg and 360 mg of elemental calcium, respectively, based on the 50% absorption value of the calcium carbonate according to the present invention; (3) For a recommended AI of 1,300 mg, once-daily and twice-daily tablets will comprise 1,300 mg and 650 mg of elemental calcium, respectively, based on the conventional 30% absorption value, or will comprise 780 mg and 390 mg of elemental calcium, respectively, based on the 50% absorption value of the calcium carbonate according to the present invention. For the AI of 1,300 mg, the absorbable elemental calcium dose is based on the fractional absorption value of 30% for adults reported by Heaney et al., rather than the value of 38% for the 9 to 18 year old group reported by Wastney et al., in recognition of the emerging consensus in the art that calcium intakes for adults should be increased.

The volume of each of the foregoing tablets was determined by one or more techniques. The preferred method for determining tablet volume involves the use of a graduated cylinder or the like to measure the volume of glycerin, or other suitable liquid, displaced by the tablets. Preferably, a flask having an overflow spout is filled with glycerin to the point where any increase in volume will cause glycerin to spill over into the overflow spout and collect in a graduated cylinder. Several tablets are then added to the flask and the volume of displaced glycerin which is collected in the graduated cylinder is measured and divided by the number of tablets added to give the volume of each tablet. Alternatively, volume may be measured by laser imaging techniques or by direct dimensional measurements using of cylindrical or disc shaped tablets, for example.

The volume of once-daily and twice-daily tablets required to deliver an effective amount of elemental calcium equivalent to an AI of 1,000 mg are given in Table 15, for calcium carbonate powders having 50% absorption efficiency according to the invention and conventional powders having 30% absorption according to the prior art.

TABLE 15

| | Adequate Intake (AI) of 1,000 mg | | | | |
| --- | --- | --- | --- | --- | --- |
| | elemental calcium per tablet (mg) | calcium carbonate per tablet (mg) | tablet weight (g) | tablet volume (mL) | Comfortable to swallow? |
| | | 50% Absorption | | | |
| Once-daily: | 600 | 1,499 | 1.69 | 0.84 | good |
| Twice-daily: | 300 | 749 | 0.86 | 0.44 | excellent |
| | | 30% Absorption | | | |
| Once-daily: | 1,000 | 2,498 | 2.79 | 1.35 | poor |
| Twice-daily: | 500 | 1,249 | 1.41 | 0.67 | good |

In one embodiment of the invention, once-daily tablets are provided comprising an amount of highly absorbable (i.e., at least about 40%, preferably, at least about 45%, and more preferably, at least about 50%) calcium carbonate powder according to the invention sufficient to supply, in a single tablet, an effective amount of absorbable elemental calcium equivalent to the AI of 1,000 mg (based on an absorption value of 30%). Preferably, the calcium carbonate powder according to the invention are at least about 50% absorbable, in which case, once-a-day tablets according to this embodiment will typically comprise from about 1,350 to about 1,650 mg, preferably from about 1,425 to about 1,575 mg, and more preferably about 1,500 mg (±5%) of the highly absorbable calcium carbonate powders described herein, including but not limited to OMYA-Cal® USP-10-AZ. The tablets according to this embodiment, will typically, but not necessarily, have a volume less than about 1.30 or about 1.20 mL (cm$^3$), preferably less than about 1.10 mL, more preferably less than about 0.95 mL, and more preferred still, less than about 0.85 mL. In a particularly interesting embodiment, about 1,500 mg (±5%) of calcium carbonate according to the invention will be provided in a tablet having a volume in the range of about 0.75 to about 1 mL, preferably, from about 0.80 to about 0.90 mL, and will be capable of delivering substantially the same amount (i.e., within ±10%, preferably within ±5% and more preferably within ±2.5%) of absorbable calcium as: (1) 30% of the AI of 1,000 mg (i.e., 300 mg of elemental calcium); and/or (2) the amount of calcium absorbable from about 2,500 mg of a conventional calcium carbonate powder, e.g., one exhibiting about 30% absorption in adults.

In a related embodiment, twice-daily tablets are provided which, individually, comprise an amount of the highly absorbable calcium carbonate powder according to the invention sufficient to supply an effective amount of absorbable elemental calcium equivalent to half of the AI of 1,000 mg (based on an absorption value of 30%) such that two tablet are capable of providing the full AI of 1,000 mg. Preferably, the calcium carbonate powder according to the invention are at least about 50% absorbable, in which case, a tablet according to this embodiment will typically comprise from about 700 to about 800 mg, preferably from about 725 to about 775 mg, and more preferably about 750 mg (±5%) of the highly absorbable calcium carbonate powders described herein, including but not limited to OMYA-Cal® USP-10-AZ. The tablets according to this embodiment, will typically, but not necessarily, have a volume less than about 0.60 mL, preferably less than about 0.50 mL, and more preferably less than about 0.45 mL. In a particularly interesting embodiment, about 750 mg (±5%) of calcium carbonate according to the invention will be provided in a tablet having a volume in the range of about 0.3 to about 0.6 mL, preferably, from about 0.35 to about 0.55 mL, more preferably from about 0.40 to about 0.50 mL, included a representative embodiment of about 0.45 mL, and will be capable of delivering substantially the same amount (i.e., within ±10%, preferably within ±5% and more preferably within ±2.5%) of absorbable calcium as: (1) half of 30% of the AI of 1,000 mg (i.e., 150 mg of elemental calcium); and/or (2) the amount of calcium absorbable from about 1,250 mg of a conventional calcium carbonate powder, e.g., one exhibiting about 30% absorption in adults.

The volume of once-daily and twice-daily tablets required to deliver an effective amount of elemental calcium corresponding to an AI of 1,200 mg, for 50% absorption according to the invention and 30% absorption of the prior art, are given in Table 16.

TABLE 16

| AI of 1,200 mg | | | | | |
|---|---|---|---|---|---|
| | elemental calcium (mg) per tablet | calcium carbonate (mg) | tablet weight (g) | tablet volume (mL) | Comfortable to swallow? |
| 50% Absorption | | | | | |
| Once-daily: | 720 | 1,798 | 2.04 | 0.99 | good |
| Twice-daily: | 360 | 899 | 1.02 | 0.51 | excellent |
| 30% Absorption | | | | | |
| Once-daily: | 1,200 | 2,997 | 3.37 | 1.66 | very poor |
| Twice-daily: | 600 | 1,449 | 1.69 | 0.84 | good |

In one embodiment of the invention, once-daily tablets are provided comprising an amount of highly absorbable (i.e., at least about 40%, preferably, at least about 45%, and more preferably, at least about 50%) calcium carbonate powder according to the invention sufficient to supply, in a single tablet, an effective amount of absorbable elemental calcium equivalent to the AI of 1,200 mg (based on an absorption value of 30%). In particularly interesting embodiments, the calcium carbonate powders according to the invention are at least about 50% absorbable, in which case, once-a-day tablets according to this embodiment will typically comprise from about 1,500 to about 2,500 mg, preferably from about 1,600 to about 2,000 mg, and more preferably about 1,800 mg (±5%) of the highly absorbable calcium carbonate powders described herein, including but not limited to OMYA-Cal® USP-10-AZ. The tablets according to this embodiment, will typically, but not necessarily, have a volume less than about 1.60 or about 1.55 mL, preferably less than about 1.25 mL, more preferably less than about 1.10 mL, and more preferred still, less than about 1.00 mL. In a particularly interesting embodiment, about 1,800 mg (±5%) of calcium carbonate according to the invention will be provided in a tablet having a volume in the range of about 0.75 to about 1.5 mL, preferably, from about 0.80 to about 1.25 mL, more preferably from about 0.9 to about 1.10 mL, and more preferred still about 1 mL, and will be capable of delivering substantially the same amount (i.e., within ±10%, preferably within ±5% and more preferably within ±2.5%) of absorbable calcium as: (1) 30% of the AI of 1,200 mg (i.e., 360 mg of elemental calcium); and/or (2) the amount of calcium absorbable from about 3,000 mg of a conventional calcium carbonate powder, e.g., one exhibiting about 30% absorption in adults.

In a related embodiment, twice-daily tablets are provided which, individually, comprise an amount of the highly absorbable calcium carbonate powder according to the invention sufficient to supply an effective amount of absorbable elemental calcium equivalent to half of the AI of 1,200 mg (based on an absorption value of 30%) such that two tablet are capable of providing the full AI of 1,200 mg. Preferably, the calcium carbonate powder according to the invention are at least about 50% absorbable, in which case, a tablet according to this embodiment will typically comprise from about 800 mg to about 1,400 mg, preferably from about 850 mg to about 1,200 mg, more preferably from about 875 mg to about 1,100 mg, including a representative embodiment of about 900 mg (±5%) of the highly absorbable calcium carbonate powders described herein, including but not limited to OMYA-Cal® USP-10-AZ. The tablets according to this embodiment, will typically, but not necessarily, have a volume less than about 0.80 mL, preferably less than about 0.70 mL, and more preferably less than about 0.60 mL, and more preferred still, less than about 0.55 mL. In a particularly interesting embodiment, about 900 mg (±5%) of calcium carbonate according to the invention will be provided in a tablet having a volume in the range of about 0.4 to about 0.8 mL, preferably, from about 0.45 to about 0.6 mL, more preferably from about 0.45 to about 0.55 mL, included a representative embodiment of about 0.5 mL, and will be capable of delivering substantially the same amount (i.e., within ±10%, preferably within ±5% and more preferably within ±2.5%) of absorbable calcium as: (1) half of 30% of the AI of 1,200 mg (i.e., 180 mg of elemental calcium); and/or (2) the amount of calcium absorbable from about 1,450 mg of a conventional calcium carbonate powder, e.g., one exhibiting about 30% absorption in adults.

The volume of once-daily and twice-daily tablets required to deliver an effective amount of elemental calcium corresponding to an AI of 1,300 mg, for 50% absorption according to the invention and 30% absorption of the prior art, are given in Table 17.

TABLE 17

AI of 1,300 mg

|  | elemental calcium (mg) per tablet | calcium carbonate per tablet (mg) | tablet weight (g) | tablet volume (mL) | Comfortable to swallow? |
|---|---|---|---|---|---|
| 50% Absorption | | | | | |
| Once-daily: | 780 | 1,948 | 2.21 | 1.07 | good |
| Twice-daily: | 390 | 974 | 1.12 | 0.57 | excellent |
| 30% Absorption | | | | | |
| Once-daily: | 1,300 | 3,247 | 3.65 | 1.84 | very poor |
| Twice-daily: | 650 | 1,623 | 1.83 | 0.88 | good |

In one embodiment of the invention, once-daily tablets are provided comprising an amount of highly absorbable (i.e., at least about 40%, preferably, at least about 45%, and more preferably, at least about 50%) calcium carbonate powder according to the invention sufficient to supply, in a single tablet, an effective amount of absorbable elemental calcium equivalent to the AI of 1,300 mg (based on an absorption value of 30%). In particularly interesting embodiments, the calcium carbonate powders according to the invention are at least about 50% absorbable, in which case, once-a-day tablets according to this embodiment will typically comprise from about 1,750 to about 3,000 mg, preferably from about 1,800 to about 2,500 mg, more preferably from about 1,900 mg to about 2,000 mg, and more preferred still, about 1,950 mg (±5%) of the highly absorbable calcium carbonate powders described herein, including but not limited to OMYA-Cal® USP-10-AZ. The tablets according to this embodiment, will typically, but not necessarily, have a volume less than about 1.60 or about 1.55 mL, preferably less than about 1.75 mL, more preferably less than about 1.50 mL, and more preferred still, less than about 1.15 mL. In a particularly interesting embodiment, about 1,950 mg (±5%) of calcium carbonate according to the invention will be provided in a tablet having a volume in the range of about 0.80 to about 1.75 mL, preferably, from about 0.90 to about 1.50 mL, more preferably from about 0.95 to about 1.25 mL, and more preferred still from about 1 mL to about 1.15 mL, including a representative embodiment of about 1.10 mL, and will be capable of delivering substantially the same amount (i.e., within ±10%, preferably within ±5% and more preferably within ±2.5%) of absorbable calcium as: (1) 30% of the AI of 1,300 mg (i.e., 390 mg of elemental calcium); and/or (2) the amount of calcium absorbable from about 3,250 mg of a conventional calcium carbonate powder, e.g., one exhibiting about 30% absorption in adults.

In a related embodiment, twice-daily tablets are provided which, individually, comprise an amount of the highly absorbable calcium carbonate powder according to the invention sufficient to supply an effective amount of absorbable elemental calcium equivalent to half of the AI of 1,300 mg (based on an absorption value of 30%) such that two tablet are capable of providing the full AI of 1,300 mg. Preferably, the calcium carbonate powders according to the invention are at least about 50% absorbable, in which case, a tablet according to this embodiment will typically comprise from about 900 mg to about 1,500 mg, preferably from about 925 mg to about 1,200 mg, more preferably from about 950 mg to about 1,100 mg, including a representative embodiment of about 975 mg (±5%) of the highly absorbable calcium carbonate powders described herein, including but not limited to OMYA-Cal® USP-10-AZ. The tablets according to this embodiment, will typically, but not necessarily, have a volume less than about 0.85 mL, preferably less than about 0.8 mL, more preferably less than about 0.70 mL, and more preferred still, less than about 0.6 mL. In a particularly interesting embodiment, about 975 mg (±5%) of calcium carbonate according to the invention will be provided in a tablet having a volume in the range of about 0.45 to about 0.8 mL, preferably, from about 0.5 to about 0.7 mL, more preferably from about 0.55 to about 0.65 mL, included a representative embodiment in the reange of about 0.55 mL to about 0.60 mL, and will be capable of delivering substantially the same amount (i.e., within ±10%, preferably within ±5% and more preferably within ±2.5%) of absorbable calcium as: (1) half of 30% of the AI of 1,300 mg (i.e., 195 mg of elemental calcium); and/or (2) the amount of calcium absorbable from about 1,625 mg of a conventional calcium carbonate powder, e.g., one exhibiting about 30% absorption in adults.

The actual tablets for which the volume and weights were measured in Tables 15-17 included a 5% overage in the amount of calcium carbonate to account for manufacturing variability and to ensure that every tablet delivers at least the amount of elemental calcium specified.

In addition to the foregoing, it is contemplated that a tablet comprising 325 mg of elemental calcium provided by about 812 mg of OMYA-Cal® USP-10-AZ or other calcium carbonate powder according to the invention will be especially useful, particularly for administration to children supplement for children. In one embodiment, the tablet will comprise from about 812 mg to about 853 mg of OMYA-Cal® USP-10-AZ or other suitable powder according to the invention. It is believed that such a supplement will have a volume between about 0.45 and about 1 mL, preferably between about 0.6 and about 0.9 mL, including representative embodiments of about 0.7 mL, 0.75 mL, 0.8 mL, and 0.85 mL.

While this example used the calcium carbonate powder OMYA-Cal® USP-10-AZ, any of the calcium powders described herein, including those described in Example 2, are contemplated to be equally suitable in preparing the once-daily and twice daily tablets described herein. The tablets according to this example are contemplated to be especially suited for use in the methods described herein, including the methods for treating or preventing osteoporosis and building bone mass.

It will be understood that the foregoing embodiments directed to providing the elemental calcium equivalent of the AIs of 1,000 mg, 1,200 mg, and 1,300 mg elemental calcium are merely illustrative of the various tablets that can be prepared according to the invention. For example, it will be observed that for any desired amount of elemental calcium delivery, tablets of the present invention will be smaller than prior art tablets due to the fact that less of the highly absorbable calcium carbonate of the invention need be included to achieve the same effective delivery of absorbable calcium as compared to prior art calcium carbonate powders. Further, while this example describes tablets which are prepared using the methods for making very small tablets described in U.S. patent application Ser. No. 10/631,923, it will be understood that a comparable reduction in size (e.g., about 40%) can be achieved using any granulation and tableting method known in the art, due to the fact that less calcium carbonate powder is required to deliver a comparable amount of absorbable elemental calcium than prior art powders.

The most preferred calcium carbonate powders according the present invention will have a percent absorption, in children and/or adults, of at least about 50%. However, the invention is not so limited and embraces all calcium carbonate powders having particle size distributions defined herein, wherein the percent absorption in adults is at least about 35%, preferably at least about 40%, and more preferably at least about 45% and/or the percent absorption in children and teens aged 9 to 18 is at least about 35%, preferably at least about 40%, and more preferably at least about 45%. It will be understood that these values represent the average percent absorption in a population and there may be significant variability on an individual basis.

All patent and non-patent literature referenced in this specification is hereby incorporated by reference.

The invention having been described by the foregoing description of the preferred embodiments, it will be understood that the skilled artisan may make modifications and variations of these embodiments without departing from the spirit or scope of the invention as set forth in the following claims:

We claim:

1. A swallowable calcium dietary supplement tablet comprising about 1,500 mg of precipitated calcium carbonate powder, said precipitated calcium carbonate powder being combined with one or more additional calcium carbonate powders and, said tablet having a volume from about 0.75 to about 1 ml, wherein said precipitated calcium carbonate powder has a crystalline form other than cubic or prismatic.

2. A calcium dietary supplement tablet according to claim 1 having a volume from about 0.8 to about 0.9 ml.

3. A calcium dietary supplement tablet according to claim 1, further Comprising maltodextrin, oil, and glycerin.

4. A calcium dietary supplement tablet according to claim 1, wherein the precipitated calcium carbonate comprises rose-shaped crystals.

5. A calcium dietary supplement tablet according to claim 1, wherein the precipitated calcium carbonate comprises needle-shaped crystals.

6. A calcium dietary supplement tablet according to claim 1, wherein the precipitated calcium carbonate comprises barrel-shaped crystals.

7. A calcium dietary supplement tablet according to claim 1, wherein the precipitated calcium carbonate is food grade.

8. A calcium dietary supplement tablet according to claim 1, wherein the precipitated calcium carbonate is USP grade.

9. A calcium dietary supplement tablet according to claim 1, further comprising at least about 200 I.U. of vitamin D.

10. A calcium dietary supplement tablet according to claim 1, further comprising at least about 400 I.U. of vitamin D.

11. A calcium dietary supplement tablet according to claim 1, further comprising at least about 600 I.U. of vitamin D.

12. A calcium dietary supplement tablet according to claim 1, further comprising at least about 800 I.U. of vitamin D.

13. A calcium dietary supplement tablet according to claim 1, further comprising at least about 1,000 I.U. of vitamin D.

* * * * *